(12) United States Patent
Foucher et al.

(10) Patent No.: US 6,549,327 B2
(45) Date of Patent: Apr. 15, 2003

(54) PHOTOCHROMIC GYRICON DISPLAY

(75) Inventors: Daniel A. Foucher, Rochester, NY (US); Raj D. Patel, Oakville (CA); Naveen Chopra, Oakville (CA); Peter M. Kazmaier, Mississauga (CA); Erwin Buncel, Kingston (CA); James Wojtyk, Ottawa (CA)

(73) Assignee: Xerox Corporation, Stamford, CT (US)

( * ) Notice: Subject to any disclaimer, the term of this patent is extended or adjusted under 35 U.S.C. 154(b) by 174 days.

(21) Appl. No.: 09/864,386

(22) Filed: May 24, 2001

(65) Prior Publication Data
US 2002/0186450 A1 Dec. 12, 2002

(51) Int. Cl.[7] .................................................. G09G 3/08
(52) U.S. Cl. ...................................................... 359/296
(58) Field of Search ...................... 359/296; 430/108.21, 430/108.1, 108.2, 137.14, 120, 108.22, 19, 962; 106/31.64, 31.17, 31.32

(56) References Cited

U.S. PATENT DOCUMENTS

| | | | |
|---|---|---|---|
| 3,612,758 A | 10/1971 | Evans et al. | 178/5.4 R |
| 4,126,854 A | 11/1978 | Sheridon | 340/373 |
| 4,143,103 A | 3/1979 | Sheridon | 264/4 |
| 4,261,653 A | 4/1981 | Goodrich | 350/362 |
| 4,438,160 A | 3/1984 | Ishikawa et al. | 427/214 |
| 4,810,431 A | 3/1989 | Leidner | 264/15 |
| 5,262,098 A | 11/1993 | Crowley et al. | 264/8 |
| 5,344,594 A | 9/1994 | Sheridon | 264/4.1 |
| 5,366,841 A * | 11/1994 | Patel et al. | 430/108.21 |
| 5,370,963 A * | 12/1994 | Patel et al. | 430/108.21 |
| 5,389,945 A | 2/1995 | Sheridon | 345/85 |
| 5,551,973 A | 9/1996 | Oliver et al. | 106/22 B |
| 5,593,486 A | 1/1997 | Oliver et al. | 106/22 A |
| 5,604,027 A | 2/1997 | Sheridon | 428/323 |
| 5,633,109 A | 5/1997 | Jennings et al. | 430/115 |
| 5,708,525 A | 1/1998 | Sheridon | 359/296 |
| 5,710,420 A | 1/1998 | Martin et al. | 235/487 |
| 5,717,514 A | 2/1998 | Sheridon | 359/296 |
| 5,717,515 A | 2/1998 | Sheridon | 359/296 |
| 5,737,115 A | 4/1998 | Mackinlay et al. | 359/296 |
| 5,739,801 A | 4/1998 | Sheridon | 345/84 |
| 5,751,268 A | 5/1998 | Sheridon | 345/107 |
| 5,754,332 A | 5/1998 | Crowley | 359/296 |
| 5,759,729 A | 6/1998 | Martin et al. | 430/106 |
| 5,760,761 A | 6/1998 | Sheridon | 345/107 |
| 5,767,826 A | 6/1998 | Sheridon et al. | 345/84 |
| 5,777,782 A | 7/1998 | Sheridon | 359/296 |
| 5,808,783 A | 9/1998 | Crowley | 359/296 |
| 5,815,306 A | 9/1998 | Sheridon et al. | 359/296 |
| 5,825,529 A | 10/1998 | Crowley | 359/296 |
| 5,891,479 A | 4/1999 | Sheridon | 425/8 |
| 5,892,497 A | 4/1999 | Robertson | 345/107 |
| 5,894,367 A | 4/1999 | Sheridon | 359/623 |
| 5,904,790 A | 5/1999 | Sheridon | 156/83 |
| 5,914,805 A | 6/1999 | Crowley | 359/296 |
| 5,917,646 A | 6/1999 | Sheridon | 359/296 |
| 5,919,409 A | 7/1999 | Sheridon | 264/8 |
| 5,922,268 A | 7/1999 | Sheridon | 264/437 |
| 5,930,026 A | 7/1999 | Jacobson et al. | 359/296 |
| 5,961,804 A | 10/1999 | Jacobson et al. | 204/606 |
| 5,982,346 A | 11/1999 | Sheridon et al. | 345/85 |
| 5,989,629 A | 11/1999 | Sacripante et al. | 427/180 |
| 6,017,584 A | 1/2000 | Albert et al. | 427/213.3 |
| 6,038,059 A | 3/2000 | Silverman | 359/296 |
| 6,055,091 A | 4/2000 | Sheridon et al. | 359/296 |
| 6,067,185 A | 5/2000 | Albert et al. | 359/296 |
| 6,097,531 A | 8/2000 | Sheridon | 359/296 |
| 6,110,538 A | 8/2000 | Sheridon | 427/457 |
| 6,118,426 A | 9/2000 | Albert et al. | 345/107 |
| 6,120,588 A | 9/2000 | Jacobson | 106/31.16 |
| 6,120,839 A | 9/2000 | Comiskey et al. | 427/213.3 |
| 6,122,094 A | 9/2000 | Silverman | 359/296 |
| 6,124,851 A | 9/2000 | Jacobson | 345/206 |
| 6,128,124 A | 10/2000 | Silverman | 359/296 |
| 6,130,773 A | 10/2000 | Jacobson et al. | 359/296 |
| 6,130,774 A | 10/2000 | Albert et al. | 359/296 |
| 6,147,791 A | 11/2000 | Sheridon | 359/296 |
| 6,162,321 A | 12/2000 | Silverman | 156/276 |
| 6,172,798 B1 | 1/2001 | Albert et al. | 359/296 |
| 6,174,153 B1 | 1/2001 | Sheridon | 425/3 |
| 6,177,921 B1 | 1/2001 | Comiskey et al. | 345/107 |
| 6,197,228 B1 | 3/2001 | Sheridon | 264/1.36 |

FOREIGN PATENT DOCUMENTS

| EP | 942405 | 9/1999 |
|----|--------|--------|
| EP | 1024470 | 8/2000 |
| EP | 070544 | 1/2001 |
| EP | 070545 | 1/2001 |
| JP | 11296111 | 10/1999 |
| JP | 2000187253 | 7/2000 |

OTHER PUBLICATIONS

James T.C. Wojtyk, Peter M. Kazmaier and Erwin Buncel, Effects of Metal Ion Complexation on the Spiropyran–Merocyanine Interconversion: Development of a Thermally Stable Photo–Switch, Chem. Commun., 1998, p. 1703.

U.S. patent application Ser. No. 09/035,518, Sacripante et al., filed Mar. 15, 1998, Attorney Docket No. D/97446, entitle "Flexible Displays".

U.S. patent application Ser. No. 09/723,187, Chopra et al., filed Nov. 27, 2000, Attorney Docket No. D/A0677, entitled "Encapsulation Process".

U.S. patent application Ser. No. 09/749,688, Sheridon, filed Dec. 28, 2000, Attorney Docket No. D/A0673, entitled "Gyricon Display Containing Chemical Absorbents".

U.S. patent application Ser. No. 09/722,565, Biegelsen et al., filed Nov. 28, 2000, Attorney Docket No. D/A0668, entitled Methods of Encapsulating Cores Using Ink Jets or Fogs.

U.S. patent application Ser. No. 09/723,204, Sheridon, filed Nov. 28, 2000, Attorney Docket No. DA0666, entitled "Swollen Gyricon Displays and Method of Making Same".

U.S. patent application Ser. No. 09/757,539, Sheridon, filed Jan. 11, 2001, Attorney Docket No. D/99667, entitled "Rotating Element Sheet Material with Dual Vector Field Addressing".

U.S. patent application Ser. No. 09/757,531, Sheridon, filed Jan. 11, 2001, Attorney Docket No. D/99666, entitled "Rotating Element Sheet Material and Stylus with Gradient Field Addressing".

U.S. patent application Ser. No. 09/440,675, Simoni, filed Nov. 16, 1999, Attorney Docket No. D/99538, entitled Applications for Electronic Reusable Paper.

U.S. patent application Ser. No. 09/749,379, Sheridon, filed Dec. 28, 2000, Attorney Docket No. D/99536, entitled "Method for Making Microencapsulated Gyricon Beads".

U.S. patent application Ser. No. 09/438,894, filed Nov. 12, 1999, Attorney Docket No. D/99535, entitled Field Addressed Displays Using Charge Discharging in Conjunction with Charge Retaining Island Structures.

U.S. patent application Ser. No. 09/360,052, Richley, filed Jul. 23, 1999, Attorney Docket No. D/99235Q, entitled "Method and Apparatus for Fabricating Bichromal Elements".

U.S. patent application Ser. No. 09/360,088, Richley, filed Jul. 23, 1999, Attorney Docket No. D/99235, entitled "Method and Apparatus for Fabricating Bichromal Elements".

U.S. patent application Ser. No. 09/427,346, Torres, filed Oct. 26, 1999, Attorney Docket No. D/99128, entitled "Bichromal Beads Having Electrolytes Therein".

U.S. patent application Ser. No. 09/427,411, Sheridon et al., filed Oct. 26, 1999, Attorney Docket No. D/99128Q1, entitled Biochromal Beads Having Crystalline Materials Therein.

U.S. patent application Ser. No. 09/427,656, Sheridon et al., filed Oct. 26, 1999, Attorney Docket No. D/99128Q, entitled "Bichromal Beads having Charge Adjuvants Therein".

U.S. patent application Ser. No. 09/465,801, Biegelsen, filed Dec. 17, 1999, Attorney Docket No. D/99137, entitled "System and Method for Rotatable Element Assembly and Laminate Substrate Assembly".

U.S. patent application Ser. No. 09/563,504, Knights, filed May 3, 2000, Attorney Docket No. D/99127, entitled "Rotating Element Sheet Material With Microstructured Substrate and Method of Use".

U.S. patent application Ser. No. 09/549,518, Sheridon, filed Apr. 14, 2000, Attorney Docket No. D/99126, entitled "Rotating Element Material With Generalized Containment Structure".

U.S. patent application Ser. No. 09/643,670, Kazmaier, filed Aug. 17, 2000, Attorney Docket No. D/99125, entitled "Electromagnetophotographic Display System and Method".

U.S. patent application Ser. No. 09/517,522, Silverman, filed Mar. 2, 2000, Attorney Docknet No. D/99124, entitled "Rotating Element Sheet Material with Reversible Highlighting".

U.S. patent application Ser. No. 09/216,829, Biegelsen, filed Dec. 21, 1998, Attorney Docket No. D/98453, "Ferrofluidic Electric Paper".

U.S. patent application Ser. No. 09/037,767, Howard et al., filed Mar. 10, 1998, Attorney Docket No. 98095, entitled "Charge Retention Islands for Electric Paper and Applications Thereof".

* cited by examiner

*Primary Examiner*—Ricky Mack
*Assistant Examiner*—Omar Hindi
(74) *Attorney, Agent, or Firm*—Judith L. Byorick

(57) ABSTRACT

Disclosed is a display comprising an arrangement of a plurality of optically anisotropic rotatable elements, each of the rotatable elements having a surface in contact with an enabling fluid, the rotatable elements being electrically dipolar in the presence of the enabling fluid and thus being subject to rotation upon application of an electric field, the rotatable elements being free to rotate in place but not free to translate substantially so as to disrupt the arrangement of rotatable elements, wherein a first portion of the surface contains a mixture of a chelating agent and a spiropyran material of the formula -continued
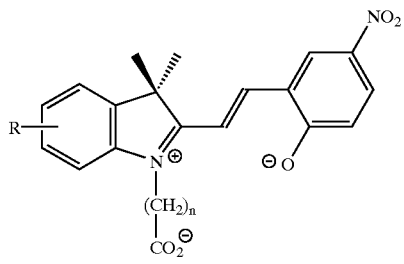
or
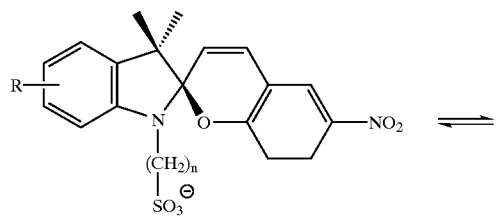
-continued
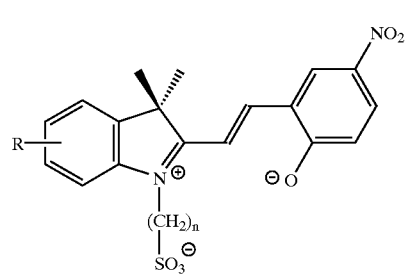
wherein n is an integer representing the number of repeat —CH$_2$— units and R is —H or —CH=CH$_2$, and wherein a second portion of the surface contains substantially no spiropyran.
28 Claims, 5 Drawing Sheets

PHOTOCHROMIC GYRICON DISPLAY

Copending application U.S. Ser. No. 09/864,902 filed concurrently herewith, entitled "Photochromic Electrophoretic Ink Display," with the named inventors Daniel A. Foucher, Raj D Patel, Naveen Chopra, Peter M. Kazmaier, Erwin Buncel, and James Woltyk, the disclosure of which is totally incorporated herein by reference, discloses an electrophoretic ink comprising a suspending fluid and, suspended in the suspending fluid, a plurality of particles comprising a mixture of a chelating agent and a spiropyran material of the formula

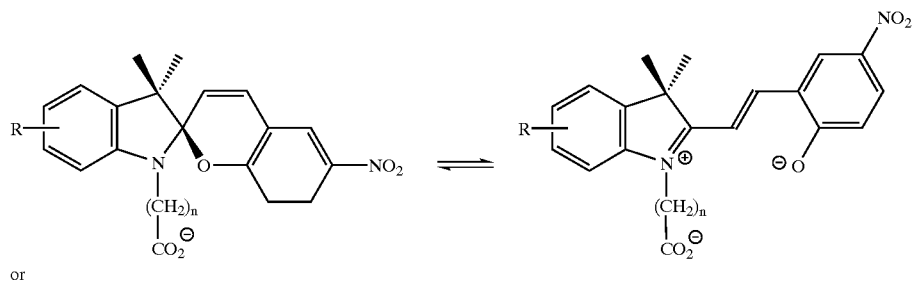

or

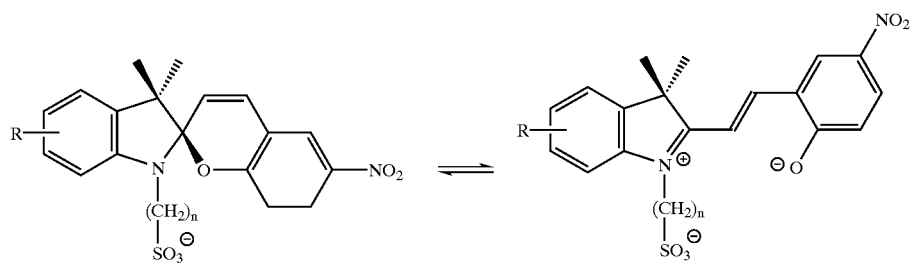

wherein n is an integer representing the number of repeat —$CH_2$— units and R is —H or —CH=$CH_2$, said particles being free to migrate within said suspending fluid under the influence of an electric field.

Copending application U.S. Serial No., now U.S. Pat. No. 6,365,312, filed concurrently herewith, entitled "Marking Particles," with the named inventors Daniel A. Foucher, Raj D. Patel, Naveen Chopra, Peter M. Kazmaier, Erwin Buncel, and James Wojtyk, the disclosure of which is totally incorporated herein by reference, discloses marking particles comprising a first polymer, a second polymer, a chelating agent, and a spiropyran material of the formula

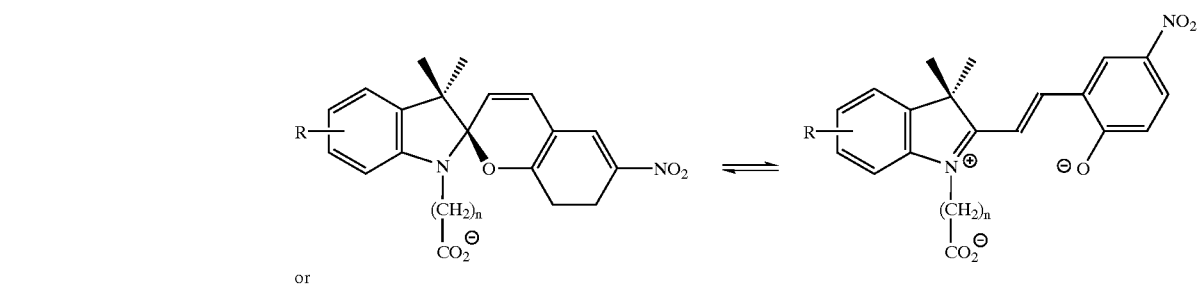

or

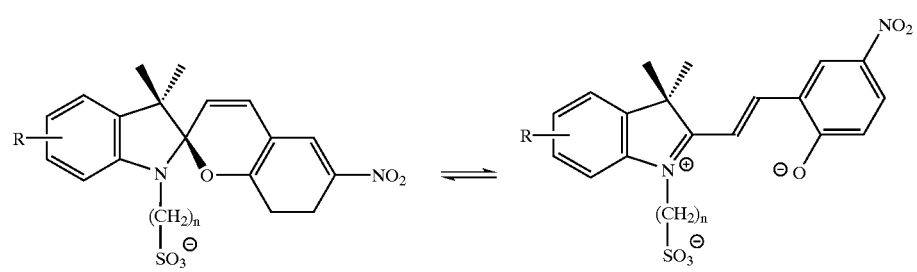

wherein n is an integer representing the number of repeat —$CH_2$— units and R is —H or —$CH=CH_2$. The marking particles comprise a core containing the first polymer in which is dispersed the chelating agent and the spiropyran and encapsulated within a shell of the second polymer formulated by an interfacial polymerization.

Copending application U.S. Serial No., now U.S. Pat. No. 6,358,655, filed concurrently herewith, entitled "Marking Particles," with the named inventors Daniel A. Foucher, Raj D. Patel, Naveen Chopra, and Peter M. Kazmaier, the disclosure of which is totally incorporated herein by reference, discloses marking particles comprising a resin, a chelating agent, and a spiropyran material which is of the formula a gyricon sheet including a binder with rotating elements and dielectric fluid therein, and further including a chemical absorbent in association therewith. The chemical absorbent, such as zeolite or charcoal, absorbs contaminants present in the gyricon sheet that interfere with the reliable operation of the display. The chemical absorbent may be present either in the gyricon sheet itself or in a separate scavenger layer adjacent to and in contact with the gyricon sheet. The presence of the chemical absorbent significantly increases the length of time that the display can reliably display images.

Copending application U.S. Ser. No. 09/722,565, now U.S. Pat. No. 6,406,747, filed Nov. 28, 2000, entitled "Methods of Encapsulating Cores Using Ink Jets or Fogs,"

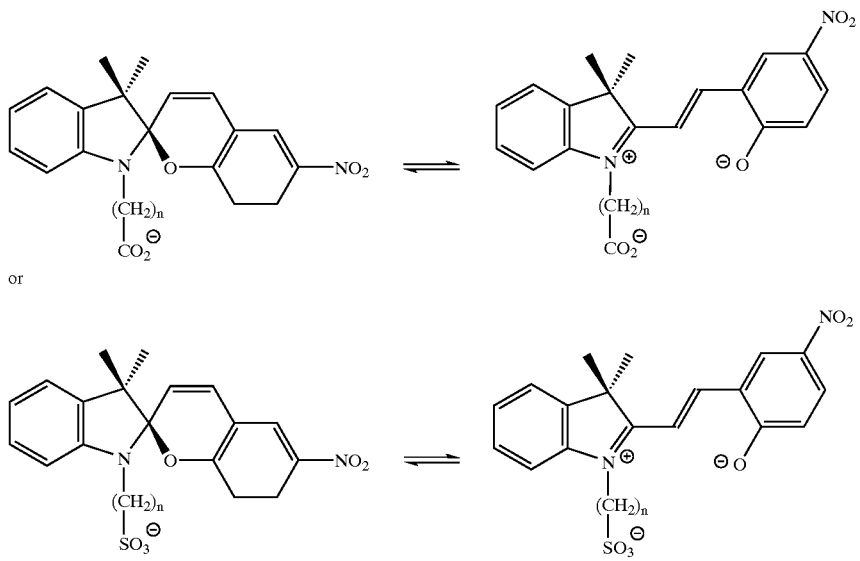

The marking particles are prepared by an emulsion aggregation process.

Copending application U.S. Ser. No. 09/035,518, now U.S. Pat. No. 6,235,195, filed Mar. 15, 1998, entitled "Flexible Displays," with the named inventors Guerino G. Sacripante and James C. Mikkelsen Jr. and published in Japan on Oct. 29, 1999 as Publication No. 11296111, the disclosures of which are totally incorporated herein by reference, discloses a display comprising a first component containing spheres encapsulated within a wax, and thereover and thereunder said component substrates.

Copending application U.S. Ser. No. 09/723,187, now U.S. Pat. No. 6,488,870, filed Nov. 27, 2000, entitled "Encapsulation Process," with the named inventors Naveen Chopra, Peter M. Kazmaier, and Paul J. Gerroir, the disclosure of which is totally incorporated herein by reference, discloses an encapsulation process including: (a) forming an emulsion composed of a continuous phase comprising a first liquid, a cationic material, and an anionic material, and a disperse phase composed of a plurality of droplets of a second liquid, wherein a number of the droplets includes therein one to five particles; and (b) inducing complex coacervation of the cationic material and the anionic material to form a shell around each of the droplets.

Copending application U.S. Ser. No. 09/749,688, now U.S. Pat. No. 6,396,621, filed Dec. 28, 2000, entitled "Gyricon Display Containing Chemical Absorbents," with the named inventor Nicholas K. Sheridon, the disclosure of which is totally incorporated herein by reference, discloses with the named inventors David K. Biegelsen, Naveen Chopra, Karen A. Moffat, and Nicholas K. Sheridon, the disclosure of which is totally incorporated herein by reference, discloses a method of coating a liquid or solid particulate core that involves dropping or suspending the particulate core in an atmosphere and then applying a liquid coating while the particulate core is dropped or suspended, the applying of the liquid coating being done by either (a) spraying the liquid coating onto the particulate core with an ink jet or (b) moving the particulate core through a fog of the liquid coating. In a further embodiment, the method can be used for encapsulating a liquid or solid particulate core within a polymeric shell by dropping or suspending the particulate core in an atmosphere, then applying by one of the above-mentioned methods a first coating composition containing a first reactant to the particulate core while the particulate core is being dropped or suspended, and subsequently exposing the particulate core coated with the first coating composition to a second composition containing a second reactant which reacts with the first reactant, which second composition is immiscible with the first coating composition, whereby the polymeric shell is formed by interfacial polymerization. By these methods, the formation of membranes or polymer shells around a variety of particulate core materials can be done using precise amounts of coating materials, thereby reducing waste and improving efficiencies of the process.

Copending application U.S. Ser. No. 09/723,204, now U.S. Pat. No. 6,441,946, filed Nov. 28, 2000, entitled "Swollen Gyricon Displays and Method of Making Same," with the named inventor Nicholas K. Sheridon, the disclosure of which is totally incorporated herein by reference, discloses a gyricon sheet which includes a binder containing rotating elements, wherein the binder is swollen with dielectric fluids so as to have cavities larger than the rotating elements around each of the rotating elements, the cavities filled with the dielectric fluids, and wherein the dielectric fluids comprise a mixture of at least two liquids having different binder swelling capabilities. By selection of the mixture of dielectric liquids, the extent of swelling of the gyricon sheet can be precisely controlled, enabling the gyricon sheet to exhibit a high level of display brightness.

Copending application U.S. Ser. No. 09/757,539, filed Jan. 11, 2001, entitled "Rotating Element Sheet Material With Dual Vector Field Addressing," with the named inventor Nicholas K. Sheridon, the disclosure of which is totally incorporated herein by reference, discloses a rotating element sheet material comprising a plurality of rotatable elements disposed in a substrate and in contact with an enabling fluid; where one of the plurality of rotatable elements comprises a core configured to present a first aspect in a first orientation and a second aspect in a second orientation, and where the first orientation and the second orientation are related by a rotational transformation about an axis of the rotatable element, and where the rotatable element in contact with the enabling fluid is further configured to exhibit a first addressing dipole configured to couple with a first vector field and a second addressing dipole configured to couple with a second vector field, and where the rotatable element exhibits the first aspect in the first vector field in a first direction and the second aspect in the second vector field in the first direction.

Copending application U.S. Ser. No. 09/757,531, filed Jan. 11, 2001, entitled "Rotating Element Sheet Material and Stylus With Gradient Field Addressing," with the named inventor Nicholas K. Sheridon, the disclosure of which is totally incorporated herein by reference, discloses a kit comprising rotating element sheet material and a gradient field stylus, where the sheet material comprises a plurality of rotatable elements disposed in a substrate and in contact with an enabling fluid, where the substrate comprises a plurality of sheet latching components; where one of the rotatable elements comprises first and second rotatable latching components and a core configured to present a first aspect in a first orientation and a second aspect in a second orientation, related by a rotational transformation about an axis of the rotatable element; and where one of the sheet latching components is proximal to the first rotatable latching component in the first orientation and proximal to the second rotatable latching component in the second orientation; and where the rotatable and sheet latching components exhibit an attractive force based on a first gradient field, and where a distal end of the gradient field stylus exhibits an attractive force with the rotatable latching components based on a second gradient field.

Copending application U.S. Ser. No. 09/440,675, filed Nov. 16, 1999, entitled "Applications for Electronic Reusable Paper," with the named inventors Helen M. Simoni and Bryan T. Preas and published in Canada on May 16, 2001 as Publication No. 2320417, the disclosures of which are totally incorporated herein by reference, discloses a system for displaying information which comprises a substrate and a conformable display media and control logic associated with the substrate. The display media has an input for receiving display information and the control logic provides display information to the display media through the display media input. The system may also contain other elements which interact with the control logic and the display media such as sensors, speakers, buttons, lights and an interface for communicating with the control circuitry.

Copending application U.S. Ser. No. 09/749,379, filed Dec. 28, 2000, entitled "Method for Making Microencapsulated Gyricon Beads," with the named inventors Nicholas K. Sheridon, Nassim Khonsari, and Naveen Chopra, the disclosure of which is totally incorporated herein by reference, discloses a method for making microencapsulated gyricon beads comprising the steps of converging first, second, third, and fourth materials in a liquid state; forming a bead from the first and second materials, the bead having two hemispheric surfaces with one surface differing from the other in optical and electrical characteristics; surrounding the bead with the third material; encapsulating the third material with the fourth material, and solidifying the fourth material.

Copending application U.S. Ser. No. 09/438,894, now U.S. Pat. No. 6,456,272, filed Nov. 12, 1999, entitled "Field Addressed Displays Using Charge Discharging in Conjunction With Charge Retaining Island Structures," with the named inventors Matthew E. Howard and Edward A. Richley, the disclosure of which is totally incorporated herein by reference, discloses an electric reusable paper sheet that uses a pattern of conductive charge-retaining islands on the outward-facing side of the first of two thin layers used to encapsulate an electric reusable paper substrate which interact with conductive areas in the encapsulating sheet. The second encapsulating layer may also be coated with a conductive material, or made of a conductive material, and may or may not be patterned. The electric reusable paper substrate and two encapsulating layers comprise a sheet of gyricon electric reusable paper on which images can be written and erased repeatedly. The patterned charge-retaining islands of the first encapsulating layer receive electric charges from an external charge-transfer device. After the charge-transfer device is removed, the conductive, charge-retaining islands hold electric charge, creating an electric field in the electric reusable paper sufficient to cause an image change.

Copending application U.S. Ser. No. 09/360,052, now abandoned, filed Jul. 23, 1999, entitled "Method and Apparatus for Fabricating Bichromal Elements," with the named inventor Edward A. Richley and published in Europe on Jan. 24, 2001 as Publication No. 070545, the disclosures of which are totally incorporated herein by reference, discloses an apparatus for fabricating bichromal elements which has a separator member having a central rotating point comprising first and second spaced apart, opposed surfaces with an edge region in contact with both of the opposed surfaces. The apparatus further includes an apparatus for dispensing first and second differently colored hardenable liquids substantially at the central rotating point of the first and second surfaces, respectively, and an apparatus for substantially uniformly spreading the liquid material over the first and second surfaces toward said edge region to form a reservoir of liquid material outboard of said edge region which is comprised of side-by-side regions of the first and second differently colored hardenable liquids, and for forming ligaments from the reservoir.

Copending application U.S. Ser. No. 09/360,088, now U.S. Pat. No. 6,485,280, filed Jul. 23, 1999, entitled "Method and Apparatus for Fabricating Bichromal Elements," with the named inventor Edward A. Richley and published in Europe on Jan. 24, 2001 as Publication No. 070544, the disclosures of which are totally incorporated herein by reference, discloses an apparatus for fabricating bichromal elements comprising a separator member having a central rotating point, the separator member having first and second spaced apart, opposed surfaces with an edge region in contact with both of said opposed surfaces. The spacing between the opposed surfaces varies with the distance outwardly from the central rotating point such that the spacing is the largest at the central rotating point and the spacing decreases outwards from the central rotating point and the spacing is a minimum at the edge region. Further each of the opposed surfaces has a substantially annular cup spaced apart from and substantially surrounding the central rotating point. The apparatus for fabricating bichromal elements also includes apparatus for dispensing first and second differently colored hardenable liquids in the cups of the first and second surfaces, respectively, and an apparatus for substantially uniformly spreading the liquid material in the annular cups located in the first and second surfaces and for substantially uniformly spreading the liquid material from the cups over the first and second surfaces toward said edge region to form a reservoir of liquid material outboard of said edge region, and for forming ligaments from said reservoir.

Copending application U.S. Ser. No. 09/427,346, now U.S. Pat. No. 6,335,818, filed Oct. 26, 1999, entitled "Bichromal Beads Having Electrolytes Therein," with the named inventor Francisco E. Torres, the disclosure of which is totally incorporated herein by reference, discloses a display medium and display apparatus with a substrate, and bichromal beads having an electrolyte and a polymer, wherein the bichromal beads are dispersed or contained in the substrate.

Copending application U.S. Ser. No. 09/427,411, now U.S. Pat. No. 6,496,298, filed Oct. 26, 1999, entitled "Bichromal Beads Having Charge Adjuvants Therein," with the named inventors Nicholas K. Sheridon and Ron Swidler, the disclosure of which is totally incorporated herein by reference, discloses a display medium with an encapsulant medium, and bichromal beads having a charge adjuvant, wherein the bichromal beads are dispersed or contained in the encapsulant medium.

Copending application U.S. Ser. No. 09/427,656, now U.S. Pat. No. 6,362,915, filed Oct. 26, 1999, entitled "Bichromal Beads Having Crystalline Materials Therein," with the named inventors Nicholas K. Sheridon, Edward A. Richley, and James Mikkelsen, the disclosure of which is totally incorporated herein by reference, discloses a display medium with an encapsulant medium, and bichromal beads having a crystalline material, wherein the bichromal beads are dispersed or contained in the encapsulant medium.

Copending application U.S. Ser. No. 09/465,801, now U.S. Pat. No. 6,440,252, filed Dec. 17, 1999, entitled "System and Method for Rotatable Element Assembly and Laminate Substrate Assembly," with the named inventors David K. Biegelsen, Joseph Crowley, and Alexander E. Silverman, the disclosure of which is totally incorporated herein by reference, discloses methods and systems used to assemble composite rotatable-element components and used to form a laminate substrate system, and use a plurality of rotatable-element components or rotatable-element component material of two classes. Each class is defined by a common response or responses to incident electromagnetic radiation of interest. The method for assembling a composite rotatable-element component comprises: dispersing a plurality of rotatable-element components of a first class to first preferred positions on a first carrier; dispersing a plurality of rotatable-element components of a second class to second preferred positions on a second carrier; performing a first manipulation of the first carrier and the second carrier such that one of the plurality of rotatable-element components of a first class and one of the plurality of rotatable-element components of a second class touch at a first contact point; and performing a second manipulation of the rotatable-element components that touch such that they bond to form a composite rotatable-element component. The method for assembling a laminate substrate further comprises: performing a third manipulation of the first carrier and the second carrier such that they touch at a set of second contact points; and performing a fourth manipulation of the first carrier and the second carrier such that they bond to form the laminate substrate.

Copending application U.S. Ser. No. 09/563,504, now U.S. Pat. No. 6,504,525 filed May 3, 2000, entitled "Rotating Element Sheet Material With Microstructured Substrate and Method of Use," with the named inventor John C. Knights, the disclosure of which is totally incorporated herein by reference, discloses systems comprising rotating element sheet material with a microstructured substrate component, and a method of assembling such rotating element sheet material. A first embodiment comprises a substrate, enabling fluid, a plurality of rotatable elements of a first class, and a plurality of rotatable elements of a second class, where the substrate comprises a cavity-containing matrix having a plurality of cavities of a first class and a plurality of cavities of a second class, where the plurality of rotatable elements of a first class are disposed within the plurality of cavities of a first class, and the plurality of rotatable elements of a second class are disposed within the plurality of cavities of a second class, and where the plurality of cavities of a first class and the plurality of cavities of a second class are arranged in a regular, repeating pattern in a substantially single layer, or alternatively, the plurality of cavities of a first class and the plurality of cavities of a second class are arranged to define macroscopic regions displaying common aspects. A further embodiment includes a method of macroscopically addressing rotating element sheet material.

Copending application U.S. Ser. No. 09/549,518, now U.S. Pat. No. 6,498,674, filed Apr. 14, 2000, entitled "Rotating Element Sheet Material With Generalized Containment Structure," with the named inventor Nicholas K. Sheridon, the disclosure of which is totally incorporated herein by reference, discloses rotating element sheet material with a generalized containment structure and methods of fabricating such rotating element sheet material, where the rotating element sheet material comprises a fibrous matrix, a plurality of rotatable elements, and an enabling fluid, and where the plurality of rotatable elements are disposed within the fibrous matrix and are in contact with the enabling fluid. In addition, rotating element sheet material with a generalized containment structure, and methods of fabricating such rotating element sheet material, includes rotating element sheet material which comprises a fibrous matrix and a plurality of micro-capsules, and where the micro-capsules define a hollow space therein, and the hollow space contains a subset of a plurality of rotatable elements and an enabling fluid, and where the plurality of micro-cavities are disposed within the fibrous matrix.

Copending application U.S. Ser. No. 09/643,670, filed Aug. 17, 2000, entitled "Electromagnetophotographic Display System and Method," with the named inventors Peter M. Kazmaier, Hadi K. Mahabadi, Jaan Noolandi, James H. Sharp, and Francisco E. Torres, the disclosure of which is totally incorporated herein by reference, discloses an electromagnetophoretic ink material for use as electronic and magnetic display elements. In particular, the invention relates to the preparation and use of microencapsulated aspect elements having both an electrostatic layer and a magnetic layer, and that can be addressed to produce a display aspect by the application of external electric fields and external magnetic fields.

Copending application U.S. Ser. No. 09/517,522, filed Mar. 2, 2000, entitled "Rotating Element Sheet Material With Reversible Highlighting," with the named inventor Alexander E. Silverman, the disclosure of which is totally incorporated herein by reference, discloses a kit comprising rotating element sheet material, a highlighting implement, and an erasing implement, a binder, and a method of use. The rotating element sheet material comprises a plurality of first rotatable elements and a plurality of second rotatable elements disposed in a substrate. Each first rotatable element in the plurality has a first collection of responses to incident electromagnetic radiation of interest. One response in the first collection renders the first rotatable element transparent-clear to incident electromagnetic energy of interest, and a second response renders the first rotatable element opaque to incident electromagnetic energy of interest. The first rotatable element also exhibits a first work function. Likewise, each second rotatable element has a second collection of responses to incident electromagnetic radiation of interest. A first response in the second collection renders the second rotatable element transparent-clear to the incident electromagnetic energy of interest. A second response renders the second rotatable element transparent-colored to the incident electromagnetic energy of interest. The second rotatable elements also exhibit a second work function that is less than the first work function. The addressing implement introduces a vector field in a first direction in the substrate where the vector field has a magnitude greater than the second work function and less than the first work function. In addition, the erasing implement introduces a vector field in a second direction in the substrate where the vector field has a magnitude greater than the second work function and less than the first work function. The binder is configured to accommodate the rotating element sheet material, the highlighting implement, and the erasing implement.

Copending application U.S. Ser. No. 09/216,829, now U.S. Pat. No. 6,284,352, filed Dec. 21, 1998, entitled "Ferrofluidic Electric Paper," with the named inventors David K. Biegelsen and Warren B. Jackson and published in Japan on Jul. 4, 2000 as Publication No. 2000187253, the disclosures of which are totally incorporated herein by reference, discloses a low cost, reusable electric paper that uses ferrofluidic colored fluids and an external magnetic writing instrument. The paper can be formed from laminated rolls of polymeric media that are roller die cut, inked, aligned, bonded, and cut to an appropriate size. The paper is formed from layers that define a hidden reservoir and a visible reservoir for each of an array of print cells that form a grid on the paper. A ferrofluidic coloring fluid is permanently contained within the paper and can move from the hidden reservoir to the visible reservoir. The size of the cells define the resolution of the paper. Initially, the paper appears white. However, after passing a writing instrument, such as a stylus, over desired print cells, these cells switch from a first hidden bistable state to a second visible bistable state. In the second visible bistable state, the ferrofluidic coloring fluid forms a desired image in a desired color or colors.

Copending application U.S. Ser. No. 09/037,767, now U.S. Pat. No. 6,222,513, filed Mar. 10, 1998, entitled "Charge Retention Islands for Electric Paper and Applications Thereof," with the named inventors Matthew E. Howard, Robert A. Sprague, and Edward A. Richley and published in Europe on Sep. 15, 1999 as Publication No. 942405, the disclosure of which is totally incorporated herein by reference, discloses an electric paper sheet that uses a pattern of conductive charge-retaining islands on the outward-facing side of the first of two thin layers used to encapsulate a gyricon sheet. The second encapsulating layer may also be coated with a conductive material, or made of a conductive material, and may or may not be patterned. The gyricon sheet and two encapsulating layers comprise a sheet of gyricon electric paper on which images can be written and erased repeatedly. The patterned charge-retaining islands of the first encapsulating layer receive electric charges from an external charge-transfer device. After the charge-transfer device is removed, the conductive, charge-retaining islands hold electric charge, creating an electric field in the electric paper sufficient to cause an image change.

Copending application U.S. Ser. No. 09/199,473, now U.S. Pat. No. 6,211,998, filed Nov. 25, 1998, entitled "Magnetic Unlatching and Addressing of a Gyricon Display," with the named inventor Nicholas K. Sheridon, the disclosure of which is totally incorporated herein by reference, discloses a method of addressing a sheet of a rotating element sheet material that has a reduced applied electric field requirement when a gyricon sheet using magnetic trapping. A magnetic trapping gyricon sheet comprises a substrate with a plurality of rotatable elements disposed in the substrate. The elements comprise at least two portions, each portion having an associated optical modulation characteristic and the optical modulation characteristics of at least one portion are different from the optical modulation characteristic of at least one other portion. Importantly, one portion is magnetized, and the element also has an anisotropy for providing an electrical dipole moment. The electrical dipole moment renders the element electrically responsive such that when the rotating element is rotatably disposed in an electric field while the electrical dipole moment of the element is provided, the element tends to rotate to an orientation in which the electrical dipole moment aligns with the field. A small additional magnet is associated with each of the elements. When the magnetized portion of the element is the portion of the element nearest the additional magnet a magnetic attractive force will exist between the additional magnetized means and the magnetized portion of the element. A magnetic field is applied to the sheet in the vicinity of at least one of the rotatable elements and its associated magnet to reduce the magnetic attractive force therebetween. When the magnetic field has been reduced then applying a reduced electric field in the vicinity of at least one rotatable element will cause the rotatable element to align with the electric field.

Copending application U.S. Ser. No. 09/199,818, now U.S. Pat. No. 6,251,329, filed Nov. 25, 1998, entitled "Magnetic Unlatching and Addressing of a Gyricon Display," with the named inventor Nicholas K. Sheridon, the disclosure of which is totally incorporated herein by reference, discloses a method of making rotating element sheet material utilizing magnetic latching. First a plurality of rotating elements having a magnetized segment are mixed with magnetic particles to attract the magnetic particles to the magnetized segments. Then the rotating elements with the attached magnetic particles are mixed with a liquid elastomer. A magnetic field is applied to orient the rotating elements in a common direction. When the rotating elements and the attached magnetic particles have all been oriented the elastomer is cured to form an elastomer substrate with trapped rotating elements and magnetic particles. The elastomer substrate is then immersed into a bath of dielectric plasticizer which is absorbed more readily by elastomer than by the rotating elements. The elastomer substrate swells to create plasticizer-filled voids around the rotating elements.

The magnetic particles remain incorporated within the elastomer to form magnetic material pads which are associated with an element.

Copending application U.S. Ser. No. 09/200,553, filed Nov. 25, 1998, entitled "Gyricon Displays Utilizing Magnetic Elements and Magnetic Trapping," with the named inventor Nicholas K. Sheridon, the disclosure of which is totally incorporated herein by reference, discloses a sheet material for use in a gyricon display in which a rotatable element, which has a portion which is capable of being permanently magnetized, may be oriented to experience either an attractive force or a repelling force between itself and another magnetized element. The attractive force between the element and the pad serve to latch the element in place and prevent unwanted display changes from taking place while the repellant force serves to trap the element in place for the same reasons. The element may be constructed to be either cylindrically or spherically shaped. Further, the sheet material may also contain soft magnetic material pads which may be arranged to provide multiple latching states as desired, Copending application U.S. Ser. No. 09/199,544, now U.S. Pat. No. 6,262,707, filed Nov. 25, 1998, entitled "Gyricon Displays Utilizing Magnetic Addressing and Latching Mechanisms," with the named inventor Nicholas K. Sheridon, the disclosure of which is totally incorporated herein by reference, discloses a rotating element for use in an electric paper system in which the rotating element may be either substantially cylindrical or substantially spherical in shape and comprises at least three portions. Each portion has an associated optical modulation characteristic and the optical modulation characteristics of at least one portion are different from the optical modulation characteristics of at least one other portion. One of the portions is capable of being permanently magnetized. The rotating element also has an anisotropy for providing an electrical dipole moment. The electrical dipole moment renders the element electrically responsive such that when the rotating element is rotatably disposed in an electric field while the electrical dipole moment of the rotating element is provided, the rotating element tends to rotate to an orientation in which the electrical dipole moment aligns with the field.

Copending application U.S. Ser. No. 09/770,430, filed Jan. 26, 2001, entitled "Rotation and Threshold Mechanism for Twisting Ball Display," with the named inventor Edward A. Richley, the disclosure of which is totally incorporated herein by reference, discloses a rotation mechanism for bichromal balls in a twisting ball display based on electrostatic induction. A bichromal ball with hemispherically differentiated electrical time constants is immersed in a dielectric liquid containing a charge director solution. The liquid is contained within an encapsulant. The charge director solution has positive and negative ions with substantially different mobilities. Space charge clouds created in this fluid upon application of an electric field act so as to induce polarization differently in each hemisphere, leading to a net dynamic polarization. Interaction between the space charge and the induced polarization serves to rotate the ball. Ions are subsequently trapped at the fluid/encapsulant interface due to greater polarizability of the encapsulant. A threshold is obtained by the excess field needed to release the ions and so reverse the ion motion.

Copending application U.S. Ser. No. 09/239,293, now U.S. Pat. No. 6,303,211, filed Jan. 29, 1999, entitled "Tamper-Evident Electric Paper," with the named inventors Jock D. Mackinlay, Daniel G. Bobrow, Daniel H. Green, L. Charles Hebel, Nicholas K. Sheridon, Craig A. Smith, and William C. Emerson and published in Europe on Aug. 2, 2000 as Publication No. 1024470, the disclosures of which are totally incorporated herein by reference, discloses tamper-evident electric paper made of two sheets of electric paper bonded together, the bottom sheet of which includes a pattern. Any attempt to erase a writing on the top sheet of electric paper results in the pattern on the bottom sheet of electric paper being erased. Therefore any tampering by erasure of a writing on the tamper-evident electric paper is revealed by the absence of a portion of the pattern on the bottom sheet of electric paper. Single sheet tamper-evident electric paper has a complex pattern, such as an encryption, printed on a single sheet of electric paper. Any attempt to erase a writing on the electric paper also erases a portion of the encryption, thereby providing evidence of tampering.

Copending application U.S. Ser. No. 09/335,205, now U.S. Pat. No. 6,421,035, filed Jun. 17, 1999, entitled "Fabrication of a Twisting Ball Display Having Two or More Different Kinds of Balls," with the named inventors Nicholas K. Sheridon, Jock D. Mackinlay, and Maureen C. Stone, the disclosure of which is totally incorporated herein by reference, discloses a method of making a substrate in which sets of optically anisotropic spheroidal balls are disposed, as for use in an electrical twisting ball display. First and second sets of spheroidal balls are deposited on a receiving surface composed of an elastomer substrate material in an adhesive state, the spheroidal balls thus deposited adhering to the receiving surface. Balls of the first and second sets are physically distinguishable from one another. Balls of the first set can be deposited in a first arrangement, and balls of the second set, in a second arrangement. Each ball of each set has an optical anisotropy and an anisotropy for providing an electrical dipole moment, the electrical dipole moment rendering the ball electrically responsive such that when the ball is rotatably disposed in an electric field while the electrical dipole moment of the ball is provided, the ball tends to rotate to an orientation in which the electrical dipole moment aligns with the field. With the balls thus deposited, additional liquid elastomer material is poured over the balls adhering to the receiving surface, thereby covering the balls and forming an uncured substrate material in which the balls are disposed. This uncured substrate material is cured to form a substrate in which balls of the first and second sets are disposed. A plasticizer fluid can be applied to the substrate thus formed, thereby expanding the substrate so as to render the balls disposed in the substrate rotatable within the substrate.

Copending application U.S. Ser. No. 08/960,865, now U.S. Pat. No. 6,428,868, filed Oct. 30, 1997, entitled "Twisting Cylinder Display," with the named inventors Nicholas K. Sheridon and Joseph Crowley and published in Canada on Dec. 27, 1998 as Publication No. 2228920, the disclosures of which are totally incorporated herein by reference, discloses a gyricon or twisting-particle display based on nonspherodial (e.g. substantially cylindrical) optically anisotropic particles disposed in a substrate. The particles can be either bichromal or polychromal cylinders, preferably aligned parallel to one another and packed close together in a monolayer. A rotatable disposition of each particle is achievable while the particle is thus disposed in the substrate; for example, the particles can already be rotatable in the substrate, or can be rendered rotatable in the substrate by a nondestructive operation performed on the substrate. In particular, the substrate can be made up of an elastomer that is expanded by application of a fluid thereto so as to render the particles rotatable therein. A particle, when in its rotatable disposition, is not attached to the substrate. The close-packed monolayer configuration of particles provides excellent brightness characteristics and relative ease of manufacture as compared with certain other high-brightness gyricon displays. The substrate containing the cylinders can be fabricated with the swelled-elastomer techniques known from spherical-particle gyricon displays, with a simple agitation process step being used to align the cylinders within the sheeting material. Techniques for fabricating the cylinders are also disclosed.

BACKGROUND OF THE INVENTION

The present invention is directed to a display. More specifically, the present invention is directed to a display having photochromic characteristics. One embodiment of the present invention is directed to a display comprising an arrangement of a plurality of optically anisotropic rotatable elements, each of said rotatable elements having a surface in contact with an enabling fluid, said rotatable elements being electrically dipolar in the presence of the enabling fluid and thus being subject to rotation upon application of an electric field, said rotatable elements being free to rotate in place but not free to translate substantially so as to disrupt the arrangement of rotatable elements, wherein a first portion of said surface contains a mixture of a chelating agent and a spiropyran material of the formula

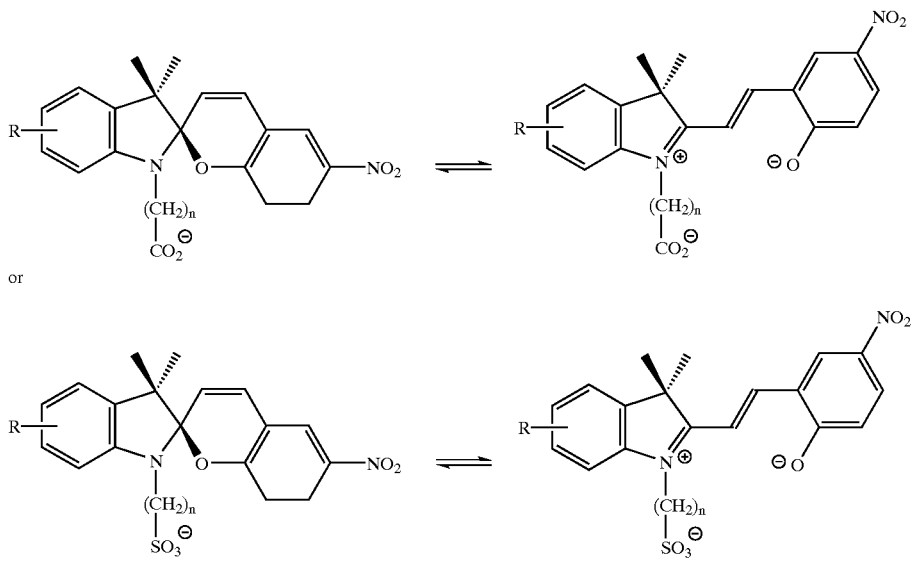

wherein n is an integer representing the number of repeat —$CH_2$— units and R is —H or —$CH=CH_2$, and wherein a second portion of said surface contains substantially no spiropyran.

Photochromism in general is a reversible change of a single chemical species between two states having distinguishably different absorption spectra, wherein the change is induced in at least one direction by the action of electromagnetic radiation. The inducing radiation, as well as the changes in the absorption spectra, are usually in the ultraviolet, visible, or infrared regions. In some instances, the change in one direction is thermally induced. The single chemical species can be a molecule or an ion, and the reversible change in states may be a conversion between two molecules or ions, or the dissociation of a single molecule or ion into two or more species, with the reverse change being a recombination of the two or more species thus formed into the original molecule or ion. Photochromic phenomena are observed in both organic compounds, such as anils, disulfoxides, hydrazones, oxazones, semicarbazones, stilbene derivatives, o-nitrobenzyl derivatives, spiro compounds, and the like, and in inorganic compounds, such as metal oxides, alkaline earth metal sulfides, titanates, mercury compounds, copper compounds, minerals, transition metal compounds such as carbonyls, and the like. Photochromic materials are known in applications such as photochromic glasses, which are useful as, for example, ophthalmic lenses.

Electric reusable paper can be defined as any electronically addressable display medium that approximates paper in form and function. Electric reusable paper ideally is light-weight, thin, and flexible, and ideally it displays images indefinitely while consuming little or no power. In addition, electric reusable ideally is reusable so that the user is able to erase images and create new ones repeatedly. Preferably, electric reusable paper displays images using reflected light and allows a very wide viewing angle.

One form of electric paper uses a gyricon or rotating element display. Gyricon or twisting ball displays typically are display systems in which the display panel comprises rotatable elements such as cylinders, prisms, or spherical balls that have an optical and an electrical anisotropy as a result of each hemisphere surface having a different color and a electrical charge in contact with a liquid. These rotatable elements are typically embedded in a solid substrate and a slight space between each rotatable element and the substrate is filled with a liquid so that the elements are free to rotate in a changing electrical field but cannot migrate from one location to another. If, for example, one hemisphere of the rotatable element is black and the other is white, each pixel can be turned on and off by the electrical field applied to that location. Each pixel can be individually addressed, and a full page image can thus be generated.

Most commonly the solid substrate used in these displays is a gel, typically a silicone gel. The purpose of using this material lies in the remarkably large expansion in volume exhibited by gels when soaked in certain liquids refered to as plasticizing liquids. Thirty percent expansions are not uncommon when these materials are soaked in silicone oils. The rotatable elements do not expand when contacted by the plasticizing liquid, so a cavity opens up around each rotatable element when the gel is immersed in a plasticizing liquid. This space fills with the plasticizing liquid.

Other variations on these displays are also known, such as embodiments wherein the rotatable elements are individually enclosed in shells with the space between the inner surface of the shell and the outer surface of the rotatable element being filled with a dielectric liquid. The resultant capsules can then be dispersed in a second liquid, such as an optically clear epoxy, which can then be hardened. The resultant display is then in the form of a thin, paper-like sheet. Alternatively, the resultant display can easily be conformally coated on a non-planar surface for even greater flexibility of applications.

Other variations on these displays include using rotatable elements of other than ball or sphere shape, such as cylinders, prisms, or the like.

In some embodiments, the display comprises a thin substantially transparent sheet having many of the attributes of paper documents. It looks like paper, has ambient light valve behavior like paper (i.e. the brighter the ambient light, the more easily it may be seen), is flexible like paper, can be folded like paper, can be carried around like paper, can be written on like paper, can be copied like paper, and has nearly the archival memory of paper since the display typically retains an image indefinitely in the absence of an applied electric field. These embodiments are frequently referred to as "electric paper". The display provides a reuseable (and thus environmentally friendly) substitute for ordinary paper. In other embodiments, the display device has a rigid structure incorporating an array of addressing electrodes. Upon application of an electrical field between electrodes located on opposite surfaces of the layer containing the bichromal elements, the elements rotate depending on the polarity of the field, presenting one or the other hemisphere to an observer.

U.S. Pat. No. 5,633,109 (Jennings et al.), the disclosure of which is totally incorporated herein by reference, discloses an ink composition which comprises an aqueous liquid vehicle, a photochromic material, and a vesicle-forming lipid, wherein vesicles of the lipid are present in the ink.

U.S. Pat. No. 5,593,486 (Oliver et al.), the disclosure of which is totally incorporated herein by reference, discloses a hot melt ink composition comprising (a) an ink vehicle, said ink vehicle being a solid at about 25° C. and having a viscosity of from about 1 to about 20 centipoise at a temperature suitable for hot melt ink jet printing, said temperature being greater than about 45° C., (b) a photochromic material, (c) an optional colorant, and (d) an optional propellant.

U.S. Pat. No. 5,551,973 (Oliver et al.), the disclosure of which is totally incorporated herein by reference, discloses an ink composition which comprises an aqueous phase, an oil phase, a photochromic material, and a surfactant, said ink exhibiting a liquid crystalline gel phase at a first temperature and a liquid microemulsion phase at a second temperature higher than the first temperature.

U.S. Pat. No. 5,759,729 (Martin et al.), the disclosure of which is totally incorporated herein by reference, discloses a toner composition for the development of electrostatic latent images which comprises particles comprising a mixture of a resin and a photochromic material. Another embodiment of the present invention is directed to a liquid developer composition for the development of electrostatic latent images which comprises a nonaqueous liquid vehicle and a photochromic material, wherein the liquid developer has a resistivity of from about $10^8$ to about $10^{11}$ ohm-cm and a viscosity of from about 25 to about 500 centipoise. Yet another embodiment of the present invention is directed to a liquid developer composition for the development of electrostatic latent images which comprises a nonaqueous liquid vehicle, a charge control agent, and toner particles comprising a mixture of a resin and a photochromic material.

U.S. Pat. No. 5,710,420 (Martin et al.), the disclosure of which is totally incorporated herein by reference, discloses a method of embedding and recovering machine readable information on a substrate which comprises (a) writing data in a predetermined machine readable code format on the substrate with a photochromic marking material having a first state corresponding to a first absorption spectrum and a second state corresponding to a second absorption spectrum; and (b) thereafter effecting a photochromic change in at least some of the photochromic marking material from the first state to the second state.

James T. C. Wojtyk, Peter M. Kazmaier, and Erwin Buncel, "Effects of Metal Ion Complexation on the Spiropyran-Merocyanine Interconversion: Development of a Thermally Stable Photo-Switch," *Chem. Commun.* 1998, p. 1703, the disclosure of which is totally incorporated herein by reference, discloses spectrophotometric absorption and fluorescence measurements of spiropyrans

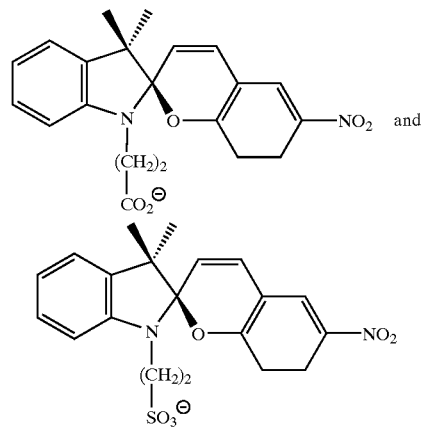

modified with chelating functionalities, in the presence of $Ca^{2+}$ and $Zn^{2+}$, that provide evidence of a thermally stable spiropyran-merocyanine photoswitch that is modulated by the metal cations.

U.S. Pat. No. 4,126,854 (Sheridon), the disclosure of which is totally incorporated herein by reference, discloses a display system in which the display panel comprises a plurality of particles which have an electrical anisotropy due to hemispherical surface coatings of different Zeta potential and their distribution in a volume of a dielectric liquid, and which also have an optical anisotropy due to the hemispherical surface coatings having different optical characteristics which may be due to the color or other optical properties of the hemispherical coatings. Under the action of an external electric field, the particles will rotate in accordance with their electrical anisotropy to provide a display in accordance with their optical anisotropy. The display has switching threshold and memory capabilities.

U.S. Pat. No. 4,143,103 (Sheridon), the disclosure of which is totally incorporated herein by reference, discloses a method of making a display characterized by a plurality of particles which have an electrical anisotropy due to hemispherical surface coatings of different Zeta potential and their distribution in a volume of a dielectric liquid and which also have an optical anisotropy due to the hemispherical surface coatings having different optical characteristics. The particles are mixed with a light transparent liquid which is subsequently cured to form an elastomeric or rigid slab. Following curing of the liquid, the slab is emersed in a plasticizer (dielectric liquid) which is absorbed by the slab and which causes the slab to expand slightly. Expansion of the slab around the particles provides a plasticizer-filled cavity around each particle which cavities allow the particles to rotate to provide a display in accordance with their optical anisotropy but does not allow substantial translation of the particles.

U.S. Pat. No. 4,261,653 (Goodrich), the disclosure of which is totally incorporated herein by reference, discloses a light valve formed of a plurality of spherical dipolar particles suspended in a matrix material. Each spherical dipolar particle has a unified body formed in three discrete symmetrical sections. A central section is configured to permit light transmission when in a first orientation with respect to a path of light travel, and generally not permit light transmission when in a second, transverse orientation with respect to the path of light travel. A pair of intermediate sections bound the central section and are formed of a transparent material having an electrical permittivity that varies through a range of values as a function of the frequency of an applied electric field. A pair of outer sections bounds the intermediate sections and are formed of a material having a relatively stable electrical permittivity within the range of values of the intermediate sections. An applied electric field at one frequency extreme will cause the spherical dipolar particle to align in the first orientation to permit light transmission, and an applied electric field in the other frequency extreme will cause the particle to anti-align in the second, transverse orientation to shutter or reflect light. The matrix material is preferably formed of a plasticized elastomer that has a plurality of expanded cavities, with each cavity containing an outer lubricating layer to allow free rotational motion of a dipolar particle in the cavity. The use of a light valve of the present invention and method of manufacturing the spherical dipolar particle construction are also disclosed.

U.S. Pat. No. 4,438,160 (Ishikawa et al.), the disclosure of which is totally incorporated herein by reference, discloses a method for manufacturing rotary ball display devices wherein a plurality of such balls are provided with a coating of a color different from the remainder of the ball, the ball members are coated with a thin coating insoluble in the settling medium into which they are introduced, so that upon settling into a low viscosity liquid, they form a uniform layer. A high molecular weight hardenable coating material which is soluble in the low viscosity liquid is then poured onto the coated ball members to cover the layer. Then, the low viscosity liquid is removed and the hardenable coating material is caused to harden. The thin coating is then dissolved away from portions of the ball members to leave cavity portions thereabout into which a high resistivity liquid is introduced, The resulting ball members have a refractive index on the colored layer which is substantially the same as the refractive index of the high resistivity liquid contained in the cavities.

U.S. Pat. No. 5,389,945 (Sheridon), the disclosure of which is totally incorporated herein by reference, discloses an addressable display system including a paper-like sheet comprising a light transparent host layer loaded with a plurality of repositionable elements, the elements are movable from a first orientation in which they will present a first visual appearance, to a second orientation in which they will present a second visual appearance, and independent external addressing means relatively movable with respect to the display sheet for affecting the orientation of the repositionable elements.

U.S. Pat. No. 5,604,027 (Sheridon), the disclosure of which is totally incorporated herein by reference, discloses bichromal balls having two hemispheres, typically one black and one white, each having different electrical properties. Each ball is enclosed within a spherical shell and then a space between the ball and shell is filled with a liquid to form a microsphere so that the ball is free to rotate in response to an electrical field. The microspheres can then be mixed into a substrate which can be formed into sheets or can be applied to any kind of surface. The result is a film which can form an image from an applied electrical field.

U.S. Pat. No. 5,989,629 (Sacripante et al.), the disclosure of which is totally incorporated herein by reference, discloses a process for the preparation of bichromal spheres comprising (i) preparing monochromal spheres by the aggregation and coalescence of an emulsion resin with a first colorant and inorganic salt; (ii) contacting the resulting monochromal spheres with an oxidizing agent, followed by a polymerization with a vinyl monomer and a free radical initiator; (iii) forming a monolayer of the resulting monochromal spheres on a substrate; and (iv) subjecting the resulting monochromal spheres to a vapor thermal deposition with a second colorant dissimilar than the first colorant thereby to coat one hemisphere of each of said monochromal spheres, thereby resulting in bichromal spheres with dissimilar colors.

U.S. Pat. No. 4,810,431 (Leidner), the disclosure of which is totally incorporated herein by reference, discloses a particle display comprising a plurality of particles which in an electrical field rotate to expose either their white or black surface depending upon the polarity of the field. The particle display can be used for a flat panel ambient-illuminated numeric, alpha-numeric and other forms of visual displays.

U.S. Pat. No. 5,262,098 (Crowley et al.), the disclosure of which is totally incorporated herein by reference, discloses an apparatus for fabricating hemispherically bichromal balls, comprising a separator member having opposing first and second surfaces located and an edge region in contact with both surfaces, and delivery means for flowing first and second colored hardenable liquid material over the first and second surfaces, respectively, so that the liquid materials arrive at the edge at substantially the same flow rate and form a reservoir outboard of the edge region. The reservoir comprises side-by-side regions of different colors which do not intermix. Further means is provided for propelling the first and second liquid materials away from the separator member and out of the reservoir into a fluid medium as a plurality of side-by-side bichromal streams whose forward ends become unstable and break up into droplets which form into spherical balls, each of the balls comprising hemispheres of differently colored hardenable liquid, and means for collecting the bichromal balls.

U.S. Pat. No. 5,344,594 (Sheridon), the disclosure of which is totally incorporated herein by reference, discloses a method of forming hemispheric bichromal balls, including the steps of bringing together two streams of differently colored hardenable liquids for forming a single side-by-side bichromal stream, expelling said single side-by-side bichromal stream into a fluid as one or more free jets whose forward ends becomes unstable and break up into droplets which form into spherical balls, each of the balls comprising hemispheres of differently colored hardenable liquid, and finally hardening the balls.

U.S. Pat. No. 5,917,646 (Sheridon), the disclosure of which is totally incorporated herein by reference, discloses a combination of an optically transmissive dielectric fluid having a first refractive index and an optically anisotropic particle rotatably disposed in the fluid. The particle has at least one optically transmissive region having a second refractive index. The particle provides a first optical modulation characteristic when disposed in the fluid in a first orientation with respect to a flux of optical energy, and further provides a second optical modulation characteristic when disposed in the fluid in a second orientation with respect to a flux of optical energy. The particle has an anisotropy for providing an electrical dipole moment, the electrical dipole moment rendering the particle electrically responsive such that when the particle is rotatably disposed in an electric field while the electrical dipole moment of the particle is provided, the particle tends to rotate to an orientation in which the electrical dipole moment aligns with the field. For example, the disposition of the particle in the fluid can give rise to the electrical dipole moment of the particle. The fluid-particle combination can be used to make a gyricon or rotating-particle display in which each rotatable particle (e.g., spherical ball) in the display acts as a lens.

U.S. Pat. No. 5,777,782 (Sheridon), the disclosure of which is totally incorporated herein by reference, discloses a gyricon or rotating-particle display having an auxiliary optical structure. The display includes a substrate with an optically transmissive window, a plurality of particles disposed in the substrate, and an optical focusing element optically coupled to the window. Each particle has an anisotropy for providing an electrical dipole moment, the electrical dipole moment rendering the particle electrically responsive such that when the particle is rotatably disposed in an electric field while the electrical dipole moment of the particle is provided, the particle tends to rotate to an orientation in which the electrical dipole moment aligns with the field. A rotatable disposition of each particle is achievable while the particle is thus disposed in the substrate, when the particle is in this rotatable disposition, it is not attached to the substrate. Each particle, when rotatably disposed in the substrate, is disposable in first and second rotational orientations with respect to the optically transmissive window. Each particle provides a first optical modulation characteristic when disposed in its first orientation with respect to a flux of optical energy through the window, and further provides a second optical modulation characteristic when disposed in its second orientation with respect to a flux of optical energy through the window, The optical focusing element can be optically refractive; for example, it can include an array of converging lenses, such as a "fly's-eye" array of microlenses. In this case, the particles can be disposed in an array that is registered with the lens array.

U.S. Pat. No. 5,815,306 (Sheridon et al.), the disclosure of which is totally incorporated herein by reference, discloses a gyricon or rotating-particle display having an "eggcrate" substrate. The display includes a substrate having a cavity-containing matrix whose cavities are disposed substantially in a single layer and are arranged within the matrix substantially in a geometrically regular pattern, and a plurality of optically anisotropic particles disposed in the cavities in the substrate, with each cavity containing at most one of the optically anistropic particles. A rotatable disposition of each particle is achievable while the particle is thus disposed in the substrate; the particle, when in its rotatable disposition, is not attached to the substrate. Each particle, for example, can have an anisotropy for providing an electrical dipole moment, the electrical dipole moment rendering the particle electrically responsive such that when the particle is rotatably disposed in an electric field while the electrical dipole moment of the particle is provided, the particle tends to rotate to an orientation in which the electrical dipole moment aligns with the field. The single layer of cavities can be substantially planar, and the geometrical pattern of cavities can be a two-dimensional array pattern in the plane of the layer, such as a hexagonal, rectangular, or rhomboidal array pattern. The substrate can further include first and second members between which members the matrix is disposed; at least one of the members can include an optically transmissive window through which a flux of optical energy can pass so as to be incident on the particles.

U.S. Pat. No. 5,717,514 (Sheridon), the disclosure of which is totally incorporated herein by reference, discloses a multisegmented ball for an electrical twisting ball display device made up of spheroidal balls rotatably disposed in an elastomer substrate. The ball is composed of segments arrayed substantially parallel to one another, each segment being adjacent to at least one other segment and to no more than two other segments, adjacent segments being adjoined to one another at substantially planar interfaces. The segments include a first segment having a first thickness and a first optical modulation characteristic, a second segment having a second thickness and a second optical modulation characteristic, and a third segment having a thickness different from at least one of the first and second thicknesses and an optical modulation characteristic different from at least one of the first and second optical modulation characteristics. The ball has an anisotropy for providing an electrical dipole moment, the electrical dipole moment rendering the ball electrically responsive such that when the ball is rotatably disposed in a nonoscillating electric field while the electrical dipole moment of the ball is provided, the ball tends to rotate to an orientation in which the electrical dipole moment aligns with the field. A method and apparatus for fabricating the ball are also disclosed.

U.S. Pat. No. 5,919,409 (Sheridon), the disclosure of which is totally incorporated herein by reference, discloses a method of fabricating a multisegmented ball for an electrical twisting ball display device, which is made up of spheroidal balls rotatably disposed in an elastomer substrate. The ball is composed of segments arrayed substantially parallel to one another, each segment being adjacent to at least one other segment and to no more than two other segments, adjacent segments being adjoined to one another at substantially planar interfaces. The method for fabricating the multisegmented spheroidal balls comprises the steps of first providing a multiplicity of liquid flows, each liquid flow having an associated flow rate, each liquid flow being a flow of a hardenable liquid material associated with an optical modulation characteristic. The multiplicity of flows are then merged into a combined liquid flow where each one of the plurality of liquid flows is joined to at least one other of the plurality of liquid flows at a planar interface. After forming a combined liquid flow, a ligament is formed from the combined liquid flow and a plurality of spheroidal balls are formed from the ligament, each of the balls comprising a multiplicity of segments where each one of the multiplicity of segments is joined to at least one other of the multiplicity of segments at a planar interface. After the balls are formed they are hardened.

U.S. Pat. No. 5,891,479 (Sheridon), the disclosure of which is totally incorporated herein by reference, discloses an apparatus for fabricating a multisegmented ball for an electrical twisting ball display device, which is made up of spheroidal balls rotatably disposed in an elastomer substrate.

The ball is composed of segments arrayed substantially parallel to one another, each segment being adjacent to at least one other segment and to no more than two other segments, adjacent segments being adjoined to one another at substantially planar interfaces. The apparatus has a plurality of separator members, each separator member having two opposed surfaces and an edge region in contact with both of said surfaces. A liquid flow is associated with each separator member and one of the surfaces on the separator member. Each one of the liquid flows is provided across its associated separator members toward the edge region of the separator member. Each of the liquid flows is of a hardenable liquid material and has an optical modulation characteristic and a flow rate. The apparatus also has apparatus for merging the liquid flows outboard of the edge regions of the separator members into a combined liquid flow and then apparatus for forming a ligament from the combined liquid flow. Apparatus for forming a plurality of spheroidal balls from the ligament; and apparatus for hardening the balls thus formed complete the apparatus.

U.S. Pat. No. 5,708,525 (Sheridon), the disclosure of which is totally incorporated herein by reference, discloses a multisegmented ball for an electrical twisting ball display device made up of spheroidal balls rotatably disposed in an elastomer substrate. The ball is composed of segments arrayed substantially parallel to one another. Each segment is adjacent to at least one other segment and to no more than two other segments, adjacent segments being adjoined to one another at substantially planar interfaces. Each segment has an optical modulation characteristic, the optical modulation characteristics of adjacent segments being different from one another. The segments of the ball include a first exterior segment, a second exterior segment, and a transparent interior segment. The ball has an anisotropy for providing an electrical dipole moment, the electrical dipole moment rendering the ball electrically responsive such that when the ball is rotatably disposed in a nonoscillating electric field while the electrical dipole moment of the ball is provided, the ball tends to rotate to an orientation in which the electrical dipole moment aligns with the field, Also disclosed are: a material made up of a substrate in which are disposed the aforementioned balls; an apparatus made up of a piece of this material, together with electrodes to facilitate a rotation of balls rotatably disposed therein; and a method for using this apparatus.

U.S. Pat. No. 5,717,515 (Sheridon), the disclosure of which is totally incorporated herein by reference, discloses a method for producing a canted electric field for an electrical twisting ball display device made up of electrically and optically anisotropic spheroidal balls rotatably disposed in a substrate. The display has an array of addressable elements, each array element including at least one spheroidal ball. According to the method, an array element is selected. A preferred direction of orientation is selected for balls of the selected array element, the direction of orientation forming an angle with a vector normal to a planar portion of the substrate surface in a vicinity of the selected array element, the angle being greater than 0 degree and less than 180 degrees. Balls of the selected array element are aligned with the preferred direction of orientation by applying an electric field in the vicinity of the selected array element, the electric field having an electric field vector oriented parallel to the selected preferred direction, thereby causing balls of the selected array element to rotate so as to align with the preferred direction of orientation, Also disclosed are: an electrode assembly for addressing a twisting ball display, capable of producing an electric field adjustable as to the direction of orientation of the field over a continuous angular range of directions, and a twisting ball apparatus incorporating this electrode assembly.

U.S. Pat. No. 5,760,761 (Sheridon), the disclosure of which is totally incorporated herein by reference, discloses a multisegmented, highlight color ball for an electrical twisting ball display device made up of spheroidal balls rotatably disposed in an elastomer substrate. The ball is composed of segments arrayed substantially parallel to one another, each segment being adjacent to at least one other segment and to no more than two other segments, adjacent segments being adjoined to one another at substantially planar interfaces. Each segment has an optical modulation characteristic, the optical modulation characteristics of adjacent segments being different from one another. The segments include: a central segment having a thickness; a first interior segment, situated adjacent to the central segment and having a thickness less than the central segment thickness; a second interior segment, situated opposite the first interior segment with respect to the central segment and having a thickness less than the central segment thickness; a first exterior segment; and a second exterior segment. The central segment can be of a background color; the first interior segment can be of a foreground color; the second interior segment can be of a highlight color; and the exterior segments can be transparent. The ball has an anisotropy for providing an electrical dipole moment, the electrical dipole moment rendering the ball electrically responsive such that when the ball is rotatably disposed in a nonoscillating electric field while the electrical dipole moment of the ball is provided, the ball tends to rotate to an orientation in which the electrical dipole moment aligns with the field. Also disclosed are: an apparatus made up of a substrate in which are disposed the aforementioned balls, together with electrodes to facilitate a rotation of balls rotatably disposed therein; and a method for using this apparatus.

U.S. Pat. No. 5,751,268 (Sheridon), the disclosure of which is totally incorporated herein by reference, discloses a seven-segment ball for an electrical twisting ball display device made up of spheroidal balls rotatably disposed in an elastomer substrate. The device built with the seven-segment balls can provide, for example, two fully saturated colors, two partially saturated colors, and a background color, such as white. The ball is composed of seven segments arrayed substantially parallel to one another, each segment being adjacent to at least one other segment and to no more than two other segments, adjacent segments being adjoined to one another at substantially planar interfaces. The seven segments include a transparent central segment, transparent first and second exterior segments, and four colored interior segments, two on each side of the central segment. For example, the first, second, third, and fourth interior segments can each have different colors such as red, black, blue, and green. The ball has an anisotropy for providing an electrical dipole moment, the electrical dipole moment rendering the ball electrically responsive such that when the ball is rotatably disposed in an electric field while the electrical dipole moment of the ball is provided, the ball tends to rotate to an orientation in which the electrical dipole moment aligns with the field. Also disclosed are: an apparatus made up of a substrate in which are disposed the aforementioned balls, together with electrodes to facilitate a rotation of balls rotatably disposed therein; and a method for using this apparatus.

U.S. Pat. No. 5,892,497 (Robertson), the disclosure of which is totally incorporated herein by reference, discloses a segmented ball for an electrical twisting ball color display device, the device being composed of different sets of spheroidal balls rotatably disposed in an elastomer substrate, each set being associated with a different display color. The segmented ball includes a colored interior segment surrounded on either side by transparent exterior segments, the three segments being arrayed substantially parallel to one another, with adjacent segments being adjoined to one another at substantially planar interfaces. The colored interior segment can have, for example, a transparent or opaque chromatic color, such as red, green, or blue. The ball has an anisotropy for providing an electrical dipole moment, the electrical dipole moment rendering the ball electrically responsive such that when the ball is rotatably disposed in a nonoscillating electric field while the electrical dipole moment of the ball is provided, the ball tends to rotate to an orientation in which the electrical dipole moment aligns with the field. Also disclosed are: a material made up of a substrate in which are disposed two or more different sets of the aforementioned balls, each set having a different center-segment color so as to provide a different observable display color; an apparatus made up of a piece of this material, together with electrodes to facilitate a rotation of balls rotatably disposed therein; and a method for using this apparatus.

U.S. Pat. No. 5,767,826 (Sheridon et al.), the disclosure of which is totally incorporated herein by reference, discloses a multilayer substrate material for a subtractive-color electrical twisting ball display. The material is composed of a layered substrate including first, second, and third layers, each layer of the substrate being a nearest neighboring layer with respect to at least one other layer and no more than two other layers. Spheroidal balls are disposed in each of the first, second, and third layers. In the first layer, each ball has at least two component regions including a component region having a first chromatic color, such as transparent cyan. In the second layer, each ball has at least two component regions including a component region having a second chromatic color, such as transparent magenta. In the third layer, each ball has at least two component regions including a component region having a third chromatic color, such as transparent yellow. Optionally, the substrate can further include a fourth layer in which are disposed spheroidal balls, each having at least two component regions including a black component region. Each ball in each layer has an anisotropy for providing an electrical dipole moment, the electrical dipole moment rendering the ball electrically responsive such that when the ball is rotatably disposed in a nonoscillating electric field while the electrical dipole moment of the ball is provided, the ball tends to rotate to an orientation in which the electrical dipole moment aligns with the field. Also disclosed are a twisting-ball apparatus made with the material, and a method for using this apparatus.

U.S. Pat. No. 5,739,801 (Sheridon), the disclosure of which is totally incorporated herein by reference, discloses a multithreshold electrical twisting ball display device. The device is composed of electrically and optically anisotropic spheroidal balls of at least two different rotation thresholds, disposed in an elastomer substrate, together with an addressing electrode assembly. The addressing electrode assembly allows a preferred region of the substrate to be selected in which at least one ball of the first set and at least one ball of the second set are disposed, and first and second electric fields to be applied to the preferred region thus selected, each of the first and second electric fields extending throughout the preferred region. The first field facilitates a contemporaneous rotation of balls of both the first and second sets rotatably disposed in the preferred region. The second electric field facilitates a rotation of balls of the second set rotatably disposed in the preferred region, without facilitating a rotation of any ball of the first set rotatably disposed in the preferred region. Also disclosed are the substrate material and electrode assembly for the device, and a method of using the device.

U.S. Pat. No. 5,982,346 (Sheridon et al.), the disclosure of which is totally incorporated herein by reference, discloses a method of making a substrate in which sets of optically anisotropic spheroidal balls are disposed, as for use in an electrical twisting ball display. First and second sets of spheroidal balls, are deposited on a receiving surface composed of an elastomer substrate material in an adhesive state, the spheroidal balls thus deposited adhering to the receiving surface. Balls of the first and second sets are physically distinguishable from one another. Balls of the first set can be deposited in a first arrangement, and balls of the second set, in a second arrangement. Each ball of each set has an optical anisotropy and an anisotropy for providing an electrical dipole moment, the electrical dipole moment rendering the ball electrically responsive such that when the ball is rotatably disposed in an electric field while the electrical dipole moment of the ball is provided, the ball tends to rotate to an orientation in which the electrical dipole moment aligns with the field. With the balls thus deposited, additional, liquid elastomer material is poured over the balls adhering to the receiving surface, thereby covering the balls and forming an uncured substrate material in which the balls are disposed. This uncured substrate material is cured to form a substrate in which balls of the first and second sets are disposed. A plasticizer fluid can be applied to the substrate thus formed, thereby expanding the substrate so as to render the balls disposed in the substrate rotatable within the substrate.

U.S. Pat. No. 5,737,115 (Mackinlay et al.), the disclosure of which is totally incorporated herein by reference, discloses a tristate light valve ball for an electrical twisting ball device composed of spheroidal balls rotatably disposed in an elastomer substrate. The ball is composed of segments arrayed substantially parallel to one another, each segment being adjacent to at least one other segment and to no more than two other segments. Adjacent segments are adjoined to one another at substantially planar interfaces. The segments include: a first, interior, nontransparent segment having a first optical modulation characteristic; a second exterior, transparent segment, adjacent to the first segment and having a second optical modulation characteristic; a third, interior, nontransparent segment having a third optical modulation characteristic; and a fourth, exterior, transparent segment adjacent to the third segment. For example, the ball can be made with a black first segment adjacent to a white third segment, surrounded on either side by clear second and fourth exterior segments. The ball has an anisotropy for providing an electrical dipole moment, the electrical dipole moment rendering the ball electrically responsive such that when the ball is rotatably disposed in a nonoscillating electric field while the electrical dipole moment of the ball is provided, the ball tends to rotate to an orientation in which the electrical dipole moment aligns with the field. Also disclosed are: a material made up of a substrate layer in which are disposed the aforementioned balls, with a colored backing joined to a rear surface of the layer; and a method for using a device incorporating the balls.

U.S. Pat. No. 5,754,332 (Crowley), the disclosure of which is totally incorporated herein by reference, discloses a gyricon or twisting-ball display having superior reflectance characteristics comparing favorably with those of white paper. The display is based on a material made up of optically anisotropic particles, such as bichromal balls, disposed substantially in a monolayer in a substrate. The particles are closely packed with respect to one another in the monolayer, preferably so that adjacent particle surfaces are as close to one another as possible. A rotatable disposition of each particle is achievable while the particle is thus disposed in the substrate; for example, the particles can already be rotatable in the substrate, or can be rendered rotatable in the substrate by a nondestructive operation performed on the substrate. In particular, the particles can be situated in an elastomer substrate that is expanded by application of a fluid thereto so as to render the particles rotatable therein. A particle, when in its rotatable disposition, is not attached to the substrate. A reflective-mode display apparatus can be constructed from a piece of the material together a mechanism (e.g., addressing electrodes) for facilitating rotation of at least one of the particles. The light reflected from the display is reflected substantially entirely from the monolayer of balls, so that lower layers are not needed. By eliminating the lower layers, the display can be made thinner, which in turn provides further advantages, such as lower drive voltage and better resolution due to better control of fringing fields.

U.S. Pat. No. 5,808,783 (Crowley), the disclosure of which is totally incorporated herein by reference, discloses a gyricon or twisting-ball display having superior reflectance characteristics comparing favorably with those of white paper. The display is based on a material made up of optically anisotropic particles, such as bichromal balls, disposed in a substrate having a surface. The particles situated closest to the substrate surface form substantially a single layer. Each particle in the layer has a center point, no particle in the layer being disposed entirely behind the center point of any nearest neighboring particle in the layer with respect to the substrate surface. Each particle in the layer has a projected area with respect to the substrate surface. Particles of the set are sufficiently closely packed with respect to one another in the layer that the union of their projected areas exceeds two-thirds of the area of the substrate surface. A rotatable disposition of each particle is achievable while the particle is thus disposed in the substrate; for example, the particles can already be rotatable in the substrate, or can be rendered rotatable in the substrate by a nondestructive operation. In particular, the particles can be situated in an elastomer substrate that is expanded by application of a fluid thereto so as to render the particles rotatable therein. A particle, when in its rotatable disposition, is not attached to the substrate. A reflective-mode display apparatus can be constructed from a piece of the material together with a mechanism (e.g., addressing electrodes) for facilitating rotation of at least one of the particles.

U.S. Pat. No. 5,914,805 (Crowley), the disclosure of which is totally incorporated herein by reference, discloses a gyricon or twisting-ball display having superior reflectance characteristics comparing favorably with those of white paper is based on a material made up of two populations (e.g., two different sizes) of optically anisotropic particles, such as bichromal balls, disposed in a substrate. Particles of the first population, as considered by themselves without the particles of the second population, are disposed in the substrate in a closely packed (e.g., geometrically regular) arrangement having interstices. Particles of the second population are disposed in the interstices of the arrangement. A rotatable disposition of each particle is achievable while the particle is thus disposed in the substrate; for example, the particles can already be rotatable in the substrate, or can be rendered rotatable in the substrate by a nondestructive operation performed on the substrate. In particular, the particles can be situated in an elastomer substrate that is expanded by application of a fluid thereto so as to render the particles rotatable therein. A particle, when in its rotatable disposition, is not attached to the substrate. A reflective-mode display apparatus can be constructed from a piece of the material together with a mechanism (e.g., addressing electrodes) for facilitating rotation of at least one of the particles.

U.S. Pat. No. 5,825,529 (Crowley), the disclosure of which is totally incorporated herein by reference, discloses a gyricon or twisting-ball display in which optically anisotropic particles, such as bichromal balls, are disposed directly in a working fluid, such as a dielectric liquid, without an elastomer substrate or other cavity-containing matrix. The display apparatus has an optically transmissive viewing surface, behind which the working fluid is disposed with the particles in it. The particles are arranged in a closely packed stable arrangement in which neighboring particles tend to keep one another in place. For example, the particles can be arranged in a hexagonally packed monolayer. The working fluid does not substantially constrain the particles to remain in the stable arrangement, notwithstanding the direct contact of the fluid with the particles.

U.S. Pat. No. 6,147,791 (Sheridon), the disclosure of which is totally incorporated herein by reference, discloses a sheet material for use in a gyricon display in which a rotatable element, which has a portion which is capable of being permanently magnetized may be oriented to experience an attractive force between itself and a soft magnetic material pad. The attractive force between the element and the pad serve to latch the element in place and prevent unwanted display changes from taking place. The element may be constructed to be either cylindrically or spherically shaped. The element and the soft magnetic material pads may be arranged to provide multiple latching states as desired.

U.S. Pat. No. 6,097,531 (Sheridon), the disclosure of which is totally incorporated herein by reference, discloses a method of forming magnetized rotating elements for a rotating element display where all the elements are magnetized in the same orientation is provided. First, at least two planar streams of hardenable liquids flowing in substantially the same direction are provided. Each stream has an associated optical modulation characteristic and at least one stream has an associated optical modulation characteristic different from at least one other stream. At least one stream includes a magnetic pigment. The streams are then merged to form a reservoir containing side-by-side amounts of each liquid from each stream. A free jet is then formed containing side-by-side amounts of each liquid from the reservoir, Then a portion of the free jet is passed through a magnetic field which is oriented transverse to the direction of the free jet to magnetize the magnetic pigment. The rotating elements formed can be either spherical in shape or cylindrical in shape. In either case, each element will comprise side-by-side segments. To form spherical elements the free jet can be broken into spherical portions either before or after the magnetic pigment has been magnetized. Ultimately, magnetized spherical portions of the free jet are hardened into rotating spherical elements and collected. To form cylindrical elements, the free jet is magnetized and hardened into a filament. The filament is then collected and broken into cylindrical elements.

U.S. Pat. No. 6,174,153 (Sheridon), the disclosure of which is totally incorporated herein by reference, discloses an apparatus for forming magnetized rotating elements for a rotating element display where all the elements are magnetized in the same orientation is disclosed. The apparatus comprises at least one separator member. Each separator member has a diameter, two opposed surfaces and an edge region in contact with both of the surfaces. Further included is an apparatus for providing at least two liquid flows wherein each one of the liquid flows has an associated separator member and an associated surface on the associated separator member, and each one of the liquid flows is provided across the associated surface of the associated separator members. The liquid flow flows toward the edge region of the associated separator member. The liquid flows are each a flow of hardenable liquid material associated with an optical modulation characteristic, and at least one of the liquid flows containing a magnetic pigment. The separator members are spun and the liquid flows are merged outboard of the edge regions of the one separator members to form a reservoir containing side-by-side amounts of each liquid. When the flow rate of the liquids is high enough, a free jet approximately in a plane outward from the reservoir, the free jet comprising side-by-side amounts of each liquid from the reservoir is formed. A magnetic field, is provided outward from the formation of the free jet and at least a portion of the free jet is passed through the magnetic field to magnetize the magnetic pigment. The magnetic field is aligned transverse to the free jet. If cylindrical elements are desired then the magnetized free jet is hardened into filaments which can be separated into cylindrical elements. If spherical elements are desired then the free jet is broken up into spherical elements before hardening.

U.S. Pat. No. 6,110,538 (Sheridon), the disclosure of which is totally incorporated herein by reference, discloses a method of making rotating element sheet material utilizing magnetic latching. The first step is providing a sheet of sheet material comprising a substrate with a surface and rotatable elements disposed therein. The elements each have an optical and electrical anisotropy, and comprise at least two portions. One of the portions is magnetizable. After the magnetizable portions have been oriented in a common direction, they are magnetized substantially uniformly. The elements can be oriented such that the magnetized portions are disposed towards the surface of the substrate. A layer of hardenable mixture containing a plurality of magnetic particles is then applied to the surface of the substrate. The hardenable liquid is kept liquid for a period of time to allow the migration magnetic particles to the area of the layer in the vicinity of the magnetized portions of the rotatable elements. Then the hardenable liquid is solidified to trap the magnetic particles in said layer in the area of the layer in the vicinity of the magnetized portion of the rotatable elements to form a magnetic pad.

U.S. Pat. No. 6,038,059 (Silverman), the disclosure of which is totally incorporated herein by reference, discloses several variations in full-color additive gyricons are shown. Each gyricon shown has been designed for ease of construction by eliminating the need for precise placement of rotating elements, alignment between the gyricon layers, if any, and alignment between the gyricon sheet and the addressing device.

U.S. Pat. No. 6,122,094 (Silverman), the disclosure of which is totally incorporated herein by reference, discloses several variations in full-color additive gyricons. Each gyricon shown has been designed for ease of construction by eliminating the need for precise placement of rotating elements, alignment between the gyricon layers, if any, and alignment between the gyricon sheet and the addressing device.

U.S. Pat. No. 6,162,321 (Silverman), the disclosure of which is totally incorporated herein by reference, discloses several variations in full-color additive gyricons. Each gyricon shown has been designed for ease of construction by eliminating the need for precise placement of rotating elements, alignment between the gyricon layers, if any, and alignment between the gyricon sheet and the addressing device.

U.S. Pat. No. 6,128,124 (Silverman), the disclosure of which is totally incorporated herein by reference, discloses several variations in full-color additive gyricons. Each gyricon shown has been designed for ease of construction by eliminating the need for precise placement of rotating elements, alignment between the gyricon layers, if any, and alignment between the gyricon sheet and the addressing device.

U.S. Pat. No. 6,197,228 (Sheridon), the disclosure of which is totally incorporated herein by reference, discloses a method of making rotating element sheet material utilizing magnetic latching. First a plurality of rotating elements, each element having a magnetized segment, are mixed with an elastomer and a plurality of magnetic particles to attract the magnetic particles to the magnetized segments. Then a magnetic field is applied to orient the elements in a common direction. When the rotating elements have all been oriented in a common direction, they are held in that orientation for a long enough period of time to allow the magnetic particles to migrate in the elastomer to the regions of the elastomer in the vicinity of the magnetized segments of the elements. The elastomer is then cured to form an elastomer substrate with trapped rotating elements and magnetic particles. The elastomer substrate is then immersed into a bath of dielectric plasticizer which is absorbed more readily by elastomer than by the rotating elements. The elastomer substrate swells to create plasticizer-filled voids around the rotating elements. The magnetic particles remain incorporated within the elastomer to form magnetic material pads which are associated with an element.

U.S. Pat. No. 6,055,091 (Sheridon et al.), the disclosure of which is totally incorporated herein by reference, discloses a gyricon or twisting-particle display based on nonspheroidal (e.g., substantially cylindrical) optically anisotropic particles disposed in a substrate. The particles can be bichromal cylinders, preferably aligned parallel to one another and packed close together in a monolayer. A rotatable disposition of each particle is achievable while the particle is thus disposed in the substrate; for example, the particles can already be rotatable in the substrate, or can be rendered rotatable in the substrate by a nondestructive operation performed on the substrate. In particular, the substrate can be made up of an elastomer that is expanded by application of a fluid thereto so as to render the particles rotatable therein. A particle, when in its rotatable disposition, is not attached to the substrate. The close-packed monolayer configuration of particles provides excellent brightness characteristics and relative ease of manufacture as compared with certain other high-brightness gyricon displays. The substrate containing the cylinders can be fabricated with the swelled-elastomer techniques known from spherical-particle gyricon displays, with a simple agitation process step being used to align the cylinders within the sheeting material. Techniques for fabricating the cylinders are also disclosed.

U.S. Pat. No. 5,894,367 (Sheridon), the disclosure of which is totally incorporated herein by reference, discloses an electric type paper display having memory properties, rapid response times, and multi-optical optical property display with an image of high quality. Each display element is wholly in contact with liquid in a cavity and the surface of each display element has a portion with a most positive charge. When an electrical field is applied from the outside, each display element is turned correspondingly to the direction of the electric field and, then electrically migrated through the liquid and attached to the inner surface of the cavity. Among multiple display surfaces of each display element an optical property is selected according to an image signal and is visible through a transparent support to an observer. Afterwards, the attached state of each display element, i.e., its display state is held by the action of an attraction force such as van der Waals force and electrostatic force acting between the circumferential surface of the display element and the inner surface of the cavity, even after the electric field is removed.

U.S. Pat. No. 5,922,268 (Sheridon), the disclosure of which is totally incorporated herein by reference, discloses an electric type paper display having memory properties, rapid response times and multi-optical property display with an image of high quality. Each display element is wholly in contact with liquid in a cavity and the surface of each display element has a portion with a most positive charge. When an electrical field is applied from the outside, each display element is turned correspondingly to the direction of the electric field and, then electrically migrated through the liquid and attached to the inner surface of the cavity. Among multiple display surfaces of each display element an optical property is selected according to an image signal and is visible through a transparent support to an observer. Afterwards, the attached state of each display element, i.e., its display state is held by the action of an attraction force such as van der Waals force and electrostatic force acting between the circumferential surface of the display element and the inner surface of the cavity, even after the electric field is removed.

U.S. Pat. No. 5,904,790 (Sheridon), the disclosure of which is totally incorporated herein by reference, discloses an electric type paper display having memory properties, rapid response times and multi-optical property display with an image of high quality is made. Each display element is wholly in contact with liquid in a cavity and the surface of each display element has a portion with a most positive charge. When an electrical field is applied from the outside, each display element is turned correspondingly to the direction of the electric field and, then electrically migrated through the liquid and attached to the inner surface of the cavity. Among multiple display surfaces of each display element an optical property is selected according to an image signal and is visible through a transparent support to an observer. Afterwards, the attached state of each display element, i.e., its display state is held by the action of an attraction force such as van der Waals force and electrostatic force acting between the circumferential surface of the display element and the inner surface of the cavity, even after the electric field is removed.

Sheridon, "The Gyricon—A Twist Ball Display," Proceedings of the Society of Information Display, Vol, 18/3 and 4 (1977), the disclosure of which is totally incorporated herein by reference, discloses a gyricon ambient light viewed display consisting of an elastomer sheet contained between transparent electrodes. The elastomer sheet changes from black to white or from white to black depending upon the polarity of the electrical field that is impressed between the electrodes. The elastomer sheet contains a high loading of small balls that are black on one hemisphere and white on the other. Each ball is contained in an individual oil-filled spherical cavity and is free to rotate in response to the applied electric field.

U.S. Pat. No. 3,612,758 (Evans et al.), the disclosure of which is totally incorporated herein by reference, discloses a color display device employing the electrophoretic migration of color pigment particles to form an image on a matrix addressable panel. One coordinate terminal is connected to a line reservoir containing electrophoretic ink particles of a given polarity while the other coordinate terminal is connected to a transparent conductor. The panel is viewed through the transparent conductor side in ambient illumination.

U.S. Pat. No. 5,930,026 (Jacobson et al.), the disclosure of which is totally incorporated herein by reference, discloses an electrophoretic display which has a substantially two-dimensional arrangement of microcapsules each having therein an electrophoretic composition of a dielectric fluid and a suspension of particles that visually contrast with the dielectric liquid and also exhibit surface charges; a pair of electrodes, at least one of which is visually transparent, disposed on and covering opposite sides of the microcapsule arrangement; and means for creating a potential difference between the two electrodes, the potential difference causing the particles to migrate toward one of the electrodes. The display may be powered by one or more piezoelectric elements, which are also suitable for powering other types of nonemissive displays.

U.S. Pat. No. 5,961,804 (Jacobson et al.), the disclosure of which is totally incorporated herein by reference, discloses an application-ready electrophoresis material includes a carrier and a dispersion of microcapsules therein, the microcapsules each containing a plurality of phases therein. At least some of the phases contrast visually and and exhibit differential responsiveness to an electric field, such that application of the field determines the visual appearance of the microcapsules. The material exhibits stability such the visual appearance persists despite removal of the field. In one aspect, the invention provides for enhanced stability of the visual appearance. In another aspect, the reflectivity of at least one of the phases is enhanced. In another aspect, one of the phases is particulate in nature and emits visible radiation.

U.S. Pat. No. 6,017,584 (Albert et al.), the disclosure of which is totally incorporated herein by reference, discloses electrophoretic displays and materials useful in fabricating such displays. In particular, encapsulated displays are disclosed. Particles encapsulated therein are dispersed within a suspending, or electrophoretic, fluid. This fluid may be a mixture of two or more fluids or may be a single fluid. The displays may further comprise particles dispersed in a suspending fluid, wherein the particles contain a liquid. In either case, the suspending fluid may have a density or refractive index substantially matched to that of the particles dispersed therein. Also disclosed are electro-osmotic displays. These displays comprise at least one capsule containing either a cellulosic or gel-like internal phase and a liquid phase, or containing two or more immiscible fluids. Application of electric fields to any of the electrophoretic displays described affects an optical property of the display.

U.S. Pat. No. 6,067,185 (Albert et al.), the disclosure of which is totally incorporated herein by reference, discloses electrophoretic displays and materials useful in fabricating such displays. In particular, encapsulated displays are disclosed. Particles encapsulated therein are dispersed within a suspending, or electrophoretic, fluid. This fluid may be a mixture of two or more fluids or may be a single fluid. The displays may further comprise particles dispersed in a suspending fluid, wherein the particles contain a liquid. In either case, the suspending fluid may have a density or refractive index substantially matched to that of the particles dispersed therein. Finally, also disclosed are electro-osmotic displays. These displays comprise at least one capsule containing either a cellulosic or gel-like internal phase and a liquid phase, or containing two or more immiscible fluids. Application of electric fields to any of the electrophoretic displays affects an optical property of the display.

U.S. Pat. No. 6,118,426 (Albert et al.), the disclosure of which is totally incorporated herein by reference, discloses a process for creating an electronically addressable display including multiple printing operations, similar to a multicolor process in conventional screen printing. In some of the process steps, electrically non-active inks are printed onto areas of the receiving substrate, and in other steps, electrically active inks are printed onto different areas of the substrate. The printed display can be used in a variety of applications. This display can be used as an indicator by changing state of the display after a certain time has elapsed, or when a certain pressure, thermal, radiative, moisture, acoustic, inclination, pH, or other threshold is passed. In one embodiment, the display is incorporated into a battery indicator. A sticker display is described. The sticker is adhesive backed and may then be applied to a surface to create a functional information display unit. This invention also features a display that is both powered and controlled using radio frequencies. It describes a complete system for controlling, addressing, and powering a display. The system includes an antenna or antennae, passive charging circuitry, and active control system, a display, and an energy storage unit. There is also a separate transmitter that provides the remote power for the display. The system is meant to be used anywhere it is useful to provide intermittent updates of information such as in a store, on a highway, or in an airport. A tile-based display allowing a modular system for large area display is created using a printable display material.

U.S. Pat. No. 6,120,588 (Jacobson), the disclosure of which is totally incorporated herein by reference, discloses a system of electronically active inks which may include electronically addressable contrast media, conductors, insulators, resistors, semiconductive materials, magnetic materials, spin materials, piezoelectric materials, optoelectronic, thermoelectric or radio frequency materials. Also disclosed is a printing system capable of laying down said materials in a definite pattern. Such a system may be used for instance to: print a flat panel display complete with onboard drive logic; print a working logic circuit onto any of a large class of substrates; print an electrostatic or piezoelectric motor with onboard logic and feedback or print a working radio transmitter or receiver.

U.S. Pat. No. 6,120,839 (Comiskey et al.), the disclosure of which is totally incorporated herein by reference, discloses electrophoretic displays and materials useful in fabricating such displays. In particular, encapsulated displays are disclosed. Particles encapsulated therein are dispersed within a suspending, or electrophoretic, fluid. This fluid may be a mixture of two or more fluids or may be a single fluid. The displays may further comprise particles dispersed in a suspending fluid, wherein the particles contain a liquid. In either case, the suspending fluid may have a density or refractive index substantially matched to that of the particles dispersed therein. Also disclosed are electro-osmotic displays. These displays comprise at least one capsule containing either a cellulosic or gel-like internal phase and a liquid phase, or containing two or more immiscible fluids. Application of electric fields to any of the electrophoretic displays described affects an optical property of the display.

U.S. Pat. No. 6,124,851 (Jacobson), the disclosure of which is totally incorporated herein by reference, discloses an electronic book comprising multiple, electronically addressable, page displays. Said page displays may be formed on flexible, thin substrates. Said book may additionally encompass memory, power, control functions and communications.

U.S. Pat. No. 6,130,773 (Jacobson et al.), the disclosure of which is totally incorporated herein by reference, discloses an electrophoretic display having a substantially two-dimensional arrangement of microcapsules each having therein an electrophoretic composition of a dielectric fluid and a suspension of particles that visually contrast with the dielectric liquid and also exhibit surface charges; a pair of electrodes, at least one of which is visually transparent, disposed on and covering opposite sides of the microcapsule arrangement; and a power source for creating a potential difference between the two electrodes, the potential difference causing the particles to migrate toward one of the electrodes. The display may be powered by one or more piezoelectric elements, which are also suitable for powering other types of nonemissive displays.

U.S. Pat. No. 6,130,774 (Albert et al.), the disclosure of which is totally incorporated herein by reference, discloses an electrophoretic display element including a capsule having a first, larger surface and a second, smaller surface. The capsule contains a suspending fluid and at least one particle dispersed within said suspending fluid. Application of a first electrical field causes the particle or particles to migrate towards the first, larger surface of the capsule, causing it to take on the visual appearance of the particles. Application of a second electrical field causes the particle or particles to migrate towards the second, smaller surface, allowing the capsule to take on the visual appearance of the dispersing fluid or of a substrate or electrode positioned behind the display element. Displays may be fabricated from multiple display elements arranged on a substrate.

U.S. Pat. No. 6,172,798 (Albert et al.), the disclosure of which is totally incorporated herein by reference, discloses an electrophoretic display element which includes a capsule having a first, larger surface and a second, smaller surface. The capsule contains a suspending fluid and at least one particle dispersed within said suspending fluid. Application of a first electrical field causes the particle or particles to migrate towards the first, larger surface of the capsule, causing it to take on the visual appearance of the particles. Application of a second electrical field causes the particle or particles to migrate towards the second, smaller surface, allowing the capsule to take on the visual appearance of the dispersing fluid or of a substrate or electrode positioned behind the display element. Displays may be fabricated from multiple display elements arranged on a substrate.

U.S. Pat. No. 6,177,921 (Comiskey et al.), the disclosure of which is totally incorporated herein by reference, discloses addressing schemes for controlling electronically addressable displays including a scheme for rear-addressing displays, which allows for in-plane switching of the display material. Other schemes include a rear-addressing scheme which uses a retroreflecting surface to enable greater viewing angle and contrast. Another scheme includes an electrode structure that facilitates manufacture and control of a color display. Another electrode structure facilitates addressing a display using an electrostatic stylus. Methods of using the disclosed electrode structures are also disclosed. Another scheme includes devices combining display materials with silicon transistor addressing structures.

While known compositions and processes are suitable for their intended purposes, a need remains for improved display apparatus. In addition, a need remains for display apparatus capable of exhibiting two or more colors. Further, a need remains for display apparatus having photochromic characteristics. Additionally, a need remains for display apparatus with photochromic characteristics wherein the photochromic material is thermally stable. There is also a need for display apparatus with photochromic characteristics wherein both resonance forms of the photochromic material are stable. In addition, there is a need for display apparatus with photochromic characteristics wherein the two resonance forms of the photochromic material are addressable at different wavelengths. Further, there is a need for display apparatus with photochromic characteristics wherein both resonance forms of the photochromic material are stable for reasonable periods of time without the need for constant irradiation to maintain the resonance form.

SUMMARY OF THE INVENTION

The present invention is directed to a display comprising an arrangement of a plurality of optically anisotropic rotatable elements, each of said rotatable elements having a surface in contact with an enabling fluid, said rotatable elements being electrically dipolar in the presence of the enabling fluid and thus being subject to rotation upon application of an electric field, said rotatable elements being free to rotate in place but not free to translate substantially so as to disrupt the arrangement of rotatable elements, wherein a first portion of said surface contains a mixture of a chelating agent and a spiropyran material of the formula

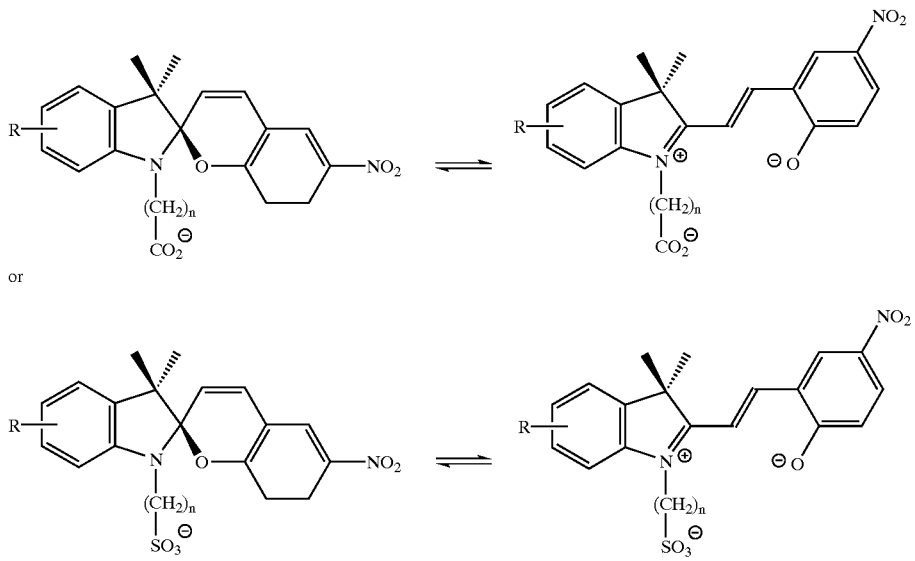

wherein n is an integer representing the number of repeat —$CH_2$— units and R is —H or —CH=$CH_2$, and wherein a second portion of said surface contains substantially no spiropyran.

DETAILED DESCRIPTION OF THE INVENTION

Figure 1:
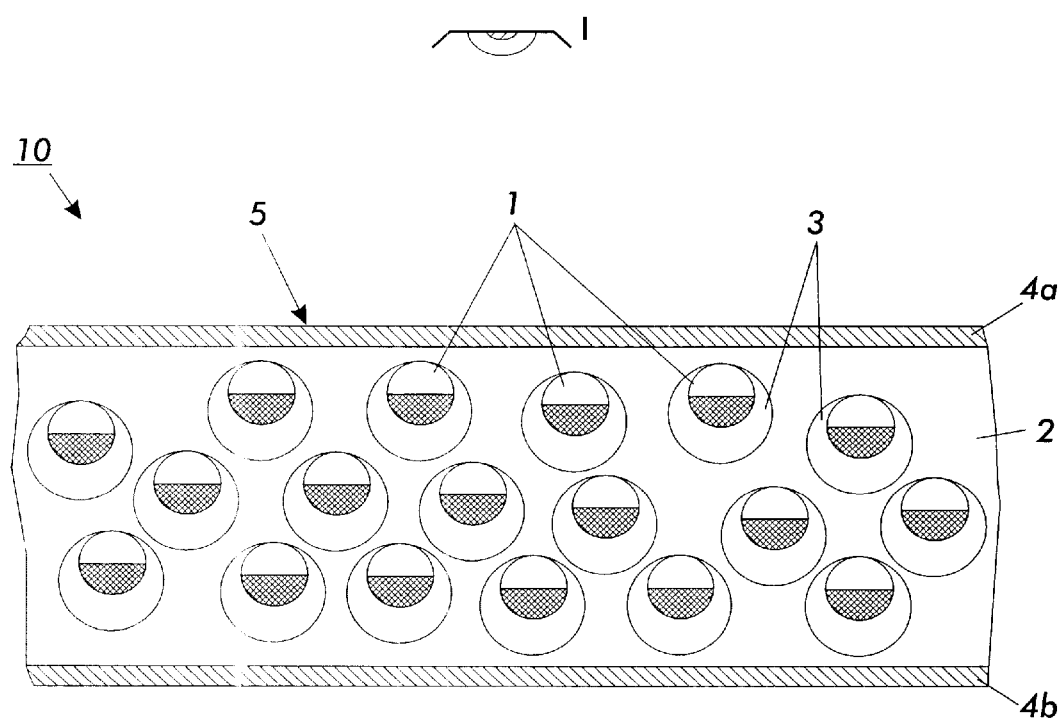
FIG. 1 is a gyricon display employing spherical rotatable elements of the present invention.

An exemplary gyricon display 10 is shown in side view in FIG. 1. Bichromal rotatable elements 1 (spherical balls being illustrated) are disposed in substrate 2 that is swelled by an enabling fluid (in this specific embodiment, a dielectric liquid) creating cavities 3 in which the rotatable elements 1 are free to rotate but are not free to translate substantially so as to disrupt the arrangement of rotatable elements. The rotatable elements 1 are electrically dipolar in the presence of the enabling fluid and so are subject to rotation upon application of an electric field, as by matrix-addressable electrodes 4a and 4b. The electrode 4a closest to upper surface 5 is preferably (although not necessarily) substantially transparent. An observer at I sees an image formed by the two-colored pattern (black and white being illustrated in the drawing) of the rotatable elements 1 as rotated to expose their black or white faces (hemispheres) to the upper surface 5 of substrate 2. The white hemispheres of the bichromal rotatable elements contain a spiropyran photochromic material according to the present invention, when exposed to radiation of the appropriate wavelength, these hemispheres of the rotatable elements can be switched from one color to another.

Examples of suitable materials for substrate 2 include elastomers, such as SYLGARD® 184, available from Dow Corning, Midland, Mich., Stauffer and Wacker V-53 elastomer, and the like, as well as mixtures thereof. After the rotatable elements have been dispersed within the liquid elastomer, the elastomer is cured by any desired or effective method, such as application of heat, radiation, chemical curing, or the like. Materials other than elastomers are also suitable for the substrate 2, such as epoxies, rigid plastics, including poyethylene, polystyrene, plexiglass, or the like.

Examples of suitable enabling fluids include dielectric liquids such as paraffinic hydrocarbons, such as the ISO-PAR® series available from Ashland Chemicals, including ISOPAR® L, ISOPAR® M, or the like, fluorinated hydrocarbons (both fully fluorinated and partially fluorinated), such as the fully fluorinated hydrocarbon perfluorooctane, the partially fluorinated hydrocarbon 3M HFE 7100 available from 3M, and the partially fluorinated polyethylene FREON® TF, vegetable oils, such as soybean oil, coconut oil, and the like, triglyceride liquids, such as tributyrin, tricaproin, and the like, silicon oils, such as DOW CORNING® 1 Centistoke 200 oil, 2 Centistoke 200 oil, and 10 Centistoke 200 oil, and the like, as well as mixtures thereof.

Spherical balls as the rotatable elements have a number of advantages. For example, spherical rotatable balls can be readily manufactured by a number of techniques, as disclosed in, for example, U.S. Pat. No. 5,262,098, U.S. Pat. No. 5,344,594, and other patents and patent applications referenced hereinabove, the disclosures of each of which are totally incorporated herein by reference. In addition, spheres are symmetrical in three dimensions, which means that fabrication of a gyricon display sheet from spherical particles is straighforward; the balls can be dispersed throughout an elastomer substrate, which is then swelled with enabling fluid to form spherical cavities around the balls. The spherical balls can be placed anywhere within the substrate, and at any orientation with respect to each other and with respect to the substrate surface. There is no need to align the balls with one another or with the substrate surface. Once in place, a ball is free to rotate about any axis within its cavity.

Figure 2A:
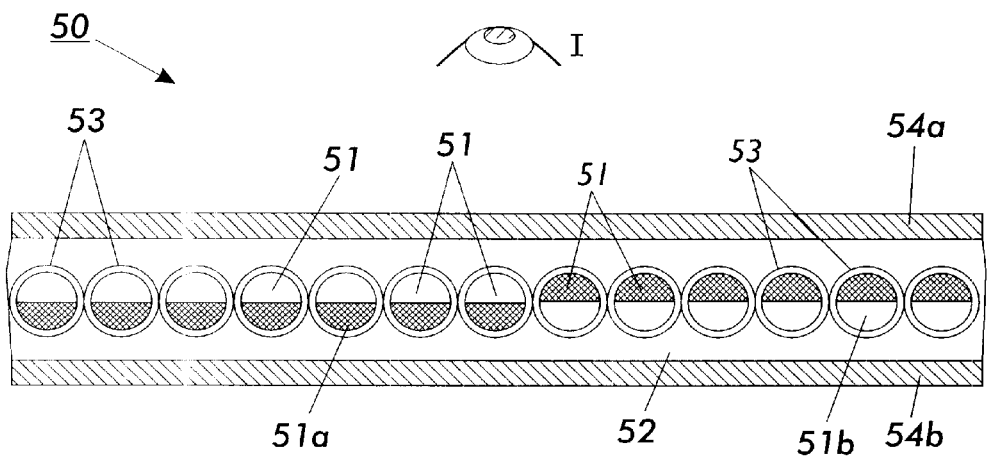
FIGS. 2A and 2B are, respectively, side and top views of a gyricon display in an embodiment wherein cylindrical rotatable elements of the present invention are arrayed in a monolayer configuration.
Figure 2B:
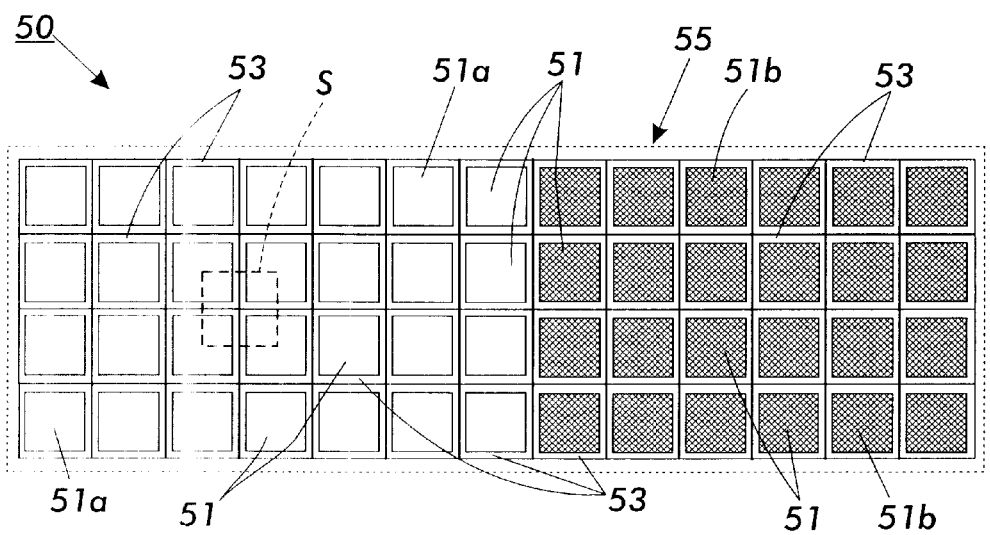

Rotatable elements of other than spherical shape are also suitable for the present invention. Cylindrical rotatable elements, for example, are suitable. FIGS. 2A and 2B provide, respectively, side and top views of a gyricon display 50 in a specific embodiment employing cylindrical rotatable elements. In display 50, rotatable cylinders 51 (in this drawing illustrated as being of unit (that is, 1:1) aspect ratio, although other aspect ratios are also acceptable) are arrayed in a monolayer array having a rectangular packing geometry. Preferably (although not necessarily), cylinders 51 are placed as close to one another as possible in the monolayer. Cylinders 51 are situated in substrate 52, of a material such as an elastomer which is swelled by an enabling fluid (not shown) creating cavities 53 in which the cylinders 51 are free to rotate. The cavities 53 preferably (although not necessarily) are made as small as possible with respect to cylinders 51, so that the cylinders nearly fill the cavities. Also, cavities 53 preferably (although not necessarily) are placed as close to one another as possible, so that the cavity walls are as thin as possible. Preferably (although not necessarily), cylinders 51 are of substantially uniform diameter and situated at a substantially uniform distance from upper surface 55. It will be appreciated that the arrangement of cylinders 51 and cavities 53 in display 50 minimizes both the center-to-center spacing and the surface-to-surface spacing between neighboring cylinders.

The white portions of the cylindrical rotatable elements illustrated in these Figures contain a spiropyran photochromic material according to the present invention; when exposed to radiation of the appropriate wavelength, these portions of the cylindrical rotatable elements can be switched from one color to another.

Cylinders 51 are electrically dipolar in the presence of the enabling fluid and so are subject to rotation upon application of an electric field, as by matrix addressable electrodes 54a and 54b. The electrode 54a closest to upper surface 55 is preferably (although not necessarily) substantially transparent An observer at I sees an image formed by the two-color (black and white illustrated in the drawing) pattern of the cylinders 51 as rotated to expose their black or white faces to the upper surface 55 of substrate 52. For example, the observer sees the white faces of cylinders such as cylinder 51a and the black faces of cylinders such as cylinder 51b.

The side view FIG. 2A reveals the monolayer construction of display 50. The top view of FIG. 2B illustrates the rectangular packing geometry of cylinders 51 in the monolayer. The cylinders 51 appear as squares visible through upper surface 55. The centers of cylinders 51 form a square pattern, as shown by exemplary square S.

The projected areas of cylinders 51 in the plane of surface 55 preferably (although not necessarily) cover as much of the total area of the plane of surface 55 as possible. To this end, cavities 53 preferably are made as small as possible, ideally no larger than the cylinders themselves (or as close to this ideal as is consistent with proper cylinder rotation). The greater the ratio between the sum of the projected areas of the cylinders in the plane of viewing surface 55 and the total area of viewing surface 55, the greater the display reflectance and the brighter the display. It will be appreciated that, whereas the maximum areal coverage theoretically possible with spherical balls (of a single substantially uniform diameter, without interstitial smaller balls) is about 90.7 percent, the maximum for cylinders is 100 percent. Thus a gyricon display made from a close-packed monolayer of cylinders can be made brighter than a gyricon display made from a close-packed monolayer of spherical balls.

Other arrangements of cylindrical rotatable elements are also possible, such as cylinders arrayed in two or more layers in a substrate, cylinders with parallel longitudinal axes randomly distributed within a substrate, cylinders with random longitudinal axes randomly distributed within a substrate, cylinders arrayed in staggered arrays, or the like, as illustrated in, for example, U.S. Pat. No. 6,055,091, the disclosure of which is totally incorporated herein by reference. Cylindrical rotatable elements can also be prepared as disclosed in, for example, U.S. Pat. No. 6,055,091.

Figure 3:
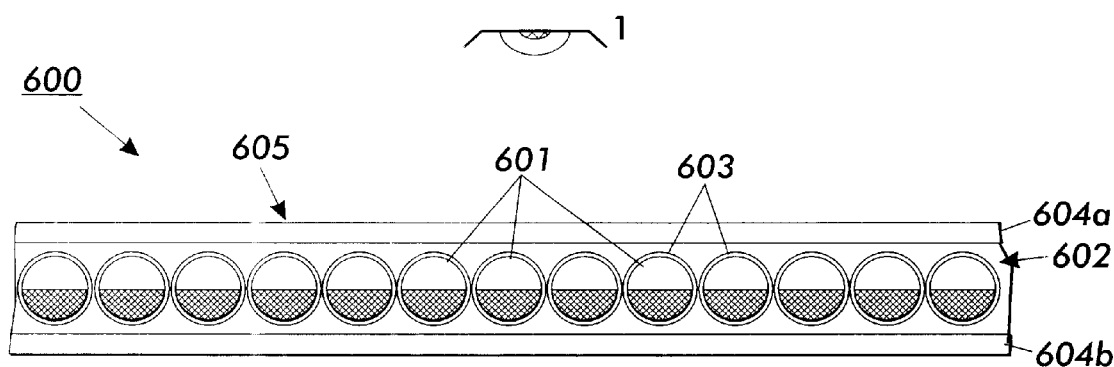
FIG. 3 illustrates a side view of a gyricon display in an embodiment wherein the rotatable elements of the present invention are arrayed in a close-packed monolayer.
Figure 4A:
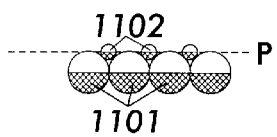
FIGS. 4(a) through 4(f) are a series of views illustrating gyricon displays each having two different populations of rotatable elements of the present invention, with smaller-diameter rotatable elements filling the interstices in a close-packed monolayer of larger-diameter rotatable elements.
Figure 4B:
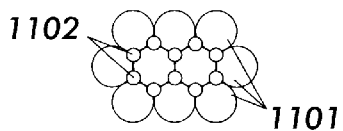
Figure 4C:
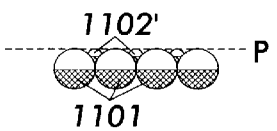
Figure 4D:
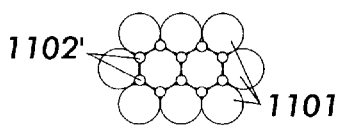
Figure 4E:
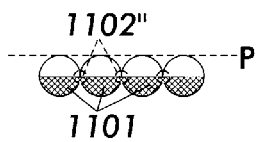
Figure 4F:
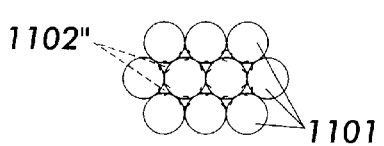

FIG. 3 provides a view of a gyricon display 600 in a specific embodiment. In display 600, rotatable elements 601 are placed as close to one another as possible in a monolayer in elastomer substrate 602. Substrate 602 is swelled by an enabling fluid (not shown) creating cavities 603 in which the rotatable elements 601 are free to rotate. The cavities 603 preferably (although not necessarily) are made as small as possible with respect to rotatable elements 601, so that the rotatable elements nearly fill the cavities. Also, cavities 603 preferably (although not necessarily) are placed as close to one another as possible, so that the cavity walls are as thin as possible. Preferably (although not necessarily), rotatable elements 601 are of substantially uniform diameter and situated at a substantially uniform distance from upper surface 605. It will be appreciated that the arrangement of rotatable elements 601 and cavities 603 in display 600 minimizes both the center-to-center spacing and the surfaceto-surface spacing between neighboring rotatable elements. A preferred arrangement of the rotatable elements is a hexagonal array, although other arrays such as rectangular and rhomboid arrays are also suitable, as illustrated in, for example, U.S. Pat. No. 5,825,529, the disclosure of which is totally incorporated herein by reference. The white hemispheres of the rotatable elements illustrated in this Figure contain a spiropyran photochromic material according to the present invention, when exposed to radiation of the appropriate wavelength, these hemispheres of the rotatable elements can be switched from one color to another.

Closely packed monolayer gyricon displays can be fabricated by (1) creating a monolayer of rotatable elements according to known techniques, such as those disclosed in, for example, "A Simple Method for the Production of a Two-Dimensional, Ordered Array of Small Latex Particles, R. Micheletto, H. Fukuda, and M. Ohtsu, *Langmuir*, Vol. 11, no. 9, pp. 3333 to 3336 (1995), the disclosure of which is totally incorporated herein by reference, (2) preparing an elastomer sheet to contain the rotating elements, and (3) swelling the elastomer by application of a dielectric fluid.

A monolayer planar array of spheres of substantially uniform diameter inevitably has interstices between the spheres, even if the sphere surfaces touch one another. Light that passes through the interstices into the depths of the display is essentially lost. To prevent light loss through interstices in a monolayer array, in another embodiment a gyricon display is constructed from two populations of rotatable elements. Preferably, rotatable elements in the first, or main, population are of a first substantially uniform diameter and rotatable elements in the second, or interstitial, population are of a second substantially uniform diameter, with the second diameter chosen so that the rotatable elements in the second population can fill the interstices left by close-packing the rotatable elements from the first population.

FIG. 4 illustrates some of these specific embodiments. Each of the series of views in FIG. 4 illustrates a hexagonally packed planar array of bichromal (black and white in the drawing) balls 1101 with various smaller bichromal balls being used to fill the interstices of the array. It will be appreciated that this embodiment can also be carried out with rotatable elements of other than spherical ball shape, such as cylindrical shape or the like. The white hemispheres of balls 1101 face upwards, and their topmost points lie in a plane P. Views (a) and (b) show, respectively, side and top views of the array of bichromal balls 1101. Smaller bichromal balls 1102 are situated above balls 1101 (that is, closer to the viewing surface of the gyricon display) in the interstices formed by the hexagonal packing arrangement. Balls 1102 also have their white hemispheres facing upwards. Balls 1102 are of a diameter such that the plane that separates their white and black hemispheres is plane P. Views (c) and (d) show, respectively, side and top views of the array of bichromal balls 1101, with smaller bichromal balls 1102' situated above balls 1101 in the interstices formed by the hexagonal packing arrangement. Balls 1102' are of a diameter such that their topmost points lie in plane P. Views (e) and (f) show, respectively, side and top views of the array of bichromal balls 1101, with smaller bichromal balls 1102" situated above balls 1101 in the interstices formed by the hexagonal packing arrangement. (In views (e) and (f), balls 1102" are hidden by balls 1101 and, accordingly, are shown as dashed outlines.) Balls 1102" are of a diameter such that their surfaces are tangential to the surfaces of balls 1101 when their centers are coplanar with the centers of balls 1101, as shown. The white hemispheres of the bichromal rotatable elements contain a spiropyran photochromic material according to the present invention; when exposed to radiation of the appropriate wavelength, these hemispheres of the rotatable elements can be switched from one color to another.

Preferably (although not necesssarily), as shown in all the examples of FIG. 4, interstitial balls are situated in a planar array above the planar array of the main bichromal balls. That is, the plane formed by the centers of the smaller balls is closer to the viewing surface than the plane formed by the centers of the monolayer (or close-packed top layer) of larger balls. With this arrangement, light reflected from the white hemispheres of the interstitial balls is not absorbed by the black hemispheres of the main bichromal balls, as would be the case if the interstitial balls were disposed below the layer of larger balls.

Further, as shown in FIG. 4, the interstitial balls preferably are small enough so that their black hemispheres do not absorb much of the light reflected by the white hemispheres of the main bichromal balls. In this regard, a tradeoff can be made between losses due to absorption by the black hemispheres of the interstitial balls and losses due to passage of light through unfilled portions of the interstices. In views (a) and (b) of FIG. 4, balls 1102 almost completely fill the interstices between balls 1101. However, some of the light scattered from the white hemispheres of balls 1101 is absorbed by the black hemispheres of balls 1102. (Note that plane P, which is the tangent plane for the tops of balls 1101, is also the plane separating the black and white hemispheres of the interstitial balls 1102. Thus none of the light scattered from the very tops of balls 1101 is absorbed by the black hemispheres of balls 1102. This would not be so if balls 1102 were made any larger.) In views (c) and (d) of FIG. 4, balls 1102' largely fill the interstices between balls 1101. Some of the light scattered from the white hemispheres of balls 1101 is absorbed by the black hemispheres of balls 1102', but less so than for interstitial balls 1102 in views (a) and (b) because balls 1102', being smaller than balls 1102, can be situated with their centers below plane P, so that light scattered by the white hemispheres of balls 1101 is less likely to reach the black hemispheres of balls 1102' than the black hemispheres of balls 1102. In views (e) and (f) of FIG. 4, balls 1102" only partly fill the interstices between balls 1101. Balls 1102" are situated with their centers in the same plane as the centers of balls 1101, so very little of the light scattered from the white hemispheres of balls 1101 is absorbed by the black hemispheres of balls 1102". However, light can pass through the portions of the interstices between balls 1101 that are left unfilled by balls 1102". Therefore, with interstitial balls 1102", more light is transmitted beyond the white hemispheres of balls 1101 than is the case with the larger interstitial balls 1102 or 1102'.

In short, as the interstitial balls are made smaller, they can be situated lower with respect to the tops of the main bichromal balls, and so can be made to absorb less light with their black hemispheres. However, as the interstitial balls are made smaller, they fill a smaller part of the interstitial gaps between the main bichromal balls, and so allow more light to pass beyond one hemisphere's depth in the main layer, thereafter to be lost to absorption.

Gyricon displays comprising two sets of rotatable elements of two different diameters can be fabricated as disclosed in, for example, U.S. Pat. No. 5,825,529, the disclosure of which is totally incorporated herein by reference.

In a gyricon display made with swelled elastomer, each rotatable element is situated in a cavity. To achieve the closest possible packing of rotatable elements in such a display, the cavities are preferably made as small and as close together as possible. To achieve still higher packing density, a gyricon display can be constructed without elastomer and without cavities. In such a display, the rotatable elements are placed directly in the enabling fluid. The rotatable elements and the enabling fluid are then sandwiched between two retaining members (such as addressing electrodes). There is no elastomer substrate.

Figure 5:
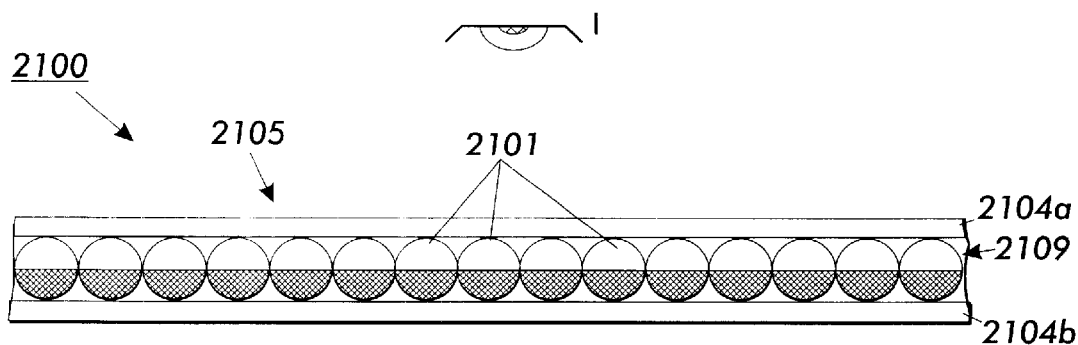
FIG. 5 illustrates an embodiment of the invention in which a close-packed monolayer of rotatable elements of the present invention is placed in an enabling fluid directly between transparent electrodes, without an elastomer or other cavity-containing substrate medium.

FIG. 5 illustrates a side view of a no-cavities gyricon display. In display 2100, a monolayer of rotatable elements 2101 (spherical balls being illustrated, although other configurations are also possible, such as cylinders, prisms, or the like), preferably (although not necessarily) of substantially uniform diameter is situated in enabling dielectric fluid 2109 between matrix-addressable electrodes 2104a and 2104b. Preferably (although not necessarily) when rotatable elements 2101 are spherical, they are arranged in a hexagonal array within the monolayer, packed as close together as is possible consistent with proper ball rotation. Rotatable elements 2101 are electrically dipolar in the presence of enabling dielectric fluid 2109 and so are subject to rotation upon application of an electric field, as by electrodes 2104a and 2104b. The electrode 2104a closest to upper surface 2105 is preferably (although not necessarily) substantially transparent. An observer at I sees an image formed by the two-color pattern (black and white being illustrated in this drawing) of the rotatable elements 2101 as rotated to expose their black or white hemispheres to the upper surface 2105 of display 2100. The white hemispheres of the bichromal rotatable elements contain a spiropyran photochromic material according to the present invention; when exposed to radiation of the appropriate wavelength, these hemispheres of the rotatable elements can be switched from one color to another.

Electrodes 2104a and 2104b serve both to address rotatable elements 2101 and to retain rotatable elements 2101 and fluid 2109 in place. Preferably (although not necessarily) the spacing between electrodes 2104a and 2104b is as close to the diameter of rotatable elements 2101 as is possible consistent with proper element rotation. Rotatable elements 2101 and fluid 2109 can be sealed in display 2100, for example by seals at either end of the display (not shown).

The close packing of rotatable elements 2101 in the monolayer, together with the close spacing of the electrodes 2104a and 2104b, ensures that rotatable elements 2101 do not settle, migrate, or otherwise escape from their respective positions in the monolayer. Interstitial rotatable elements (not shown) can also be included in display 2100, by, for example, using the arrangement and interstitial rotatable element diameter shown in views (c) and (d) of FIG. 4. The smaller rotatable elements are retained in place from above by upper electrode 2104a and from below by the larger rotatable elements 2101.

This embodiment can also be employed with nonspherical rotatable elements, as illustrated in, for example, U.S. Pat. No. 6,055,091, the disclosure of which is totally incorporated herein by reference, In a gyricon display made with swelled elastomer, each rotatable element is situated in a cavity in a substrate, with an enabling fluid filling the cavity. In other embodiments, a gyricon display is made wherein the rotatable element is encapsulated within a microcapsule skin. An enabling fluid is situated between the rotatable element and the microcapsule skin. The microcapsules containing the rotatable elements and the enabling fluid constitute voltage sensitive members that can be dispersed in any medium or substrate across which an electrical field can be impressed, including solids, liquids, liquids curable or otherwise convertible to solids, slurries containing a liquid and solid particles, solid particles that immobilize the microcapsules, or the like. For example, the microcapsules can be dispersed in a liquid, such as an optically clear epoxy, which can subsequently be hardened. If the hardened liquid, now a solid, is of sufficient strength no further protection is required. The resultant display is then in the form of a thin, paper-like sheet without the bulkiness and optical problems created by protective cover sheets. Since the substrate need not be selected from elastomers or other materials that swell when plasticized, a wide range of materials can be employed as substrates. Alternatively, the resultant display can easily be conformally coated onto a non-planar surface for even greater flexibility of applications. For example, the microcapsules can be mixed with a transparent hardenable material, such as a varnish, and the resulting dispersion can be coated onto objects of any shape, articles of decoration or camoflauge, fabrics, articles of clothing, or the like.

Figure 6:
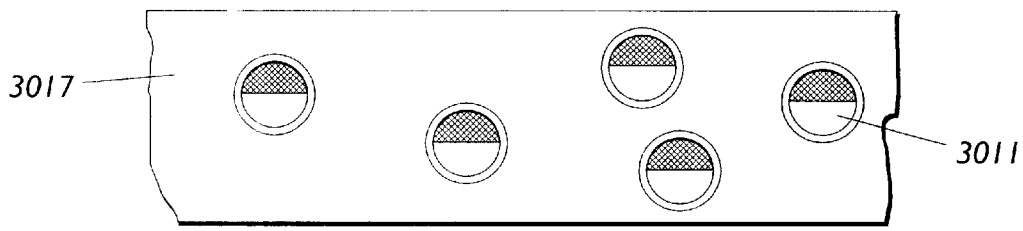
FIG. 6 illustrates an embodiment of the invention in which a plurality of rotatable elements of the present invention encapsulated within microcapsules and surrounded by an enabling fluid are dispersed in a substrate.
Figure 7:
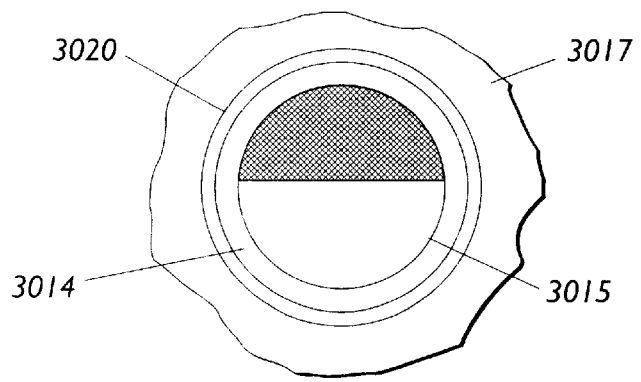
FIG. 7 illustrates an embodiment of the invention in which a single rotatable element the present invention is encapsulated within a microcapsule and surrounded by an enabling fluid, with the microcapsule being dispersed in a substrate.

As illustrated in FIGS. 6 and 7, bichromal rotatable element 3015 (spherical balls being illustrated) is encapsulated within microcapsule skin 3020. Surrounding rotatable element 3015 and within microcapsule skin 3020 is a sufficient thickness of enabling fluid 3014 to allow free rotation of the rotatable element 3015 within microcapsule skin 3020. Optionally, the microcapsules are disposed within substrate 3017. The white hemispheres of the bichromal rotatable elements illustrated in these Figures contain a spiropyran photochromic material according to the present invention; when exposed to radiation of the appropriate wavelength, these hemispheres of the rotatable elements can be switched from one color to another.

The microcapsule shell containing the rotatable element and the enabling fluid can be made by any desired or suitable process. One suitable process comprises (1) coating the rotatable element with the desired shell material by, for example, vacuum coating of a material such as PARYLENE®, precipitation of a polymer onto the rotatable element surface by temperature change, pH change, or the like, as disclosed in, for example, "Polymer-Encapsulated Particles with Controlled Morphologies: Preparation, Characterization and Application", Wei-Hsin Hou, Ph.D. Thesis, Lehigh University, 1991, UMI Dissertation Service, University Microfilms International, Ann Arbor, Ml, the disclosure of which is totally incorporated herein by reference, depositing a hardenable liquid, such as an epoxy or the like, onto the rotatable element by any desired method, such as a mist or in a tumbling situation such as in a fluidized bed or the like, deposition of a polymer by an electrostatic painting process, or the like, and (2) after applying the coating, immersing the rotatable element in a dielectric liquid which has a chemical affinity for the coating and plasticizes it, causing it to swell; this process will also drive the liquid into the space between the ball and the coating, at least partially filling it. Subsequently placing the microcapsules thus formed into a second liquid that diffuses more rapidly through the shell than the first liquid will tend to fill the space within the shell more fully.

Another method for preparing the microcapsule shell containing the rotatable element and the enabling fluid employs interfacial polymerization, as disclosed in, for example, *Microcapsule Processing and Technology,* Asaji Kondo, Marcel Dekker, Inc. (1979) and U.S. Pat. No. 5,604,027, the disclosures of each of which are totally incorporated herein by reference.

Other methods for preparing the encapsulated rotatable elements are disclosed in, for example, Copending application U.S. Ser. No. 09/749,379, Copending application U.S. Ser. No. 09/749,379, Copending application U.S. Ser. No. 09/723,187, and Copending application U.S. Ser. No. 09/722,565, the disclosures of each of which are totally incorporated herein by reference.

The photochromic spiropyran materials of the present invention can also be used in rotatable elements as disclosed in, for example, U.S. Pat. No. 4,261,653, the disclosure of which is totally incorporated herein by reference.

The rotatable elements of the present invention contain a spiropyran material of the formula

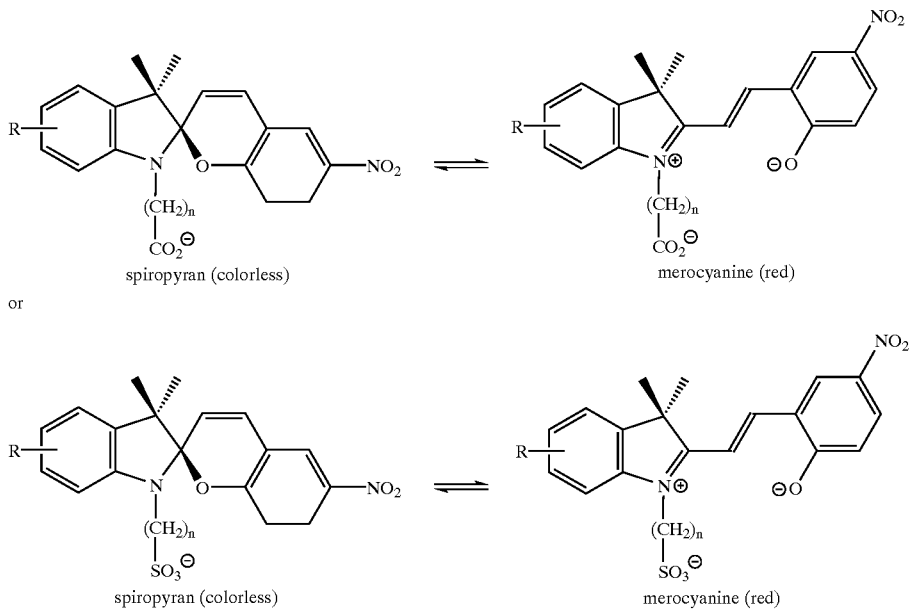

spiropyran (colorless) ⇌ merocyanine (red)

or spiropyran (colorless) ⇌ merocyanine (red)

wherein n is an integer representing the number of repeat —CH₂— units, typically being from about 2 to about 8, although the value of n can be outside of this range, and R is —H or —CH=CH₂. The anionic —COO— and —SO₃— groups are, of course, accompanied by cations. Any desired or suitable cations can be employed. Materials of the formula

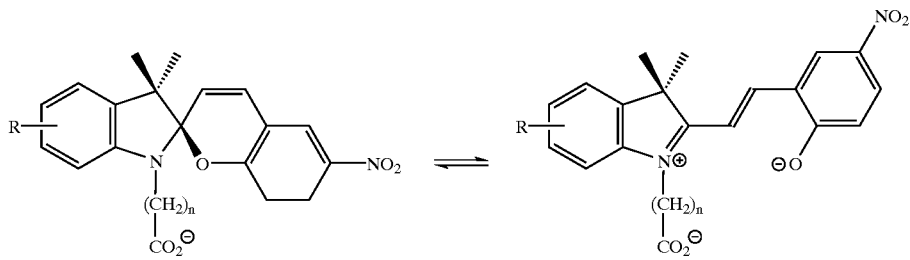

can be prepared by the reaction of 2,3,3-trimethylindolenine with β-iodopropionic acid, followed by condensation with 5-nitrosalicaldehyde in the presence of triethylamine. Materials of the formula

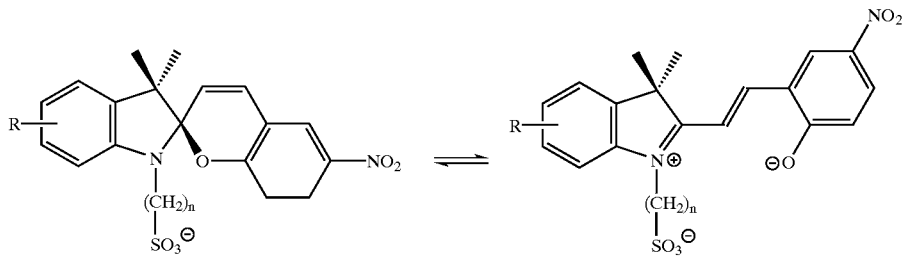

can be prepared by the reaction of 2,3,3-trimethylindolenine with γ-sulfone, followed by condensation with 5-nitrosalicaldehyde in the presence of triethylamine. The spiropyran can be present in or on the rotatable elements in any desired form, including (but not limited to) as a coating covering part but not all of the rotatable element, as a dispersion within the core material of the rotatable element which also has a coating of a color other than the colored form of the spiropyran covering part but not all of the rotatable element, or the like. When the spiropyran is dispersed within the core material of the rotatable elements, the spiropyran is present in the rotatable elements in any desired or effective amount, typically at least about 0.01 percent by weight of the rotatable element core, preferably at least about 0.05 percent by weight of the rotatable element core, and more preferably at least about 0.5 percent by weight of the rotatable element core, and typically no more than about 5 percent by weight of the rotatable element core, although the amount can be outside of these ranges. When the spiropyran is present as a partial coating on the core material of the rotatable elements, the coating is of any desired or effective thickness, typically at least about 0.5 micron, and preferably at least about 1 micron, and typically no more than about 5 microns, and preferably no more than about 3 microns, although the thickness can be outside of these ranges.

The rotatable elements of the present invention also contain a chelating agent with which the merocyanine form of the spiropyran can chelate to stabilize this form of the molecule. The chelating agent is admixed with the spiropyran compound in or on the rotatable element. Examples of suitable chelating agents include metal salts in the +2 state, such as $Ca^{2+}$, $Zn^{2+}$, $Mg^{2+}$, transition metals, and the like, wherein the accompanying anion or anions are such that the metal salt is water soluble, such as nitrate, chloride, bromide, and the like. The chelating agent is present in the rotatable elements in any desired or effective amount, typically in a molar ratio to the spiropyran of at least about 1 mole of chelating agent for every 1 mole of spiropyran, preferably at least about 2 moles of chelating agent for every 1 mole of spiropyran, more preferably at least about 3 moles of chelating agent for every 1 mole of spiropyran, and even more preferably at least about 5 moles of chelating agent for every 1 mole of spiropyran, and typically no more than about 10 moles of chelating agent for every 1 mole of spiropyran, although there is no upper limit on the amount of chelating agent that can be present, and although the amount of chelating agent can be outside of these ranges.

The rotatable elements can be of any desired rotatable shape or configuration, such as spheres, cylinders, prisms, or the like. The rotatable elements can be prepared by any desired or effective method. For example, the rotatable elements can be of glass, silicon, plastics such as polyethylene, polymethyl methacrylate, polycarbonate, nylon, commercially available materials such as POLY-WAX® 1000 available from Baker Chemical, or the like, aluminum, epoxies, waxes such as carnauba wax, candelia wax, castor wax, or the like, a core (silicon, plastics such as polyethylene, polymethyl methacrylate, polycarbonate, nylon, commercially available materials such as POLY-WAX® 1000 available from Baker Chemical, or the like, aluminum, epoxies, waxes such as carnauba wax, candelia wax, castor wax, or the like) onto which has been coated by any desired technique (such as vacuum deposition, sputtering or the like) another material such as titanium oxide, indium, magnesium fluoride, aluminum, antimony trisulfide, silicon monoxide, silicon dioxide, amorphous silicon, or the like, a core (silicon, plastics such as polyethylene, polymethyl methacrylate, polycarbonate, nylon, commercially available materials such as POLYWAX® 1000 available from Baker Chemical, or the like, aluminum, epoxies, waxes such as carnauba wax, candelia wax, castor wax, or the like) into which has been dispersed a colorant, such as ferroelectric ceramics, such as lead zirconate titanate, magnetites, ferrites, iron oxide, manganese ferrites, DUPONT® R900 titanium dioxide, carbon black, such as CABOT® MOGUL® L and CABOT® MONARCH® 1000, FERRO® 6331 black pigment, BAKER® CHEMICAL Cresyl violet blue, BAKER® CHEMICAL Rhodamine 6G, DUPONT® Rhodamine BI, DUPONT® Spirit Blue NS, DUPONT® Victoria Blue B base, ALLIED® CHEMICALS Iosol Blue, EASTMAN® Acridine orange, CALCO® OIL blue N, CALCO® OIL black, other pigments or dyes, or the like. The photochromic spiropyran material and chelating agent can be vacuum deposited onto portions of the rotatable elements so that at least a first portion of the surface of the rotatable element has the photochromic spiropyran material and chelating agent thereon and at least a second portion of surface of the rotatable element has substantially no photochromic spiropyran material thereon. Any desired or effective vacuum deposition method can be employed, such as those disclosed in, for example, U.S. Pat. No. 4,438,160, the disclosure of which is totally incorporated herein by reference, or the like.

Alternatively, the photochromic spiropyran material and the chelating agent can be dispersed within the core material of the rotatable element, and a second material of another color (such as titanium oxide, indium, magnesium fluoride, aluminum, antimony trisulfide, silicon monoxide, silicon dioxide, amorphous silicon, or the like) can be vacuum deposited onto portions of the rotatable elements so that at least one portion of the surface of the rotatable element has the second material thereon and at least one portion of the surface of the rotatable element has substantially no second material thereon (thereby leaving the core material containing the photochromic spiropyran material and chelating agent exposed on the surface).

Spherical rotatable elements of the present invention can also be prepared by the methods disclosed in, for example, U,S, Patent 5,262,098, the disclosure of which is totally incorporated herein by reference, wherein two portions of a hardenable material (such as a wax, a curable epoxy, or the like) are prepared, one containing therein the photochromic spiropyran material and the chelating agent, the other containing substantially no photochromic spiropyran material and, optionally, a colorant (including pigments, dyes, mixtures thereof, or the like) of any desired color, and the two differently colored portions of hardenable material are used with an apparatus as disclosed in the patent to form bichromal balls. Multichromal rotatable elements of two or more colors can also be prepared by similar methods as disclosed in, for example, U.S. Pat. No. 5,344,594, the disclosure of which is totally incorporated herein by reference. Cylindrical rotatable elements of the present invention can be prepared with high viscosity hardenable liquids by similar processes, as disclosed in, for example, U.S. Pat. No. 6,055,091, the disclosure of which is totally incorporated herein by reference.

Additional methods for preparing rotatable elements are disclosed in, for example, Copending application U.S. Ser. No. 09/360,052, Copending application U.S., Ser. No. 09/360,088, Copending application U.S. Ser. No. 09/749,379, and Copending application U.S. Ser. No. 09/465,801, the disclosures of each of which are totally incorporated herein by reference.

Rotatable elements can also be prepared by chemical methods, such as those disclosed in, for example, U.S. Pat. No. 5,989,629, Copending application U.S. Ser. No. 09/035,518, and Copending application U.S. Ser. No. 09/723,187, the disclosures of each of which are totally incorporated herein by reference.

Also included within the scope of the present invention are rotatable elements having three or more aspects, at least one of which comprises the photochromic spiropyran material and the chelating agent. Rotatable elements with three or more aspects and methods for the preparation thereof are disclosed in, for example, U.S. Pat. No. 5,777,782, U.S. Pat. No. 5,717,514, U.S. Pat. No. 5,919,409, U.S. Pat. No. 5,891,479, U.S. Pat. No. 5,708,525, U.S. Pat. No. 5,751,268, U.S. Pat. No. 5,760,761, U.S. Pat. No. 5,892,497, U.S. Pat. No. 5,737,115, U.S. Pat. No. 5,767,826, and U.S. Pat. No.

5,894,367, the disclosures of each of which are totally incorporated herein by reference.

The surface portions of the rotatable elements of the present invention having the spiropyran therein or thereon are photochromic in that they have a first state corresponding to a first absorption spectrum and a second state corresponding to a second absorption spectrum. The photochromic shift from the first state to the second state can be effected by any method suitable for the photochromic spiropyran material. Examples of methods for inducing the photochromic shift include irradiation with radiation of a suitable wavelength, typically from about 190 to about 425 nanometers, although the wavelength can be outside this range. The reverse photochromic effect can be induced by irradiation with visible light, typically in the wavelength range of from about 425 to about 700 nanometers, although the wavelength can be outside this range, or by the application of heat. By exposing the rotatable elements of the present invention to radiation of the appropriate wavelength, the surface portions of the rotatable elements having the spiropyran therein or thereon can be switched from one color to another, either in imagewise fashion by imagewise exposure to radiation or uniformly by uniform exposure to radiation. Another embodiment of the present invention is directed to a process which comprises (a) providing a display according to the present invention; (b) applying to the display an electrical field, thereby causing a first population of said rotatable elements to rotate so that said first portion is oriented toward a viewer and causing a second population of said rotatable elements to rotate so that said second portion is oriented toward the viewer; and (c) exposing said display to radiation at a wavelength effective to cause the spiropyran material in the first portion of at least some members of the first population of rotatable elements to shift to a merocyanine form. In a specific embodiment, subsequent to step (c), the display is exposed to radiation at a wavelength effective to cause at least some of the rotatable elements containing the material in the merocyanine form to shift back to the spiropyran.

The mixture of photochromic spiropyran material and chelating agent is sufficiently different in electrical characteristics from the material comprising the portion or portions of the rotatable element having substantially no photochromic spiropyran material thereon that an electrical dipole moment is associated with the rotatable element, enabling rotation of the rotatable element in the presence of an applied external field. The electrical anisotropy of a rotatable element need not be based on zeta potential. It is sufficient that there is an electrical dipole moment associated with the rotatable element, the dipole moment being aligned with respect to the rotatable element in such a way as to facilitate a useful rotation of the rotatable element in the presence of an applied external electric field. (Typically, the dipole moment is oriented along an axis of symmetry of the rotatable element.) Further, it should be noted that a rotatable element can have an electrical monopole moment in addition to its electrical dipole moment, as for example when the dipole moment arises from a separation of two positive charges of different magnitudes, the resulting charge distribution being equivalent to a positive electrical monopole superposed with a electrical dipole.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

Preparation of Carboxylate and Sulfonate Substituted Spiropyran Salts Step 1: Synthesis of 2, 3,3-Trimethylindolinium Salts

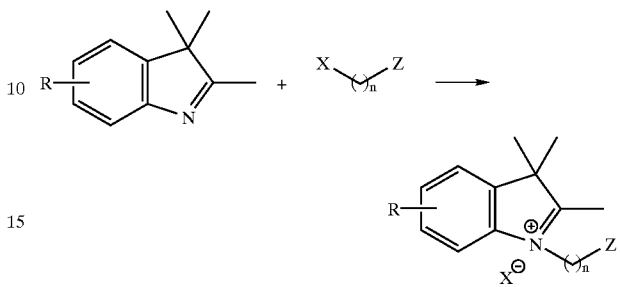

Because of the relatively weak nucleophilicity of 2,3,3-trimethylindolenine (where R is hydrogen) or its vinyl derivative 2,3,3,8-vinyl trylmethylindolenine (where R is vinyl), the syntheses of 2,3,3-trimethylindolinium salts were conducted either in the absence of any solvent or with a dipolar aprotic solvent (nitromethane) at 100° C.

Vinyl containing indolenine precursors can be prepared by Friedel-Craffs acylation of the precursors for the preparation of polymerizable spiropyrans. Alternatively, Friedel-Crafts acylation of the spiropyrans can be carried out. A general synthetic route to these materials is disclosed in, for example, G. K. Hamer, I. R. Peat, and W. F. Reynolds, "Investigations of Substituent Effects by Nuclear Magnetic Resonance Spectroscopy and All-Valence Electron Molecular Orbital Calculations. I. 4-Substituted Styrenes," Can. J. Chem., Vol. 51, 897–914 (1973) and G. K. Hamer, I. R. Peat, and W. F. Reynolds, "Investigations of Substituent Effects by Nuclear Magnetic Resonance Spectroscopy and All-Valence Electron Molecular Orbital Calculations. II. 4-Substituted α-Methylstyrenes and α-t-Butylstyrenes," Can. J. Chem., Vol. 51, 915–926 (1973), the disclosures of each of which are totally incorporated herein by reference, and is outlined below.

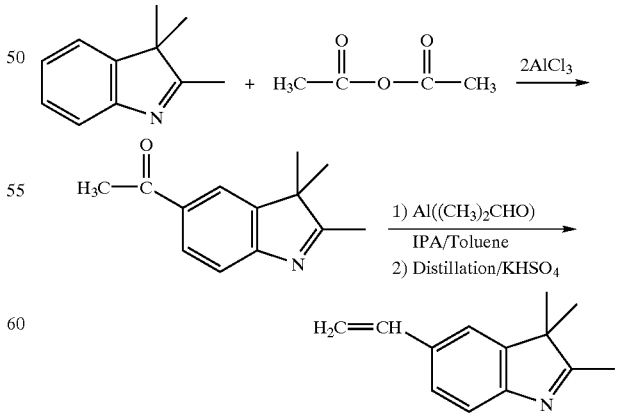

Alkylating agents that can be used in this reaction (all available from Aldrich Chemical Co., Milwaukee, Wis.) are 3-iodopropionic acid, ethyl 5-bromopentanoate, 6-bromohexanoic acid, 1,3-propylsulfone, and 1,4-butylsulfone. The choice of these reagents ensures that competing ring-formation and/or acid-base reactions are minimal to allow for nucleophilic attack of the sp2-N.

IA

Synthesis of N-(2-carboxyethyl)-2,3,3-trimethylindolinium Iodide

The general procedure for the preparation of the 2,3,3-trimethylindolinium salt intermediates is illustrated through the reaction of 2-iodopropionic acid and 2,3,3-trimethylindolenine, Vinyl containing intermediates can also be prepared from the N-(2-carboxyethyl)-2,3,3-trimethylindolinium iodide.

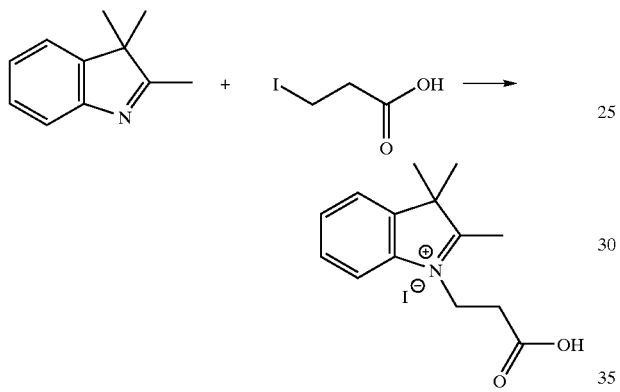

A 2-necked 50 milliliter round-bottomed flask equipped with a magnetic stirring bar and an argon inlet was charged with re-distilled (pressure 2 mm Hg, temperature 45° C.) 2,3,3-trimethylindolenine (7.95 grams, 50.0 mmol) and 3-iodopropionic acid (2.00 grams, 10 mmol). The mixture was heated to 80° C. for 12 hours, during which time the product precipitated out of solution and formed a highly viscous medium. Upon cooling, the reaction mixture was extracted three times with 200 milliliter portions of diethyl ether to remove all of the unreacted starting material. The remaining crystalline solid was then dissolved in 10 milliliters of water, extracted three times with 50 milliliter portions of diethyl ether, and extracted three times with 25 milliliter portions of $CHCl_3$. The aqueous layer was then removed and dried under vacuum (1.0 mm Hg) for 24 hours. The resulting amorphous solid was then recrystallized from toluene/$CHCl_3$ mixtures to produce the N-(2-carboxyethyl)-2,3,3-trimethylindolinium iodide product as 3.0 grams of a yellow solid (83.5 percent yield). $^1H$ and $^{13}C$ NMR spectra indicated the following:

$^1H$ NMR (400.1 MHz) in DMSO-$d_6$: δ 7.97 (1H, m), 7.83 (1H, m), 7.59 (2H, m), 4.64 (2H, t, J=6, N—$CH_2$), 2.97 (2H, t, J=6, $CH_2CO$), 2.86 (3H, s, $CH_3$), 1.52 (6H, s, $CH_3$).

$^{13}C$ NMR (100.1 MHz) in DMSO-$d_6$: 198.0, 171.6, 141.8, 140.7, 129.5, 129.1, 123.7, 115.7, 54.4, 43.9, 31.3, 22.1, 15.0.

IB

Synthesis of N-(ethylpentanoyl)-2,3,3-trimethylindolinium Bromide

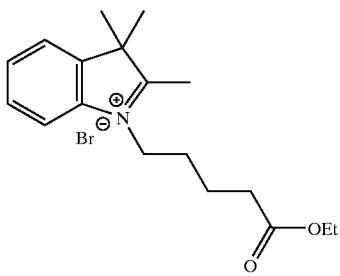

N-(ethylpentanoyl)-2,3,3-trimethylindolinium bromide was prepared by the process set forth in Example IA with 2,3,3-trimethylindolenine and ethyl 5-bromopentanoate to produce 2.65 grams (78 percent yield) of reddish-yellow crystals. $^1H$ and $^{13}C$ NMR spectra indicated the following:

$^1H$ NMR (400.1 MHz) in DMSO-$d_6$: δ 8.02 (1H, m), 7.83 (1H, m), 7.61 (2H, m), 4.48 (2H, t, J=6, N—$CH_2$), 4.01 (2H, t, J=7, O—$CH_2$), 2.84 (3H, s, $CH_3$), 2.40 (2H, t, J=7, $CH_2CO$), 2.08 (4H, m, —$CH_2$), 1.53 (6H, s, $CH_3$), 1.13 (3H, t, J=7 Hz).

$^{13}C$ NMR (100.1 MHz) in DMSO-$d_6$: 197.0, 173.8, 172.3, 141.9, 141.2, 129.4, 128.9, 123.6, 115.3, 60.2, 54.3, 46.9, 30.3, 22.4, 22.0, 14.1.

IC

Synthesis of N-(5-carboxypentyl)-2,3,3-trimethylindolinium Bromide

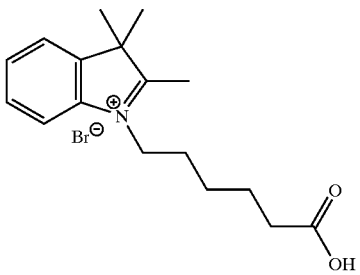

N-(5-carboxypentyl)-2,3,3-trimethylindolinium bromide was prepared by the process set forth in Example IA with 2,3,3-trimethylindolenine and 6-bromohexanoic acid to produce 2.43 grams (71.2 percent yield) of yellow crystals. $^1H$ and $^{13}C$ NMR spectra indicated the following:

$^1H$ NMR (400.1 MHz) in DMSO-$d_6$: δ 7.98 (1H, m), 7.86 (1H, m), 7.60 (2H, m), 4.46 (2H, t, J=6, N—$CH_2$), 2.85 (3H, s, $CH_3$), 2.21 (2H, t, J=7, $CH_2CO$), 1.83 (2H, m, —$CH_2$), 1.52 (6H, s, $CH_3$), 1.46 (4H, s, —$CH_2$—).

$^{13}C$ NMR (100.1 MHz) in DMSO-$d_6$: 196.9, 174.7, 142.3, 141.5, 129.6, 129.4, 123.9, 115.9, 54.6, 47.9, 33.8, 27.4, 25.8, 24.5, 22.4, 14.6.

ID

Synthesis of 2,3,3-trimethylindolinium-N-propylsufonate

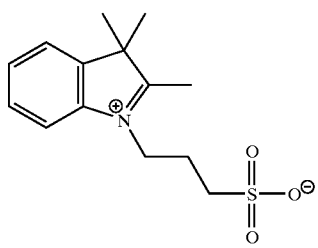

2,3,3-trimethylindolinium-N-propylsulfonate was prepared by the process set forth in Example IA with 2,3,3-trimethylindolenine and 1,3-propylsultone to produce 2.98 grams (94 percent yield) of white crystals. $^1$H and $^{13}$C NMR spectra indicated the following:

$^1$H NMR (400.1 MHz) in DMSO-$d_6$: δ 7.99 (1H, m), 7.77 (1H, m), 7.55 (2H, m), 4.60 (2H, t, J=7, N—CH$_2$), 2.78 (3H, s, CH$_3$), 2.61 (2H, t, J=7, CH$_2$SO$_3$-), 2.11 (2H, m, —CH$_2$—), 1.47 (6H, s, CH$_3$).

$^{13}$C NMR (100.1 MHz) in DMSO-$d_6$: 196.9, 142.2, 141.5, 129.6, 129.2, 123.7, 115.7, 54.4, 47.7, 46.9, 24.0, 22.3, 14.1.

IE

Synthesis of 2,3,3-trimethylindolinium-N-butylsulfonate

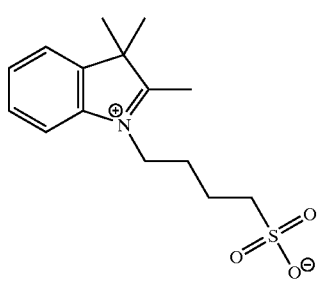

2,3,3-trimethylindolinium-N-butylsulfonate was prepared by the process set forth in Example IA with 2,3,3-trimethylindolenine and 1,4-butylsulfone to produce 2.86 grams (89.2 percent yield) of white crystals. $^1$H and $^{13}$C NMR spectra indicated the following:

$^1$H NMR (400.1 MHz) in DMSO-$d_6$: δ 8.03 (1H, m), 7.82 (1H, m), 7.60 (2H, m), 4.48 (2H, t, J=7, N—CH$_2$), 2.85 (3H, s, CH$_3$), 2.49 (2H, m, CH$_2$SO$_3$—), 1.97 (2H, m, —CH$_2$—), 1.76 (2H, m, —CH$_2$—) 1.53 (6H, s, CH$_3$).

$^{13}$C NMR (100.1 MHz) in DMSO-$d_6$: 196.9, 142.2, 141.5, 129.6, 129.2, 123.7, 115.7, 54.4, 47.7, 46.9, 24.0, 22.8, 22.3, 14.1.

EXAMPLE II

Preparation of Carboxylate Substituted Spiropyran Salts Step 2: Synthesis of 6-Nitro-Benzoindolino Spiropyrans (BIPS)

In the presence of a base, the functionalized salts were converted to an activated Fischer Base capable of undergoing a condensation reaction with 5-nitrosalicaldehyde. The solvent used in this reaction was ethanol, since the majority of spiropyrans are only partially soluble in this medium.

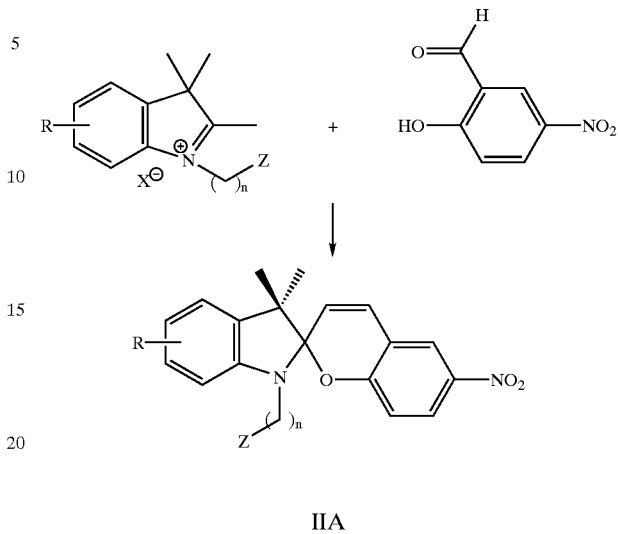

IIA

Synthesis of 6-Nitro-N-(2-carboxyethyl) Spirobenzoindolinopyran

The general procedure for the preparation of the spiropyrans is illustrated through the condensation of 2-carboxyethyl-2,3,3-trimethylindolinium iodide with 5-nitrosalicaldehyde in the presence of a base, triethylamine.

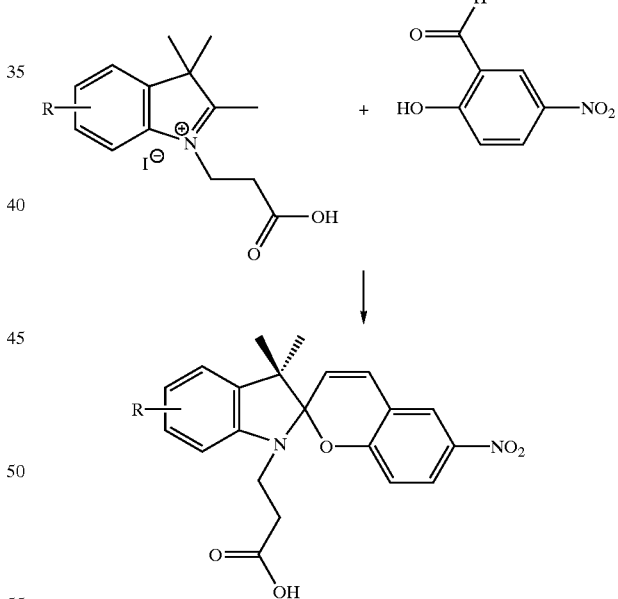

Into a 50 milliliter round-bottomed flask equipped with a water condenser topped with a pressure-equalized dropping funnel was added 2-carboxyethyl-2,3,3-trimethylindolinium iodide (prepared as described in Example IA; 1.0 gram, 2.78 mmol) and 5-nitrosalicaldehyde (0.50 gram, 3.0 mmol). Ethanol was added until the solids dissolved at reflux temperature, followed by addition of triethylamine (0.280 gram, 2.78 mmol) in 5 milliliters of ethanol via the dropping funnel over 20 minutes. Addition of the base resulted in an immediate color change to purple, signifying that spiropyran formation was occurring. The mixture was refluxed for 6 hours and then cooled to room temperature. The volume was concentrated to 5 milliliters before cooling the flask to 0° C. in a refrigerator for 24 hours. The spiropyran precipitate was filtered under vacuum and recrystallized from ethanol to give yellow crystals of 6-nitro-N-(2-carboxyethyl) spirobenzoindol inopyran, yield 0.763 grams (72.2 percent), melting point 192–194° C. $^1$H NMR, $^{13}$C NMR, IR, and UV-visible spectra indicated the following:

$^1$H NMR (400.1 MHz) in DMSO-$d_6$: δ 8.21 (1H, d, J=3), 8.00 (1H, d, J=9), 7.21 (1H, d, J=10.5), 7.11 (2H, m), 6.87 (2H, m), 6.67 (1H, d, J=7.8), 6.00 (1H, d, J=10.5), 3.42 (2H, J=6, N—$CH_2$), 2.50 (2H, t, J=6, $CH_2$CO), 1.18 (3H, s, $CH_3$), 1.07 (3H, s, $CH_3$).

$^{13}$C NMR (100.1 MHz) in DMSO-$d_6$: 173.7, 159.9, 146.9, 141.3, 136.5, 129.0, 128.5, 126.5, 123.6, 122.6, 120.1, 119.7, 116.3, 107.5, 107.3, 53.5, 34.0, 26.4, 20.3.

IR (KBr, cm$^{-1}$): 3030, 3000, 2971, 1709, 1654, 1610, 1575, 1510, 1483, 1457, 1441, 1360, 1330, 1270, 1141, 1088, 1020, 915, 803.

UV-Visible (DMSO, $\lambda_{max}(\epsilon)$): 336 nm, 9,600 M$^{-1}$cm$^{-1}$.

Elemental analysis: Calculated for $C_{21}H_{20}O_5N_2$: C, 65.30; H, 5.26, N, 7.30.

Found: C, 64.96; H, 5.23; N, 7.22.

IIB

Synthesis of 6-Nitro-(N-ethylpentanoyl) spirobenzoindolinopyran

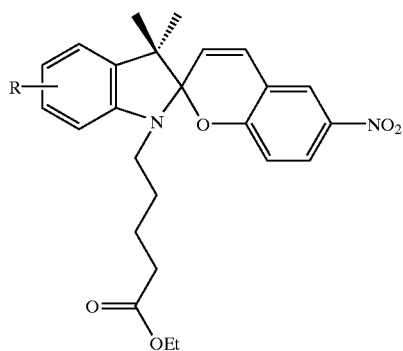

6-Nitro-(N-ethylpentanoyl)spirobenzoindolinopyran was prepared by the process set forth in Example IIA with 5-nitrosalicaldehyde and N-(ethylpentanoyl)-2,3,3-trimethylindolinium bromide (prepared as described in Example IB). $^1$H NMR spectra indicated the following:

$^1$H NMR (400.1 MHz) in CDCl$_3$: δ 7.99 (2H, m), 7.15 (1H, t), 7.06 (1H, d), 6.86 (2H, t), 6.72 (1H, d), 6.60 (1H, t), 5.85 (1H, d), 4.08 (2H, q, O—$CH_2$), 3.17 (2H, t), 2.39 (2H, $CH_2$CO), 2.00 (4H, m, —$CH_2$), 1.22 (9H, m, $CH_3$).

Deprotection of the Chelating Functionality

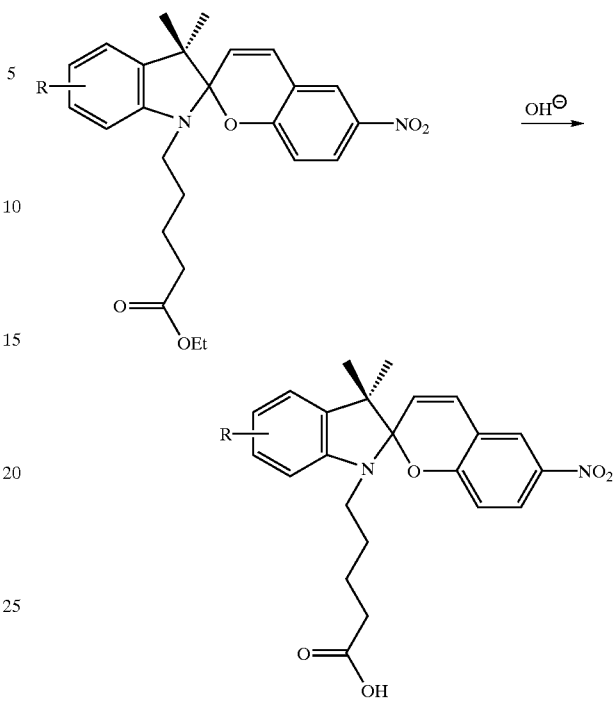

To a 50 milliliter round-bottomed flask equipped with a magnetic stir bar and an argon inlet was added finely ground 6-nitro-(N-ethylpentanoate)spirobenzoindolinopyran (1.0 gram, 2.28 mmol) and dissolved in 10 milliliters of THF. Sodium hydroxide (25 milliliters of a 1 Molar solution) was added to the solution and stirred for 24 hours before rotary evaporation at room temperature under high vacuum. The solids were dissolved in a minimum amount of water and the product was precipitated through neutralization with 1 Molar hydrochloric acid. Vacuum filtration isolated the solid, which was recrystallized from ethanol to yield 0.962 gram of yellow-red crystals of 6-nitro-(N-4-carboxylbutyl) spirobenzoindolinopyran (94 percent yield), melting point 139–141° C. $^1$H NMR, $^{13}$C NMR, IR, and UV-visible spectra indicated the following:

$^1$H NMR (400.1 MHz) in DMSO-$d_6$: δ 8.19 (1H, d, J=2.8), 7.97 (1H, d, J=9.0), 7.19 (1H, d, J=10.4), 7.08 (2H, m), 6.84 (1H, d, J=7.2), 6.76 (1H, t, J=7.2), 6.57 (1H, d, J 7.8), 5.98 (1H, d, J=10.4), 3.10 (2H, m, N—$CH_2$), 2.16 (2H, t, J=6.8, $CH_2$CO), 1.55 (4H, m, —$CH_2$—), 1.18 (3H, s, $CH_3$), 1.09 (3H, s, $CH_3$).

$^{13}$C NMR: 174.4, 159.2, 146.7, 140.4, 135.6, 128.1, 127.6, 125.7, 122.8, 121.6, 118.9, 118.7, 115.4, 106.4, 52.2, 33.5, 28.0, 26.1, 24.2, 19.5.

IR (cm$^{-1}$): 3030, 3000, 2971, 1709, 1654, 1610, 1575, 1510, 1483, 1457, 1441, 1360, 1330, 1270, 1141, 1088, 1020, 915, 803.

UV-Visible (DMSO, $\lambda_{max}$ ($\epsilon$)): 338 nm, 7,800 M$^{-1}$cm$^{-1}$.

Elemental analysis: Calculated for $C_{23}H_{24}O_5N_2$: C, 67.61; H, 5.89; N, 6.82.

Found: C, 67.31; H, 5.92; N, 6.60.

IIC

Synthesis of 6-nitro-N-(5-carboxypentyl) spirobenzoindolinopyran

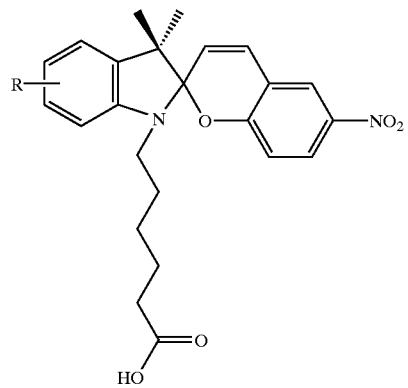

6-nitro-N-(5-carboxypentyl)spirobenzoindolinopyran was prepared by the process set forth in Example IIA with 5-nitrosalicaldehyde and N-(5-carboxypentyl)-2,3,3-trimethylindolinium bromide (prepared as described in Example IC) to produce 1.23 grams (48 percent yield) of yellow-red crystals, melting point 80–82° C. $^1$H NMR, $^{13}$C NMR, IR, and UV-visible spectra indicated the following:

$^1$H NMR (400.1 MHz) in DMSO-$d_6$: δ 8.19 (1H, d, J=3.2), 8.00 (1H, d, J=9.0), 7.21 (1H, d, J=10.5), 7.08 (2H, m), 6.80 (2H, m), 6.57 (1H, d, J=7.8), 5.98 (1H, d, J=10.5), 3.10 (2H, m, N—CH$_2$), 2.13 (2H, m, CH$_2$CO), 1.45 (4H, m, —CH$_2$—), 1.20 (2H, m, —CH$_2$—), 1.18 (3H, s, CH$_3$), 1.07 (3H, s, CH$_3$).

$^{13}$C NMR: 174.4, 159.2, 146.7, 140.4, 135.6, 128.1, 127.6, 125.7, 122.8, 121.6, 118.9, 118.7, 115.4, 106.4, 52.2, 33.5, 28.0, 26.1, 25.8, 24.2, 19.5.

IR (cm$^{-1}$): 3030, 3000, 2971, 1709, 1654, 1610, 1575, 1510, 1483, 1457, 1441, 1360, 1330, 1270, 1141, 1088, 1020, 915, 803.

UV-Visible (DMSO, $\lambda_{max}$ (ε)): 342 nm, 8,400 M$^{-1}$ cm$^{-1}$.

Elemental analysis: Calculated for C$_{24}$H$_{25}$O$_5$N$_2$: C, 68.20; H, 6.16; N, 6.70.

Found: C 68.30; H, 6.09, N, 6.52.

Step 3: Preparation of Carboxylate Salts

Preparation of the carboxylate salts entailed the treatment of an alcoholic solution of the spiropyran with about 1 molar equivalent of NaOEt or KOEt. A representative procedure is described through the reaction of 6-nitro-(N-carboxyethyl) spirobenzoindolinopyran with NaOEt:

IID

Synthesis of 6-Nitro-spirobenzoindolinopyran-N-ethylsodiumcarboxylate

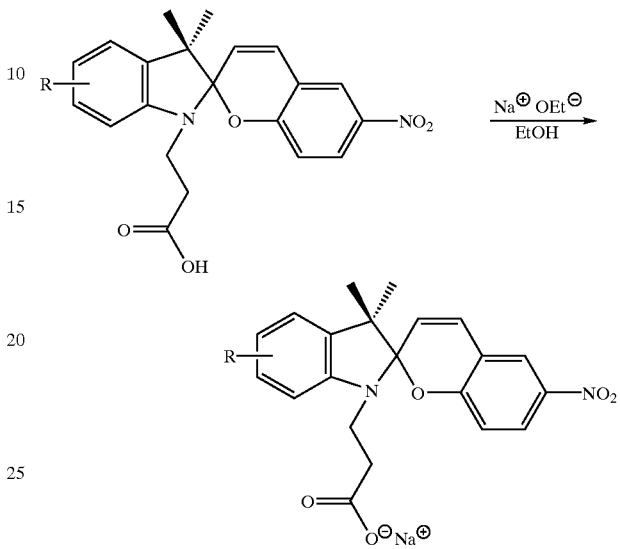

In a 50 milliliter round-bottomed flask equipped with a magnetic stir bar and an argon inlet was added finely ground 6-nitro-(N-carboxyethyl)spirobenzoindolinopyran (0.100 gram, 0.263 mmol) prepared as described in Example IIA and dissolved in 5 milliliters of ethanol. The mixture was then cooled to 0° C. in an ice bath before adding through a syringe 3.0 milliliters of an 8.64×10$^{-2}$ Molar NaOEt (0.265 mmol) solution. The reaction was stirred for 3 hours before rotary evaporation at room temperature under high vacuum. Recrystallization from ethanol gave 100 milligrams of yellow-red crystals of 6-nitro-spirobenzoindolinopyran-N-ethylsodiumcarboxylate (94.6 percent yield), melting point 202–204° C. $^1$H NMR, $^{13}$C NMR, IR, and UV-visible spectra indicated the following:

$^1$H NMR (400.1 MHz) in DMSO-$d_6$: δ 8.17 (1H, d, J=2.8), 7.96 (1H, d, J=9.0), 7.15 (1H, d, J=10.5), 7.07 (2H, m), 6.83 (1H, d, J=9), 6.73 (1H, t, J=7.3), 6.58 (1H, d, J=8.0), 5.98 (1H, d, J=10.5), 3.23 (2H, m, N—CH$_2$), 2.19 (2H, m, CH$_2$CO), 1.16 (3H, s, CH$_3$), 1.05 (3H, s, CH$_3$).

$^{13}$C NMR: 173.3, 159.2, 146.5, 140.3, 135.5, 127.7, 127.5, 125.5, 122.6, 122.0, 121.4, 118.8, 118.6, 115.3, 106.5, 106.4, 52.2, 36.2, 25.7, 19.5.

IR (cm$^{-1}$): 3020, 2970, 2923, 1652, 1607, 1588, 1507, 1480, 1450, 1330, 1275, 1218, 1156, 1123, 1090, 1020, 910, 803.

UV-Visible (DMSO, $\lambda_{max}$ (ε)): 338 nm, 8,400 M$^{-1}$ cm$^{-1}$.

Elemental analysis (High resolution mass spectrometer (HRMS), fast atom bombardment with positive ions (FAB+)): Calculated for C$_{21}$H21O$_5$N$_2$: 381.1451.

Found: 381.1399.

IIE

Synthesis of 6-Nitrospirobenzoindolinopyran-N-butylpotassiumcarboxylate

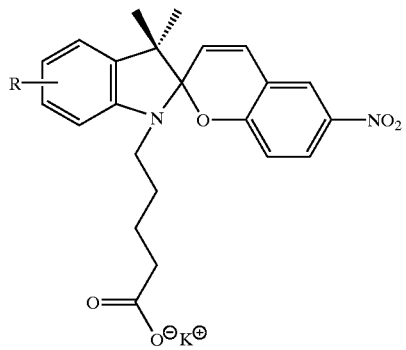

6-Nitrospirobenzoindolinopyran-N-butylpotassium carboxylate was prepared by the process set forth in Example IID with 6-nitro-(N-ethyl pentanoyl)spirobenzoindol inopyran (prepared as described in Example IIB) to produce 0.94 gram of red crystals (94 percent yield), melting point 180–182° C. $^1$H NMR, $^{13}$C NMR, IR, and UV-visible spectra indicated the following:

$^1$H NMR (400.1 M Hz) in DMSO-d$_6$: δ 8.18 (1H, d, J=2,6), 7.97 (1H, d, J=9.0), 7.18 (11H, d, J=10.5), 7.10 (2H, m), 6.85 (1H, d, J=9), 6.74 (1H, t, J=7.3), 6.57 (1H, d, J=7.8), 5.98 (1H, d, J=10.5), 3.49 (1H, m, N—CH), 3.05 (1H, m, N—CH), 1.81 (2H, m, CH$_2$CO), 1.32 (2H, m, —CH$_2$—), 1.20 (2H, m, —CH$_2$—), 1.1 (3H, S, CH$_3$), 1.07 (3H, s, CH$_3$).

$^{13}$C NMR: 174.4, 159.2, 146.7, 140.4, 135.6, 128.1, 127.6, 125.7, 122.8, 121.6, 118.9, 118.7, 115.4, 106.6, 106.4, 52.2, 42.7, 28.0, 26.1, 25.8, 19.5.

IR (cm$^{-1}$): 3020, 2970, 2923, 1652, 1607, 1588, 1507, 1480, 1450, 1330, 1275, 1218, 1156, 1123, 1090, 1020, 910, 803.

UV-Visible (DMSO, λ$_{max}$ (ε)) 342 nm, 8,400 M$^{-1}$cm$^{-1}$.

Elemental analysis (HRMS (FAB+)): Calculated for C$_{23}$H$_{24}$O$_5$N$_2$K: 447.2677
Found: 447.2688.

IIF

Synthesis of 6-Nitrospirobenzoindolinopyran-N-pentylpotassium Carboxylate

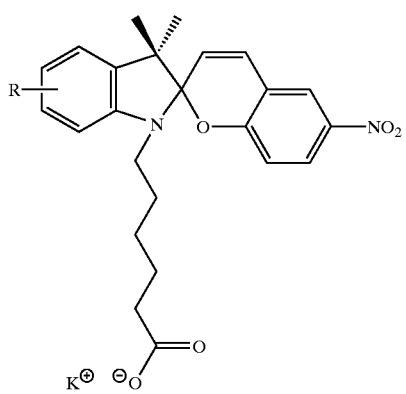

6-Nitrospirobenzoindolinopyran-N-pentylpotassium carboxylate was prepared by the process set forth in Example IID with 6-nitro-N-(5-carboxypentyl) spirobenzoindolinopyran (prepared as described in Example IIC) to produce 0.54 grams (73 percent yield) of dark red 6-nitrospirobenzoindolinopyran-N-pentylpotassium carboxylate crystals, melting point 100–102° C. $^1$H NMR, $^{13}$C NMR, IR, and UV-visible spectra indicated the following:

$^1$H NMR (400.1 MHz) in DMSO-d$_6$: δ 8.17 (1H, d, J=2.8), 7.97 (1H, d, J=9.0), 7.18 (1H, d, J=10.5), 6.84 (2H, m), 6.84 (1H, d, J=9), 6.77 (11H, t, J=7.6), 6.55 (1H, d, J=7.8), 5.98 (1H, d, J=10.5), 3.10 (2H, m, N—CH$_2$), 1.79 (2H, m, CH$_2$CO), 1.45 (4H, m, —CH$_2$—), 1.20 (2H, m, —CH$_2$—), 1.18 (3H, s, CH$_3$), 1.05 (3H, s, CH$_3$).

$^{13}$C NMR: 174.4, 159.2, 146.7, 140.4, 135.6, 128.1, 127.6, 125.7, 125.2, 122.8, 121.8, 118.8, 118.7, 115.4, 106.4, 52.2, 43.0, 33.5, 28.0, 26.1, 25.8, 24.2, 19.5, 14.1.

IR (cm$^{-1}$): 3020, 2970, 2923, 1652, 1607, 1588, 1507, 1480, 1450, 1330, 1275, 1218, 1156, 1123, 1090, 1020, 910, 803.

UV-Visible (DMSO, λ$_{max}$ (ε)): 342 nm, 8,400 M$^{-1}$ cm$^{-1}$.

Elemental analysis (HRMS (FAB+)): Calculated for C$_{24}$H$_{25}$O$_5$N$_2$K: 461.2424.
Found: 461.2445.

EXAMPLE III

Preparation of Sulfonate Substituted Spiropyran Salts

Step 2: Synthesis of 6-nitro-benzoindolino Spiropyrans (BIPS)

IIIA

Synthesis of 6-Nitro-spirobenzoindolinopyran-N-propyl-triethylammoniumsulfonate

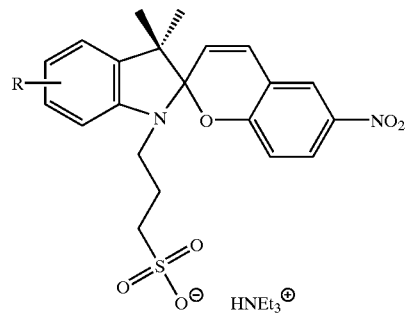

6-Nitro-spirobenzoindolinopyran-N-propyl-triethyl ammoniumsulfonate was prepared by the process set forth in Example IIA with 5-nitrosalicaldehyde and 2,3,3-trimethylindolinium-N-propylsulfonate (prepared as described in Example ID). The product was recrystallized from ethyl acetate to produce 1.43 grams (52 percent yield) of yellow crystals, melting point 188–190° C. $^1$H NMR, $^{13}$C NMR, IR, and UV-visible spectra indicated the following:

$^1$H NMR (400.1 MHz) in DMSO-d$_6$: δ 8.27 (1H, d, J=2.8), 8.04 (1H, d, J=9.0), 7.26 (1H, d, J=10.4), 7.15 (2H, m), 6.83 (3H, m), 6.03 (1H, d, J=10.4), 3.29 (2H, t, J=7.3, N—CH$_2$), 3.13 (6H, q, J=7.3, CH$_2$CH$_3$), 2.50 (2H, m, CH$_2$SO$_3$) 1.49 (2H, m, —CH$_2$—), 1.25 (9H, t, CH$_3$), 1.19 (3H, s, CH$_3$), 1.16 (3H, s, CH$_3$).

$^{13}$C NMR: 159.2, 146.7, 140.4, 135.5, 128.1, 127.6, 125.7, 122.8, 121.6, 121.5, 118.9, 118.7, 115.4, 106.4, 106.4, 52.2, 49.0, 45.7, 42.2, 24.7, 19.5, 8.55.

IR (cm$^{-1}$): 3020, 2970, 2684, 2510, 1652, 1607, 1510, 1483, 1457, 1333, 1275, 1218,1156,1123,1089, 1020,916,805.

UV-Visible (DMSO, $\lambda_{max}$ ($\epsilon$)): 342 nm, 8,600 $M^{-1}$ $cm^{-1}$.
Elemental analysis: Calculated for $C_{27}H_{37}O_6N_3S$: C, 61.05; H, 6.70; N, 7.90; S, 5.94.
Found: C, 61.30; H, 6.67; N, 7.83; S, 5.86.

IIIB

Synthesis of 6-Nitro-spirobenzoindolinopyran-N-butyl-triethylammoniumsulfonate

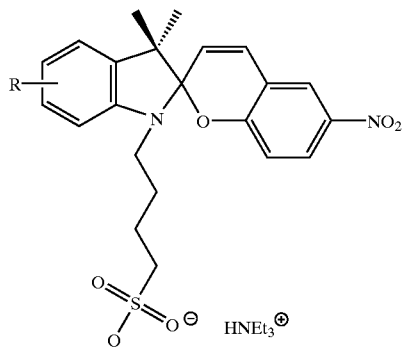

6-nitro-spirobenzoindolinopyran-N-butyl-triethylammonium sulfonate was prepared by the process set forth in Example IIA with 5-nitrosalicaldehyde and 2,3,3-trimethylindolinium-N-butylsulfonate (prepared as described in Example IE). The product was recrystallized from ethyl acetate to produce 0.86 gram (36 percent yield) of purple crystals, melting point 208–210° C. $^1$H NMR, $^{13}$C NMR, IR, and UV-visible spectra indicated the following:
$^1$H NMR (400.1 MHz) in DMSO-$d_6$: δ 8.27 (1H, d, J=2.8), 8.04 (1H, d, J=9.0), 7.26 (1H, d, J=10.4), 7.15 (2H, m), 6.83 (3H, m), 6.03 (1H, d, J=10.4), 3.29 (2H, t, J=7.3, N—$CH_2$), 3.13 (6H, q, J=7.3, $CH_2CH_3$), 2.50 (2H, m, $CH_2SO_3$) 1.49 (4H, m, —$CH_2$—), 1.25 (9H, t, $CH_3$), 1.19 (3H, s, $CH_3$), 1.16 (3H, s, $CH_3$).
$^{13}$C NMR: 159.2, 146.7, 140.4, 135.6, 128.1, 127.6, 125.7, 122.8, 121.6, 118.9, 118.7, 115.4, 106.4, 59.7, 52.2, 42.5, 33.3, 28.0, 25.8, 24.2, 22.1, 19.5, 14.0.
IR ($cm^{-1}$): 3020, 2970, 2684, 2510, 1652, 1607, 1510, 1483, 1457, 1333, 1275, 1218, 1156, 1123, 1089, 1020, 916, 805.
UV-Visible (DMSO, $\lambda_{max}$ ($\epsilon$)): 344 nm, 9,000 $M^{-1}$ $cm^{-1}$.
Elemental analysis: Calculated for $C_{28}H_{39}O_6N_3S$: C, 59.70; H, 6.90; N, 7.52; S, 5.70.
Found: C, 59.64; H, 6.84, N, 7.43; S, 5.62.

EXAMPLE IV

A first wax is made by dispersing 50 grams of the spiropyran 6-nitro-spirobenzoindolinopyran-N-ethylsodiumcarboxylate prepared as described in Example IID and 13.6 grams of zinc chloride into 200 grams of POLYWAX® 1000 (Baker-Petrolite). This wax and a white wax of POLYWAX® 1000 containing 20 percent by weight TiO2 pigment are used to make bichromal balls by the method set forth in U.S. Pat. No. 5,262,098, the disclosure of which is totally incorporated herein by reference. The balls thus formed are sieved into fractions, and the 90–106 micron fraction is used to make an elastomer sheet. The sheet is made by mixing 5 grams of SYLGARD® 184 base, 0.75 gram SYLGARD® 184 curing agent, and 5.75 grams of the 90 to 106 micron balls, placing the mixture under vacuum to de-aerate; casting the mixture into a 0.012 inch sheet, and curing at 90° C. for 2 hours. After curing, small subsheets are cut out and soaked in ISOPAR® L with anhydrous calcium sulfate overnight.

The subsheets are made into displays by mounting them between two glass plates coated with indium tin oxide. The surface of the glass plates with the indium tin oxide coating is placed on the inside adjacent to the subsheet. In the final test display, the components from one side to the other are glass plate # 1, ITO coating on glass plate # 1, soaked subsheet, ITO coating on glass plate # 2, glass plate # 2.

EXAMPLE V

The process of Example IV is repeated except that the spiropyran 6-nitro-spirobenzoindolinopyran-N-ethylsodiumcarboxylate is replaced with the spiropyran 6-nitrospirobenzoindolinopyran-N-butylpotassium carboxylate prepared as described in Example IIE.

EXAMPLE VI

The process of Example IV is repeated except that the spiropyran 6-nitro-spirobenzoindolinopyran-N-ethylsodiumcarboxylate is replaced with the spiropyran 6-ntrospirobenzoindolinopyran-N-pentylpotassium carboxylate prepared as described in Example IIF.

EXAMPLE VII

The process of Example IV is repeated except that the spiropyran 6-nitro-spirobenzoindolinopyran-N-ethylsodiumcarboxylate is replaced with the spiropyran 6-nitro-spirobenzoindolinopyran-N-propyl-triethyl ammoniumsulfonate prepared as described in Example IIIA.

EXAMPLE VIII

The process of Example IV is repeated except that the spiropyran 6-nitro-spirobenzoindolinopyran-N-ethylsodiumcarboxylate is replaced with the spiropyran 6-nitro-spirobenzoindolinopyran-N-butyl-triethylammonium sulfonate prepared as described in Example IIIB.

EXAMPLE IX

The processes of Examples IV through VIII are repeated except that the white wax containing 20 percent by weight TiO2 pigment is replaced with a black wax of POLYWAX® 1000 containing 20 percent by weight F-6331 pigment (Ferro Corp.).

EXAMPLE X

Preparation of 17 micron bichromal spheres wherein one hemisphere is a white surface coated with poly (trifluorethylmethacrylate) and the other hemisphere is a surface having a spiropyran and chelating agent thereon, and wherein the resin is a polyester resin, the white pigment or whitening agent is titanium dioxide, and the spiropyran is 6-nitro-spirobenzoindolinopyran-N-ethylsodiumcarboxylate prepared in Example IID.

Step 1: Preparation of White Monochromal Spheres 50 grams of the sulfonated polyester resin copoly (propylene-diethylene-terephthalate) copoly(propylene-diethylene-5-sulfo-isopthalate) prepared as described in Example I of U.S. Pat. No. 5,593,807, the disclosure of which is totally incorporated herein by reference, is hydro-dispersed in 250 grams of water at 60° C. The resulting polyester emulsion is then cooled to room temperature, about 25° C. throughout, and to this emulsion is added 10 grams of a titanium oxide dispersion in water (said dispersion containing 50 percent by weight titanium oxide solids; available from Sun Chemicals). The resulting mixture is then homogenized at about 1,000 rpm with the slow addition of a 5 weight percent magnesium chloride aqueous solution (50 milliliters), and the resulting mixture is then transferred to a 1 liter kettle. The mixture is then stirred at 200 rpm and heated to 55° C. overnight, about 18 hours, to yield about 50 grams of monochromal white spheres of 17.6 microns in volume average diameter as measured using a Coulter Counter, and with a geometric size distribution (GSD) of 1.13.

Step 2: Surface Polymerization of the White Monochromal Spheres

To 10 grams of the white spheres prepared above in Step 1 in 100 milliliters of water is added 0.25 grams of cerium ammonium nitrate and 1 milliliter of a 1 Normal solution of nitric acid. The resulting mixture is stirred for 3, hours followed by filtration of the white spheres and resuspension of the spheres in 100 milliliters of water. To this suspension is then added 0.25 grams of potassium persulfate, 0.25 grams of sodium bisulfite, and 0.5 grams of triflouroethyl acrylate. The resulting mixture is then stirred for three hours at room temperature (about 25° C.), and the resulting surface grafted monochromal spheres are then filtered, washed with water, and re-suspended in about 1 liter of water.

Step 3: Coating of Spheres on Glass and Thermal Vapour Deposition Using Spiropyran and Chelating Agent The monochromal charged white spheres resulting from Step 2 are then uniformly coated as a monolayer of a thickness of less than about 500 nanometers, such as about 400 nanometers, on a glass slide substrate by Langmiur Blodget techniques and left air drying for about 18 hours, The spheres are then subjected to vacuum, such as from about 0.0001 to about 0.1 mmHg, and then sublimed with the spiropyran 6-nitro-spirobenzoindolinopyran-N-ethylsodiumcarboxylate prepared as described in Example IID, said spiropyran being admixed prior to sublimation with calcium chloride in a molar ratio of 5 moles calcium chloride per every one mole of spiropyran. The resulting bichromal white/spiropyran spheres have nearly equal portions of spiropyran and white coverage. The 0.3 micron thick spiropyran layer has little affect on the ball diameter, which remains at about 17 microns diameter. In this Example, the fluoroacrylated white side of the ball is believed to be negatively charged and the spiropyran coated side of the ball is believed to be positively charged.

Step 4: Fabrication of a Display Sheet

A display sheet is fabricated from the bichromal spheres prepared in Step 3 by (1) mixing 50 grams of the prepared bichromal spheres with 50 grams of SYLGARD® 185 silicone elastomer it available from Dow Corning, (2) forming a sheet by spreading the mixture on a glass plate surface and with a metering bar such as an 8-Path Wet Film Applicator (available from P. Gardner Company) with a gap of from about 20 microns to about 500 microns, and crosslinking the SYLGARD® elastomer sheet by heating it to a temperature of from about 80° C. to about 100° C. for a duration of from about 3 to about 24 hours; (3) plasticizing the sheet by immersing it in a vessel containing a suitable oil such as ISOPAR® L in an amount of from about 50 to about 500 milliliters to form oil-filled cavities within the sheet; and (4) removing the sheet from the oil vessel and sealing it between addressing plates of MYLAR® with a thickness of about 5 to about 15 microns, or indium tin oxide glass with a similar thickness.

Other embodiments and modifications of the present invention may occur to those of ordinary skill in the art subsequent to a review of the information presented herein; these embodiments and modifications, as well as equivalents thereof, are also included within the scope of this invention.

What is claimed is:

1. A display comprising an arrangement of a plurality of optically anisotropic rotatable elements, each of said rotatable elements having a surface in contact with an enabling fluid, said rotatable elements being electrically dipolar in the presence of the enabling fluid and thus being subject to rotation upon application of an electric field, said rotatable elements being free to rotate in place but not free to translate substantially so as to disrupt the arrangement of rotatable elements, wherein a first portion of said surface contains a mixture of a chelating agent and a spiropyran material of the formula

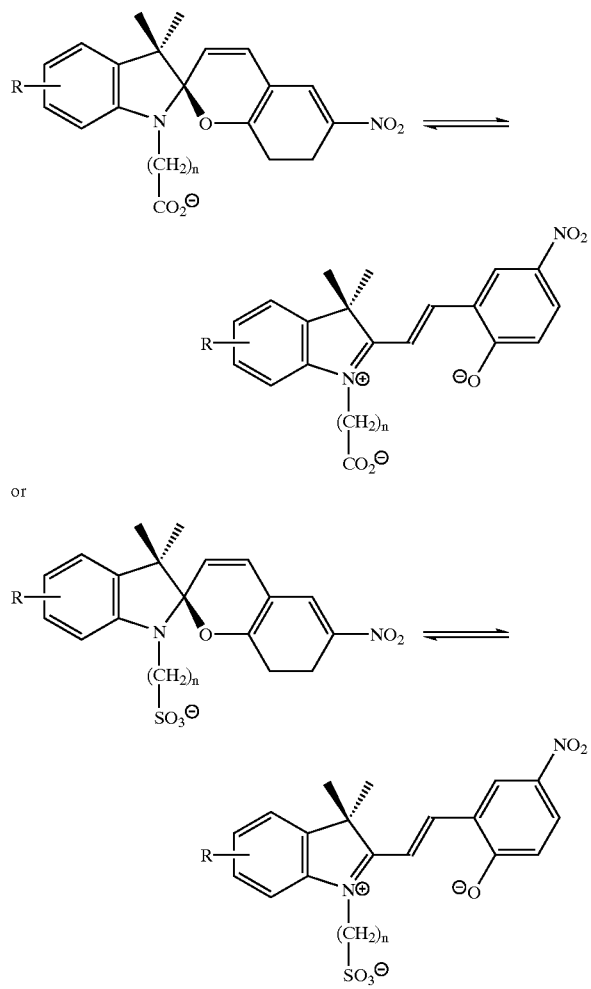

or wherein n is an integer representing the number of repeat —CH$_2$— units and R is —H or —CH=CH$_2$, and wherein a second portion of said surface contains substantially no spiropyran.

2. A display according to claim 1 wherein the spiropyran material is of the formula

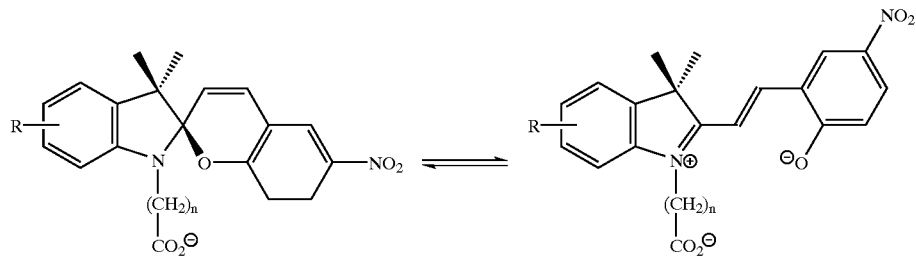

wherein n is an integer of from about 2 to about 8.

3. A display according to claim 1 wherein the spiropyran material is of the formula

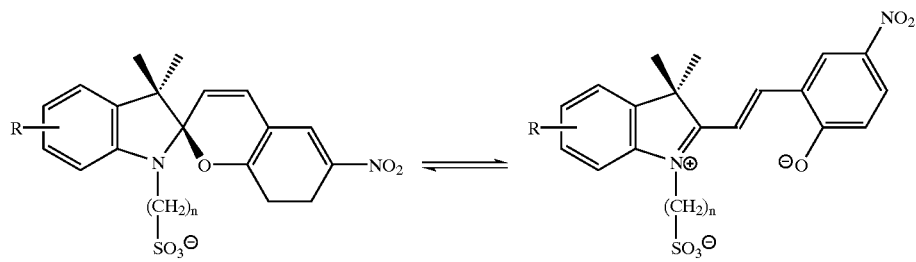

wherein n is an integer of from about 2 to about 8.

4. A display according to claim 1 wherein the spiropyran material is of the formula

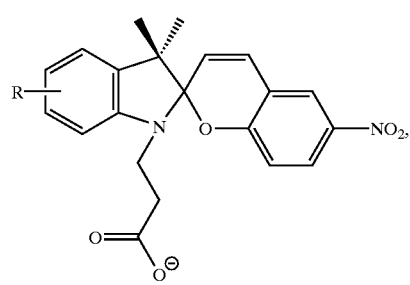

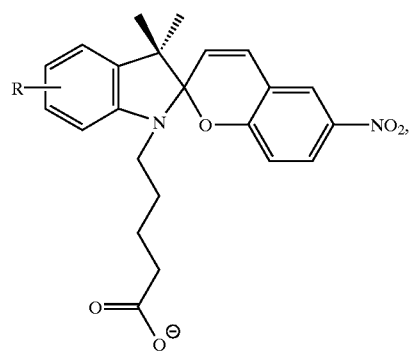

-continued

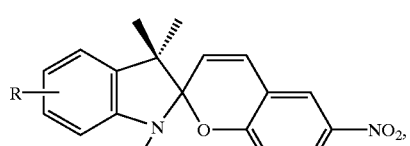

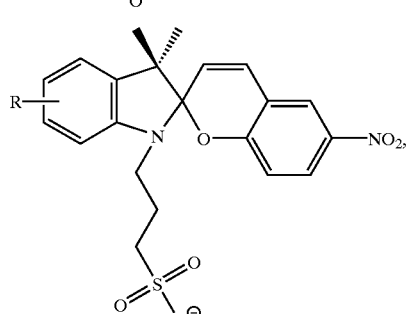

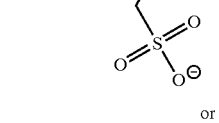

or

-continued

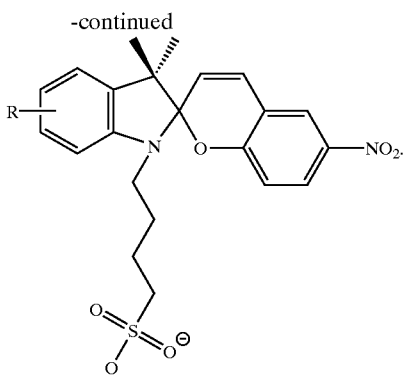

5. A display according to claim 1 wherein the spiropyran material is present in the rotatable elements in an amount of at least about 0.01 percent by weight of the rotatable elements.

6. A display according to claim 1 wherein the spiropyran material is present in the rotatable elements in an amount of at least about 0.05 percent by weight of the rotatable elements, and wherein the spiropyran material is present in the rotatable elements in an amount of no more than about 5 percent by weight of the rotatable elements.

7. A display according to claim 1 wherein the chelating agent is a metal salt in the +2 state.

8. A display according to claim 1 wherein the chelating agent is a salt of calcium, magnesium, zinc, or a transition metal.

9. A display according to claim 1 wherein the chelating agent is present in the rotatable elements in an amount relative to the spiropyran material of at least about 1 mole of chelating agent for every 1 mole of spiropyran material.

10. A display according to claim 1 wherein the chelating agent is present in the rotatable elements in an amount relative to the spiropyran material of at least about 2 moles of chelating agent for every 1 mole of spiropyran material, and wherein the chelating agent is present in the rotatable elements in an amount relative to the spiropyran material of no more than about 10 moles of chelating agent for every 1 mole of spiropyran material.

11. A display according to claim 1 wherein the rotatable elements are spherical in shape.

12. A display according to claim 1 wherein the rotatable elements are cylindrical in shape.

13. A display according to claim 1 wherein the rotatable elements are prismatic in shape.

14. A display according to claim 1 wherein the rotatable elements are disposed in cavities in a substrate, said cavities also containing the enabling fluid.

15. A display according to claim 14 wherein the rotatable elements are disposed in the substrate in a closely packed monolayer.

16. A display according to claim 14 wherein the substrate comprises an elastomer.

17. A display according to claim 1 comprising (a) a member having an optically transmissive viewing surface, (b) a closely packed stable layer arrangement of the rotatable elements rotatably disposed in the enabling fluid behind the viewing surface with respect to an observer situated favorably to observe the viewing surface, at least some of the rotatable elements thus being observable by the observer through the viewing surface, neighboring rotatable elements tending to keep one another in place in the arrangement, and (c) a retaining structure to retain in place with respect to the viewing surface the rotatable elements thus disposed, the retaining structure being disposed entirely outside the layer of rotatable elements and not occupying any spaces between the rotatable elements in the layer.

18. A display according to claim 1 wherein the rotatable elements are encapsulated within microcapsules which also contain the enabling fluid, and wherein the microcapsules are dispersed in a substrate.

19. A display according to claim 1 wherein the rotatable elements are of two populations, said first population comprising rotatable elements of a first substantially uniform diameter and said second population comprising rotatable elements of a second substantially uniform diameter, wherein the diameter of rotatable elements of the second population is smaller than the diameter of rotatable elements of the first population and wherein the diameter of rotatable elements of the second population is such that the rotatable elements in the second population can fill interstices left by close-packing the rotatable elements from the first population.

20. A display according to claim 1 wherein the enabling fluid is selected from paraffinic hydrocarbons, fluorinated hydrocarbons, vegetable oils, triglyceride liquids, silicon oils, or mixtures thereof.

21. A display according to claim 1 wherein the rotatable elements comprise a material selected from glass, silicon, plastics, aluminum, epoxies, waxes, or mixtures thereof.

22. A display according to claim 1 wherein the rotatable elements comprise a core and a partial coating on said core, wherein the spiropyran and chelating agent are contained within the core, and wherein the partial coating is the second portion of the surface of the rotatable element.

23. A display according to claim 1 wherein the rotatable elements comprise a core and a partial coating on said core, wherein the spiropyran and chelating agent are contained within the coating, and wherein the partial coating is the first portion of the surface of the rotatable element.

24. A display according to claim 1 wherein the rotatable elements have at least three aspects.

25. A display according to claim 1 wherein a third portion of said rotatable element surface contains substantially no spiropyran and wherein said third portion is of a different color from the second portion.

26. A display according to claim 25 wherein said third portion is of a different color from the first portion.

27. A process which comprises (a) providing a display according to claim 1; (b) applying to the display an electrical field, thereby causing a first population of said rotatable elements to rotate so that said first portion is oriented toward a viewer and causing a second population of said rotatable elements to rotate so that said second portion is oriented toward the viewer; and (c) exposing said display to radiation at a wavelength effective to cause the spiropyran material in the first portion of at least some members of the first population of rotatable elements to shift to a merocyanine form.

28. A process according to claim 27 wherein subsequent to step (c), the display is exposed to radiation at a wavelength effective to cause at least some of the rotatable elements containing the material in the merocyanine form to shift back to the spiropyran.

* * * * *